(12) United States Patent
Ajima

(10) Patent No.: US 11,594,118 B2
(45) Date of Patent: Feb. 28, 2023

(54) ELECTRONIC DEVICE

(71) Applicant: KYOCERA Corporation, Kyoto (JP)

(72) Inventor: Hiromi Ajima, Kawasaki (JP)

(73) Assignee: KYOCERA Corporation, Kyoto (JP)

( * ) Notice: Subject to any disclaimer, the term of this patent is extended or adjusted under 35 U.S.C. 154(b) by 0 days.

(21) Appl. No.: 17/290,796

(22) PCT Filed: Nov. 6, 2019

(86) PCT No.: PCT/JP2019/043502
§ 371 (c)(1),
(2) Date: May 3, 2021

(87) PCT Pub. No.: WO2020/105436
PCT Pub. Date: May 28, 2020

(65) Prior Publication Data
US 2021/0407276 A1 Dec. 30, 2021

(30) Foreign Application Priority Data
Nov. 19, 2018 (JP) .............................. JP2018-216644

(51) Int. Cl.
G08B 21/00 (2006.01)
G08B 21/18 (2006.01)
A61B 5/00 (2006.01)
G08B 7/06 (2006.01)

(52) U.S. Cl.
CPC ............ *G08B 21/18* (2013.01); *A61B 5/6843* (2013.01); *A61B 5/7405* (2013.01); *A61B 5/7455* (2013.01); *G08B 7/06* (2013.01); *A61B 2562/0209* (2013.01)

(58) Field of Classification Search
CPC ........ G08B 21/18; G08B 7/06; A61B 5/6843; A61B 5/7405; A61B 5/7455; A61B 2562/0209; A61B 5/4854; A61B 5/02444
See application file for complete search history.

(56) References Cited

U.S. PATENT DOCUMENTS

| 5,762,610 | A | 6/1998 | Narimatsu et al. |
| 10,231,631 | B2 | 3/2019 | Hirano |
| 10,856,783 | B2 | 12/2020 | Ajima |
| 2015/0366518 | A1* | 12/2015 | Sampson .............. A61B 5/0205 600/509 |
| 2017/0095165 | A1 | 4/2017 | Hirano |
| 2017/0251930 | A1* | 9/2017 | Machida .............. A61B 5/0059 |
| 2017/0360368 | A1* | 12/2017 | Aoshima ........... A63B 24/0062 |
| 2018/0000356 | A1 | 1/2018 | Ajima |
| 2018/0146871 | A1 | 5/2018 | Ajima |

(Continued)

FOREIGN PATENT DOCUMENTS

| CN | 204044660 U | * 12/2014 | ............. G06F 1/163 |
| JP | 2015-223339 A | 12/2015 | |

(Continued)

*Primary Examiner* — Toan N Pham
(74) *Attorney, Agent, or Firm* — Studebaker & Brackett PC

(57) ABSTRACT

An electronic device comprises a sensor, a notifier and a controller. The sensor is urged to a test part side of an examinee and can detect pulsation at the test part. The notifier notifies information for a position of the sensor at the test part. The controller controls the notifier to notify information for a position of the sensor at the test part based on pulsation at the test part detected by the sensor.

12 Claims, 33 Drawing Sheets

(56) References Cited

U.S. PATENT DOCUMENTS

2019/0282169 A1* 9/2019 Chen .................... A61B 5/6886
2019/0365255 A1 12/2019 Kitagawa et al.

FOREIGN PATENT DOCUMENTS

| JP | 2018-000460 A | 1/2018 |
| JP | 2018-117862 A | 8/2018 |
| WO | 2016/174839 A1 | 11/2016 |
| WO | 2016/194308 A1 | 12/2016 |
| WO | 2018/100755 A1 | 6/2018 |
| WO | 2018/168792 A1 | 9/2018 |

* cited by examiner

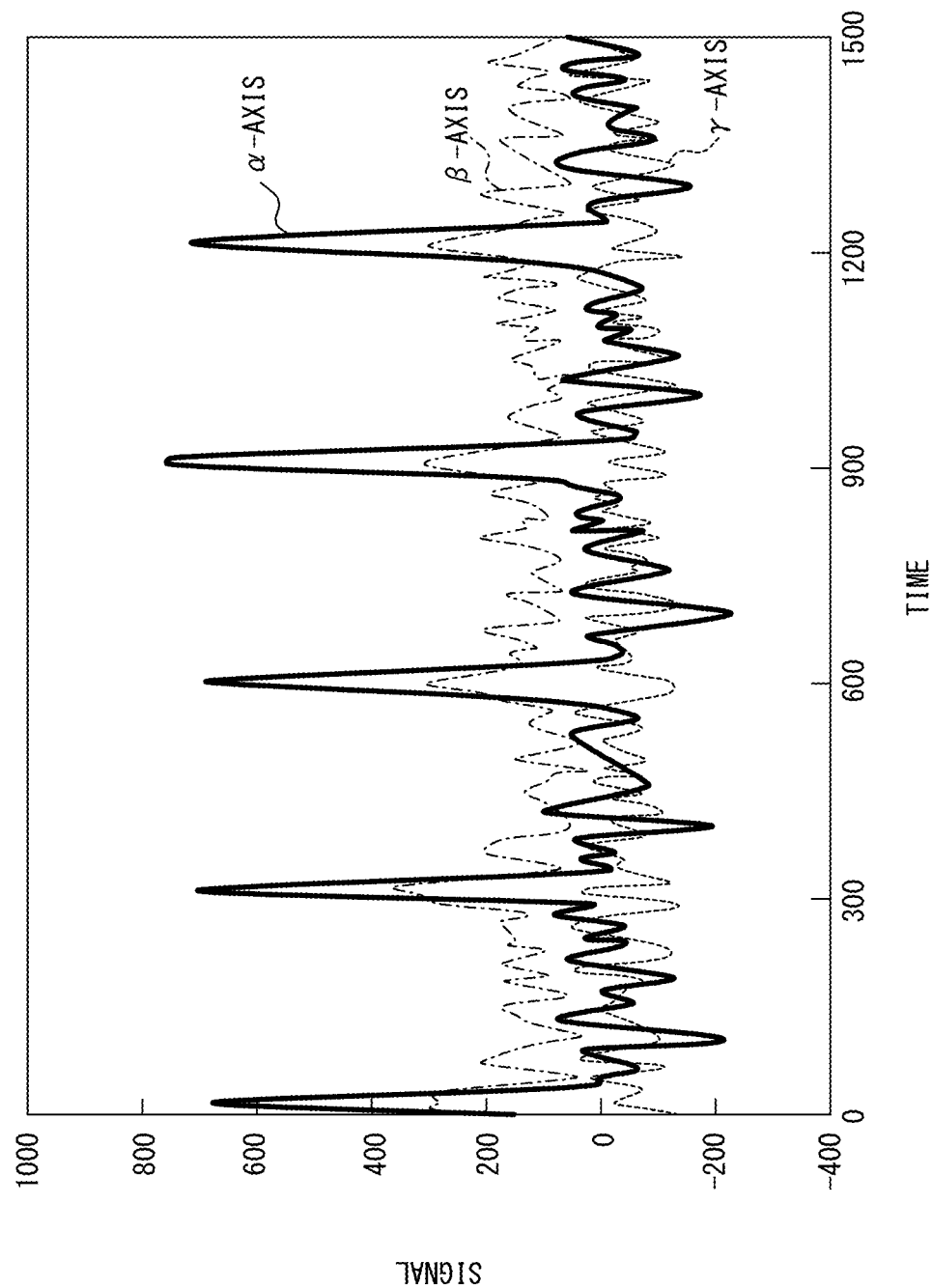

ELECTRONIC DEVICE

CROSS REFERENCE TO RELATED APPLICATION

This application claims the priority of Patent Application 2018-216644 filed in Japan on Nov. 19, 2018, and the entire disclosure of this previous application is hereby incorporated for reference.

TECHNICAL FIELD

The present disclosure relates to an electronic device.

BACKGROUND

Conventionally, electronic devices that are worn on the wrist of an examinee to acquire biological information of the examinee are known (see, for example, PLT 1 and PLT 2). In addition, an electronic device that facilitates stable estimation of the state of the carotid artery of the examinee has been disclosed (for example, PLT 3).

CITATION LIST

Patent Literature

PLT 1: WO2016174839A1
PLT 2: WO2016194308A1
PLT 3: JP2018000460A

SUMMARY

An embodiment of an electronic device comprises a sensor, a notifier, and a controller. The sensor is urged to a test part side of an examinee and is able to detect pulsation at the test part. The notifier notifies information for a position of the sensor at the test part. The controller controls the notifier to notify information for a position of the sensor at the test part based on pulsation at the test part detected by the sensor.

BRIEF DESCRIPTION OF THE DRAWINGS

In the accompanying drawings:

FIG. 18 is a diagram showing an example of a pulse wave acquired by the sensor.

DETAILED DESCRIPTION

First Embodiment

Depending on how an electronic device is worn, it may be difficult to acquire biological information accurately. If the electronic device is configured so that the biological information can be acquired more accurately, usefulness for the examinee is improved. An object of the present disclosure is to provide an electronic device whose usefulness can be improved. According to the present disclosure, it is possible to provide an electronic device whose usefulness can be improved. Hereinafter, the first embodiment will be described in detail with reference to the drawings.

Figure 1:
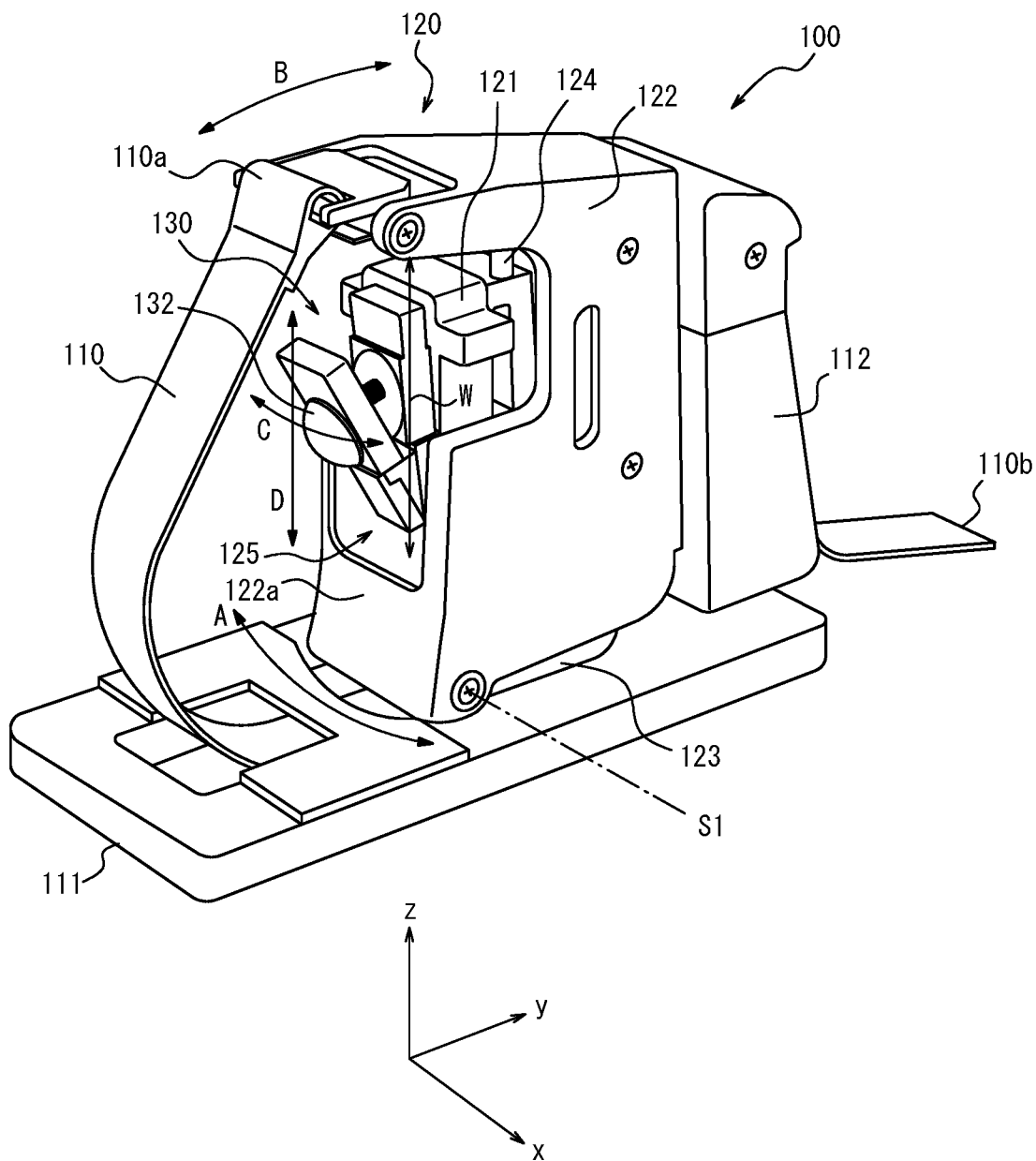
FIG. 1 is a schematic external perspective diagram of the electronic device according to the first embodiment.

FIG. 1 is a schematic external perspective diagram of an electronic device 100 according to the first embodiment. The electronic device 100 comprises a wearing part 110, a base 111, a fixing part 112 attached to the base 111, and a measuring part 120.

In the present embodiment, the base 111 is formed in a substantially rectangular flat plate shape. The present specification will be described, with the short side direction of the flat plate shaped base 111 as the x-axis direction, the long side direction of the flat plate shaped base 111 as the y-axis direction, and the orthogonal direction of the flat plate shaped base 111 as the z-axis direction, as shown in FIG. 1. Further, some parts of the electronic device 100 are configured to be movable as described in the present specification. When the directions relating to the electronic device 100 are described in the present specification, x, y, and z-axis directions in the state shown in FIG. 1 are indicated unless otherwise mentioned. Further, in the present specification, the z-axis positive direction is referred to as an upward direction, the z-axis negative direction is referred to as a downward direction, and the x-axis positive direction is referred to as a front of the electronic device 100.

The electronic device 100 measures the biological information of the examinee in a state where the examinee wears the electronic device 100 using the wearing part 110. The biological information measured by the electronic device 100 is a pulse wave of the examinee that can be measured by the measuring part 120. In the present embodiment, the electronic device 100 will be described below assuming that the electronic device 100 is worn to the examinee's wrist to acquire a pulse wave, as an example.

Figure 2:
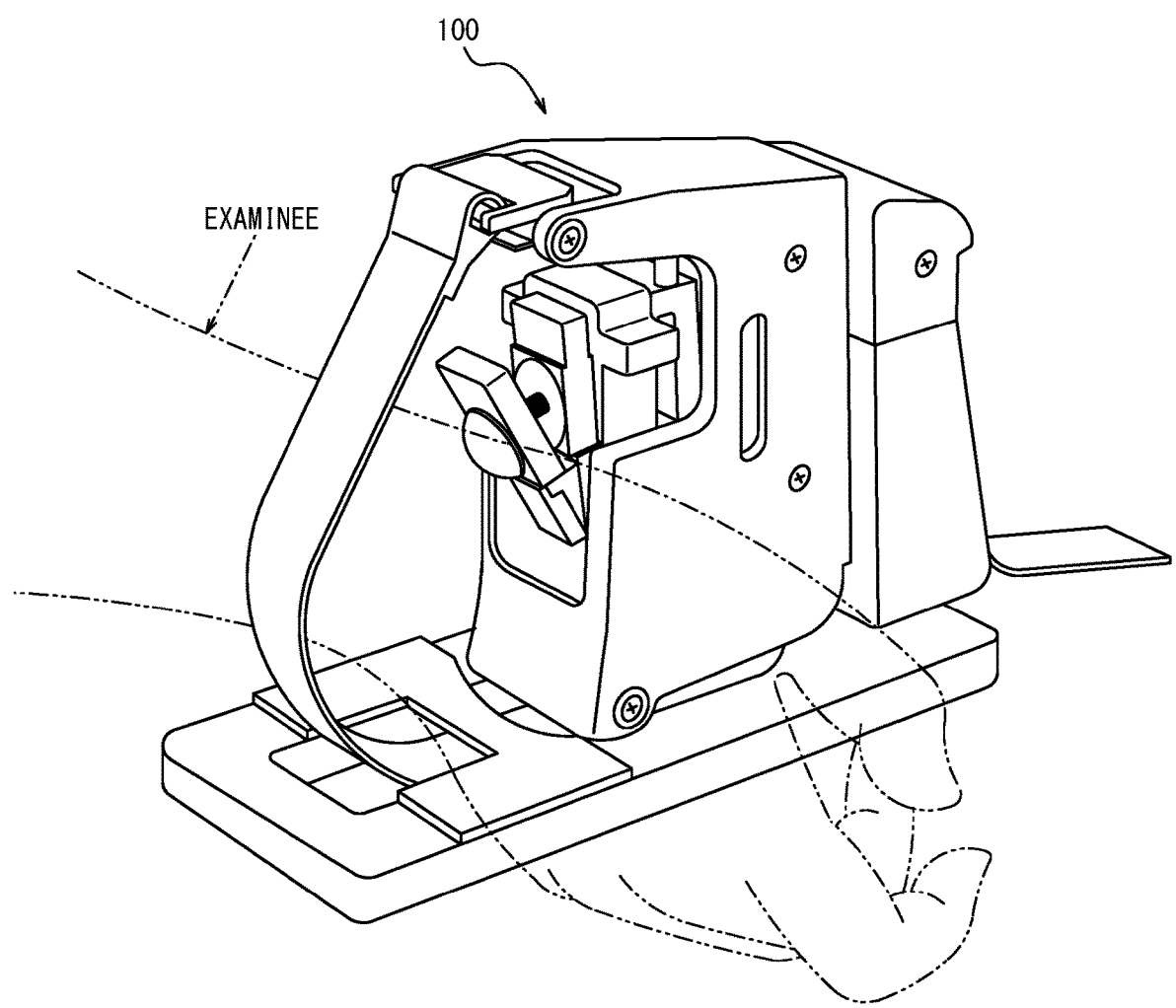
FIG. 2 is a schematic diagram showing a state in which the electronic device of FIG. 1 is worn.

FIG. 2 is a schematic diagram showing a state in which the examinee wears the electronic device 100 of FIG. 1. The examinee can wear the electronic device 100 as shown in FIG. 2 by passing his or her wrist through the space formed by the wearing part 110, the base 111, and the measuring part 120, and fixing the wrist with the wearing part 110. In the example shown in FIGS. 1 and 2, the examinee wears the electronic device 100 by passing his or her wrist through the space formed by the wearing part 110, the base 111, and the measuring part 120 along the x-axis direction and toward the positive x-axis direction. The examinee wears the electronic device 100 so that, for example, the pulse contact pad 132 of the measuring part 120 (described below) contacts the position where the ulnar or radial artery is located. The electronic device 100 measures the pulse wave of blood flowing through the ulnar artery or the radial artery on the examinee's wrist.

The measuring part 120 comprises a main body 121, an exterior 122, and a sensor 130. The sensor 130 is attached to the main body 121. The measuring part 120 is attached to the base 111 via a coupling part 123.

The coupling part 123 may be attached to the base 111 in a manner rotatable along the surface of the base 111. That is, in the example shown in FIG. 1, the coupling part 123, as indicated by the arrow A, may be attached to the base 111 in a manner rotatable on the xy surface with respect to the base 111.

In this case, the entire measuring part 120 attached to the base 111 via the coupling part 123 can rotate on the xy surface with respect to the base 111.

The exterior 122 is connected to the coupling part 123 on the axis S1 passing through the coupling part 123. The axis S1 is an axis extending in the x-axis direction. By connecting the exterior 122 to the coupling part 123 in this way, the exterior 122 is displaceable with respect to the coupling part 123 along a surface intersecting the xy surface in which the base 111 extends. That is, the exterior 122 can be inclined at a predetermined angle centering on the axis S1 on the xy surface on which the base 111 extends. For example, the exterior 122 can be displaced while riding on a surface having a predetermined inclination with respect to the xy surface such as the yz surface. In the present embodiment, as indicated by the arrow B in FIG. 1, the exterior 122 can be connected to the coupling part 123 in a manner rotatable, centering on the axis S1, on the yz surface orthogonal to the xy surface.

The exterior 122 has a contact surface 122a that comes into contact with the examinee's wrist in the wearing state of the electronic device 100. The exterior 122 may have an opening 125 on the contact surface 122a side. The exterior 122 may be configured to cover at least a part of the main body 121.

The exterior 122 may comprise a shaft 124 extending in the z-axis direction in the inner space. The main body 121 has a hole for passing the shaft 124, and the main body 121 is attached to the space inside the exterior 122 with the shaft 124 passed through the hole. That is, as indicated by the arrow C in FIG. 1, the main body 121 is attached to the exterior 122 in a manner rotatable, centering on the shaft 124, on the xy surface, with respect to the exterior 122. That is, the main body 121 is attached to the exterior 122 with respect to the exterior 122 in a manner rotatable along the xy surface which is the surface of the base 111. The main body 121, as indicated by the arrow D in FIG. 1, is attached to the exterior 122 in a manner displaceable vertically along the shaft 124, that is, along the z-axis direction, with respect to the exterior 122.

Figure 3:
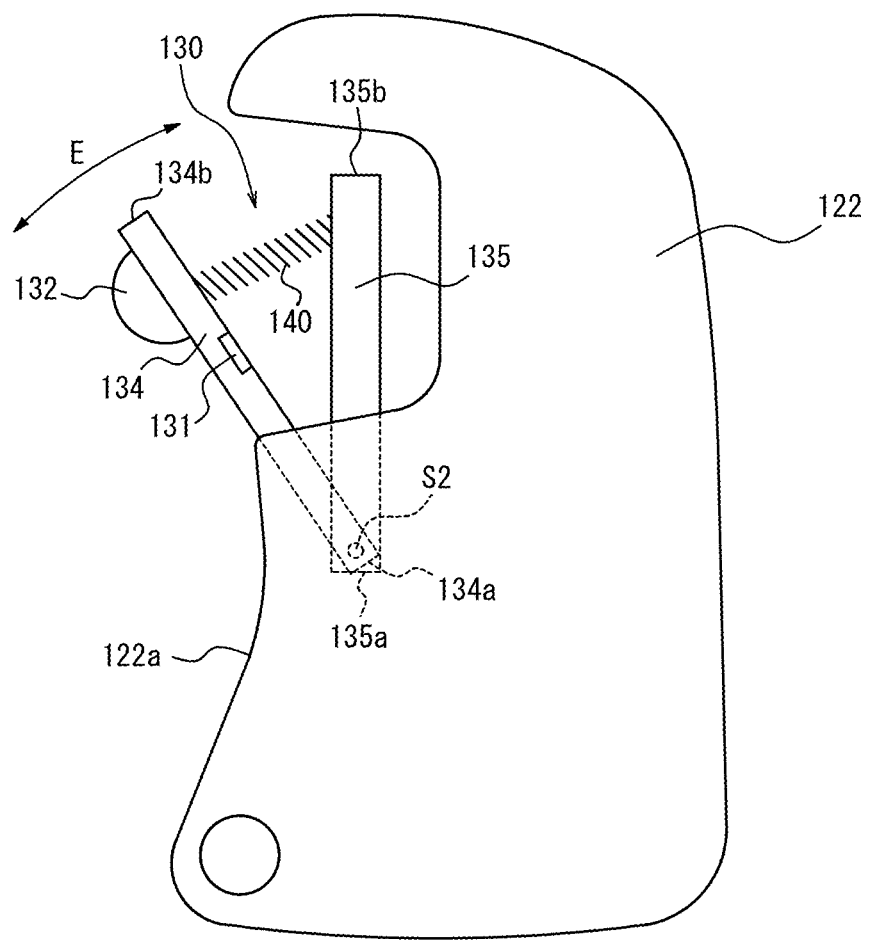
FIG. 3 is a schematic diagram showing an exterior and a sensor in a front view of the electronic device of FIG. 1.

The sensor 130 is attached to the main body 121. Here, the details of the sensor 130 will be described with reference to FIG. 3. FIG. 3 is a schematic diagram showing an exterior 122 and a sensor 130 in a front view of the electronic device 100. In FIG. 3, a portion of the sensor 130 that overlaps with the exterior 122 in the front view is represented by a dashed line.

The sensor 130 comprises a first arm 134 and a second arm 135. The second arm 135 is fixed to the main body 121. The lower one end 135*a* of the second arm 135 is connected to one end 134*a* of the first arm 134. As indicated by the arrow E in FIG. 3, the first arm 134 is connected to the second arm 135 in such a manner that one end 134*a* is the axis and the other end 134*b* side is rotatable on the yz surface.

The other end 134*b* side of the first arm 134 is connected to the other end 135*b* side on the upper side of the second arm 135 via an elastic body 140. The first arm 134 is supported by the second arm 135 in the state in which the other end 134*b* of the first arm 134 protrudes from the opening 125 of the exterior 122 to the contact surface 122*a* side when the elastic body 140 is not pressed. The elastic body 140 is, for example, a spring. However, the elastic body 140 is not limited to the spring, and can be any other elastic body such as resin or sponge.

A pulse contact pad 132 is connected to the other end 134*b* of the first arm 134. The pulse contact pad 132 is a part that comes into contact with the test part to be measured for the blood pulse wave of the examinee in the wearing state of the electronic device 100. In this embodiment, the pulse contact pad 132 contacts, for example, the position where the ulnar or radial artery is located. The pulse contact pad 132 may be made of a material that does not easily absorb changes in the body surface due to the pulse of the examinee. The pulse contact pad 132 may be made of a material that is less likely to cause pain to the examinee under contact conditions. For example, the pulse contact pad 132 may be made of a cloth bag or the like filled with beads. The pulse contact pad 132 may be detachably configured to, for example, the first arm 134. For example, the examinee attaches one pulse contact pad 132 to the first arm 134, fitting to the size and/or shape of his/her wrist, among the pulse contact pads 132 having a plurality of sizes and/or shapes. This allows the examinee to use the pulse contact pad 132 that is fitting to the size and/or shape of his or her own wrist.

The sensor 130 comprises an angular velocity sensor 131 that detects the displacement of the first arm 134. The angular velocity sensor 131 should be able to detect the angular displacement of the first arm 134. The sensor comprised by the sensor 130 is not limited to the angular velocity sensor 131, and may be, for example, an acceleration sensor, an angle sensor, or other motion sensor, or the sensor 130 may comprise these plurality of sensors.

As shown in FIG. 2, in this embodiment, in the wearing state of the electronic device 100, the pulse contact pad 132 is in contact with the skin on the radial artery, which is the artery on the thumb side of the right hand of the examinee. Due to the elastic force of the elastic body 140 arranged between the second arm 135 and the first arm 134, the pulse contact pad 132 arranged on the other end 134*b* side of the first arm 134 is in contact with the skin on the radial artery of the examinee. The first arm 134 is displaced in response to the movement of the radial artery that is pulsation of the examinee. The angular velocity sensor 131 acquires a pulse wave by detecting the displacement of the first arm 134. The pulse wave is a waveform of the volume time variation of the blood vessels caused by blood inflow, from the body surface.

As shown in FIG. 3, the first arm 134 is in a state in which the other end 134*b* protrudes from the opening 125 when the elastic body 140 is not pressed. When the electronic device 100 is worn to the examinee, the pulse contact pad 132 connected to the first arm 134 comes into contact with the skin on the radial artery of the examinee. In response to the pulsation, the elastic body 140 expands and contracts, and the pulse contact pad 132 is displaced. The elastic body 140 having a moderate modulus of elasticity is used so as not to interfere with pulsation and to expand and contract in response to pulsation. The opening width W of the opening 125 shown in FIG. 1 has a width sufficiently larger than the vessel diameter, that is the radial artery diameter in this embodiment. By providing the opening 125 in the exterior 122, the contact surface 122*a* of the exterior 122 does not press the radial artery in the wearing state of the electronic device 100. Therefore, the electronic device 100 can acquire a pulse wave with less noise, and the measurement accuracy is improved.

As shown in FIG. 1, the fixing part 112 is fixed to the base 111. The fixing part 112 may comprise a fixing mechanism for fixing the wearing part 110. The fixing part 112 may comprise various functional parts inside to be used for the electronic device 100 to perform pulse wave measurements. For example, the fixing part 112 may comprise a controller, a power supply, a storage, a communicator, a notifier, a circuit for operating them, a cable for connecting them, and the like, which will be described below.

The wearing part 110 is a mechanism used for the examinee to fix his or her wrist to the electronic device 100. In the example shown in FIG. 1, the wearing part 110 is an elongated band. In the example shown in FIG. 1, the wearing part 110 is arranged so that one end 110*a* is coupled to the upper end of the measuring part 120, and the other end 110*b* is located on the y-axis positive direction side through the inside of the base 111. For example, the examinee passes his or her right wrist through the space formed by the wearing part 110, the base 111, and the measuring part 120, and pulls the other end 110*b* of the wearing part 110 in the y-axis positive direction by the left hand while adjusting the pulse contact pad 132 so that the pulse contact pad 132 contacts the skin on the radial artery of the right wrist. The examinee pulls the other end 110*b* to such an extent that the right wrist is fixed to the electronic device 100, and in that state, the wearing part 110 is fixed by the fixing mechanism of the fixing part 112. In this way, the examinee can wear the electronic device 100 by one hand (left hand in this embodiment). Further, by fixing the wrist to the electronic device 100 using the wearing part 110, the wearing state of the electronic device 100 can be stabilized. As a result, because the positional relationship between the wrist and the electronic device 100 is less likely to change during the measurement, the pulse wave can be measured stably, and the measurement accuracy is improved.

Next, the movement of the movable part of the electronic device 100 in the wearing state of the electronic device 100 will be described.

When wearing the electronic device 100, the examinee passes his or her wrist through the space formed by the wearing part 110, the base 111, and the measuring part 120 along the x-axis direction as described above. At this time, the measuring part 120 is configured to be rotatable with respect to the base 111 in the direction indicated by the arrow A in FIG. 1. Therefore, the examinee can pass his or her wrist by rotating the measuring part 120 in the direction indicated by arrow A in FIG. 1. Because the measuring part 120 is configured to be rotatable in this way, the examinee can pass the wrist while appropriately changing the direction of the measuring part 120 according to the positional relationship between himself/herself and the electronic device 100. In this way, according to the electronic device 100, the examinee can easily wear the electronic device 100.

Figure 4:
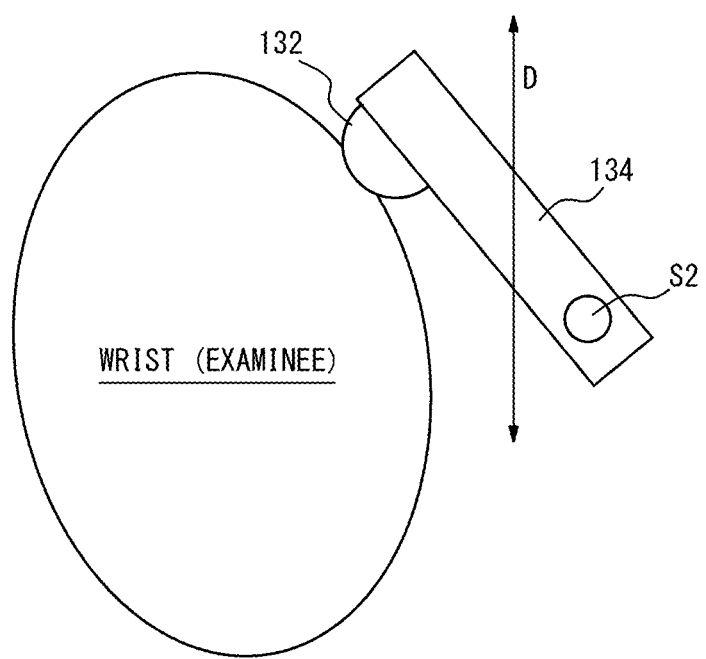
FIG. 4 is a schematic diagram showing the positional relationship between the examinee's wrist and the first arm of the sensor in front view.

The examinee passes his or her wrist through the space formed by the wearing part 110, the base 111, and the measuring part 120, and then brings the pulse contact pad 132 into contact with the skin on the radial artery of the wrist. Here, because the main body 121 is configured to be displaceable in the direction indicated by the arrow D in FIG. 1, as shown in FIG. 4, the first arm 134 of the sensor 130 coupled to the main body 121 can also be displaced in the direction indicated by the arrow D, that is the z-axis direction. Therefore, the examinee can displace the first arm 134 in the direction indicated by arrow D according to the size and thickness of his/her wrist so that the pulse contact pad 132 contacts the skin on the radial artery. The examinee can fix the main body 121 at the displaced position. In this way, according to the electronic device 100, it becomes easy to adjust the position of the sensor 130 to a position suitable for measurement. Therefore, according to the electronic device 100, the measurement accuracy is improved. In the example shown in FIG. 1, it has been described that the main body 121 can be displaced along the z-axis direction, but the main body 121 does not necessarily have to be configured to be displaceable along the z-axis direction. The main body 121 may be configured so that its position can be adjusted according to, for example, the size and thickness of the wrist. For example, the main body 121 may be configured to be displaceable along a direction intersecting the xy surface that is the surface of the base 111.

Here, when the pulse contact pad 132 is in contact with the skin on the radial artery in a direction orthogonal to the skin surface, the pulsation transmitted to the first arm 134 becomes large. That is, when the displacement direction of the pulse contact pad 132 (the direction indicated by the arrow E in FIG. 3) is the direction orthogonal to the skin surface, the pulsation transmitted to the first arm 134 becomes large, and the pulsation acquisition accuracy can be improved. In the electronic device 100 according to this embodiment, the main body 121 and the sensor 130 coupled to the main body 121 are configured to be rotatable, centering on the shaft 124, with respect to the exterior 122, as indicated by the arrow C in FIG. 1. Thereby, the examinee can adjust the direction of the sensor 130 so that the displacement direction of the pulse contact pad 132 becomes orthogonal to the skin surface. That is, the electronic device 100 can adjust the direction of the sensor 130 so that the displacement direction of the pulse contact pad 132 becomes orthogonal to the skin surface. In this way, according to the electronic device 100, the direction of the sensor 130 can be adjusted according to the shape of the examinee's wrist. Thereby, the change in the pulsation of the examinee is more easily transmitted to the first arm 134. Therefore, according to the electronic device 100, the measurement accuracy is improved.

Figure 5A:
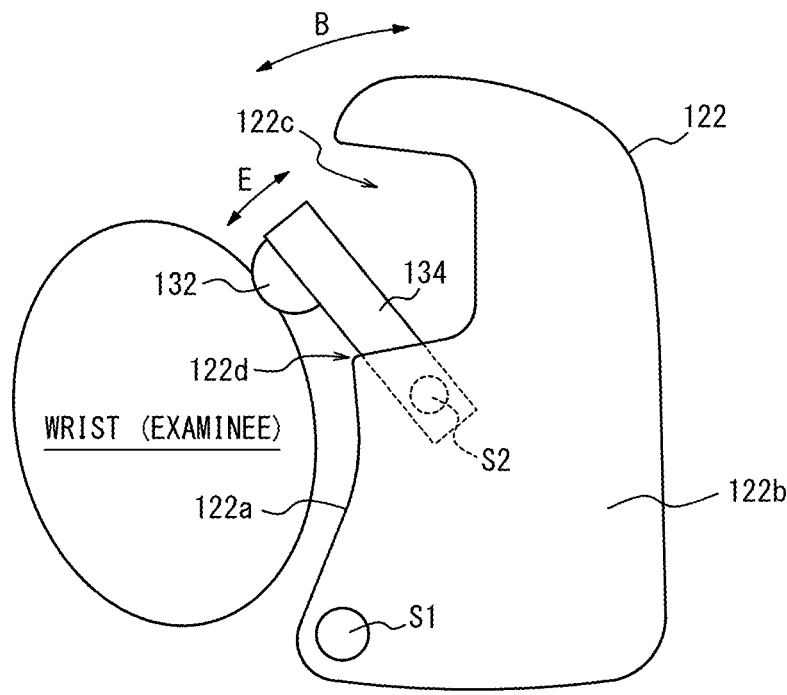
FIG. 5A is a schematic diagram showing the positional relationship between the examinee's wrist, the first arm of the sensor, and the exterior of the measuring part in front view.
Figure 5B:
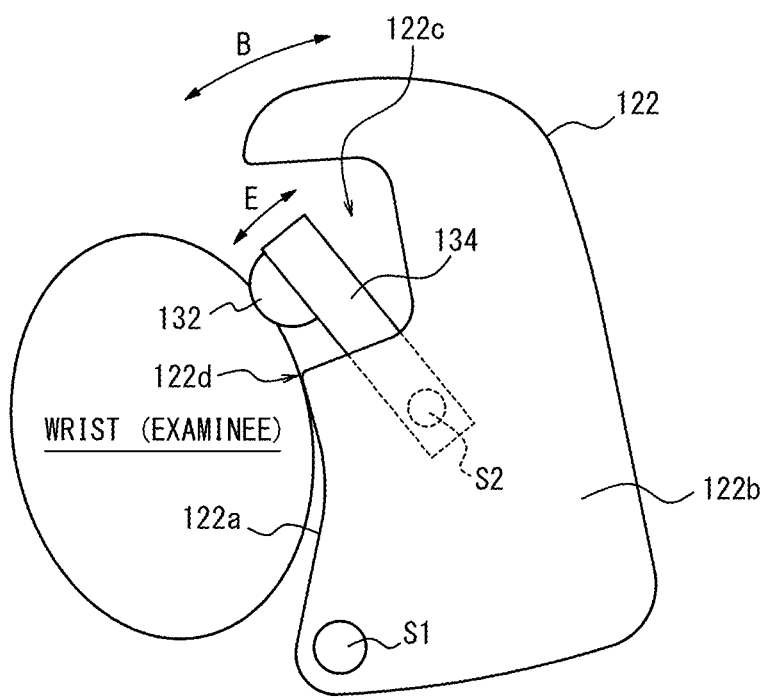
FIG. 5B is a schematic diagram showing the positional relationship between the examinee's wrist, the first arm of the sensor, and the exterior of the measuring part in front view.

The examinee brings the pulse contact pad 132 into contact with the skin on the radial artery of the wrist as shown in FIG. 5A, and then pulls the other end 110b of the wearing part 110 so as to fix the wrist to the electronic device 100. Here, because the exterior 122 is configured to be rotatable in the direction indicated by the arrow B in FIG. 1, when the examinee pulls the wearing part 110, the exterior 122 rotates centering on the axis S1, and the upper end side of the exterior 122 is displaced in the y-axis negative direction. That is, the upper end side of the exterior 122 is displaced in the y-axis negative direction as shown in FIG. 5B. Because the first arm 134 is connected to the second arm 135 via an elastic body 140, the upper end side of the exterior 122 displaces in the y-axis negative direction, and the elastic force of the elastic body 140 causes the pulse contact pad 132 to be urged to the radial artery side.

As a result, the pulse contact pad 132 can more reliably capture the change in pulsation. Therefore, according to the electronic device 100, the measurement accuracy is improved.

The rotation direction of the exterior 122 (direction indicated by the arrow B) and the rotation direction of the first arm 134 (direction indicated by the arrow E) may be substantially parallel. The closer the rotation direction of the exterior 122 and the rotation direction of the first arm 134 are to parallel, the more efficiently the elastic force of the elastic body 140 is applied to the first arm 134 when the upper end side of the exterior 122 is displaced in the y-axis negative direction. The range where the rotation direction of the exterior 122 and the rotation direction of the first arm 134 are substantially parallel includes the range where the elastic force of the elastic body 140 is applied to the first arm 134 when the upper end side of the exterior 122 is displaced in the y-axis negative direction.

Here, the front side surface 122b of the exterior 122 shown in FIGS. 5A and 5B is substantially rectangular shape, long in the vertical direction. The surface 122b has a notch 122c on the upper end side on the side on the y-axis negative side. Thanks to the notch 122c, even if the upper end side of the exterior 122 is displaced in the y-axis negative direction as shown in FIG. 5B, the surface 122b is unlikely to come into contact with the skin on the radial artery. Therefore, it becomes easier to prevent the pulsation of the radial artery from being hindered by contact with the surface 122b.

Further, as shown in FIG. 5B, when the upper end side of the exterior 122 is displaced in the y-axis negative direction, the lower end 122d of the notch 122c comes into contact the skin at a position different from that of the radial artery of the wrist. When the end 122d contacts the wrist, the exterior 122 becomes no longer displaced in the y-axis negative direction beyond the contact position. Therefore, the end 122d can prevent the exterior 122 from being displaced beyond a predetermined position. If the exterior 122 is displaced beyond a predetermined position in the y-axis negative direction, the first arm 134 will be strongly urged to the radial artery side by the elastic force of the elastic body 140. This can easily hinder the pulsation of the radial artery. In the electronic device 100 according to the present embodiment, because the exterior 122 has the end 122d, it is possible to prevent excessive pressure from being applied to the radial artery from the first arm 134. And as a result, the pulsation of the radial artery is less likely to be hindered. In this way, the end portion 122d functions as a stopper that limits the displaceable range of the exterior 122.

In the present embodiment, the rotation axis S2 of the first arm 134 may be arranged at a position separated from the end on the y-axis negative side of the surface 122b as shown in FIGS. 5A and 5B. When the rotation axis S2 is arranged near the end of the surface 122b on the y-axis negative side, due to the first arm 134 coming into contact with the examinee's wrist, the change due to the pulsation of the radial artery may not be accurately captured. By arranging the rotation shaft S2 at a position separated from the end of the surface 122b on the y-axis negative direction side, the possibility that the first arm 134 comes into contact with the wrist can be reduced. This makes it easier for the first arm 134 to more accurately capture changes in the pulsation.

The examinee wears the electronic device 100 on the wrist by pulling the other end 110b of the wearing part 110 and fixing the wearing part 110 in that state by the fixing mechanism of the fixing part 112. While worn on the wrist in this way, the electronic device 100 measures the pulse wave of the examinee by the first arm 134 changing in the direction indicated by the arrow E in response to the change in the pulsation.

Figure 6:
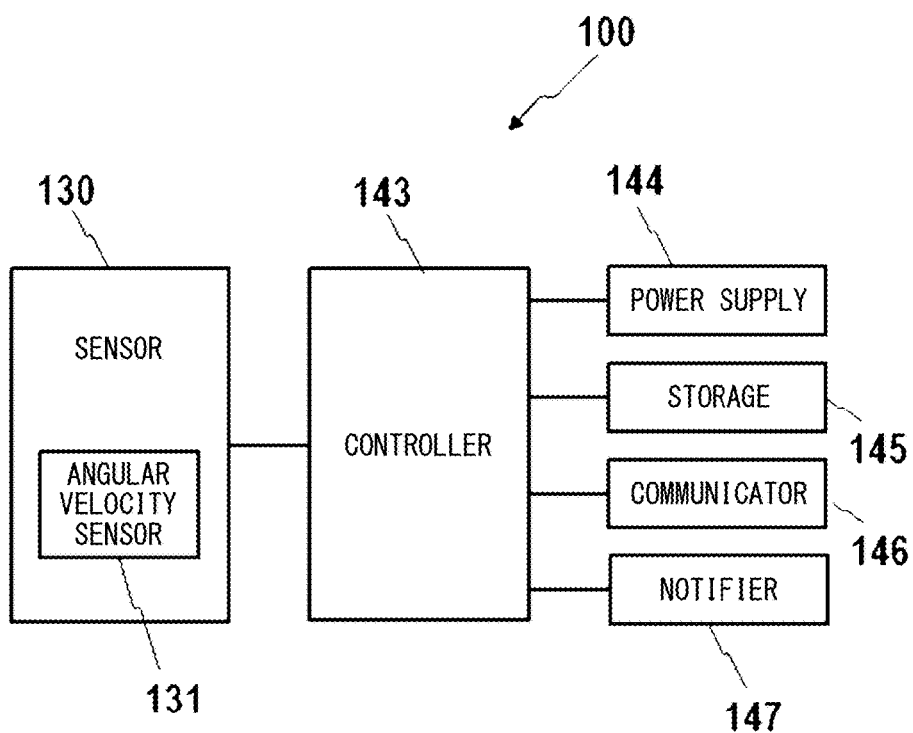
FIG. 6 is a functional block diagram showing a schematic configuration of the electronic device of FIG. 1.

FIG. 6 is a functional block diagram showing a schematic configuration of the electronic device 100. The electronic device 100 comprises a sensor 130, a controller 143, a power supply 144, a storage 145, a communicator 146, and a notifier 147. In the present embodiment, the controller 143, the power supply 144, the storage 145, the communicator 146, and the notifier 147 are included inside, for example, the fixing part 112.

The sensor 130 includes the angular velocity sensor 131, detects the pulsation from the test part, and acquires the pulse wave.

The controller 143 is a processor configured to control and manage the entire electronic device 100, including each functional block of the electronic device 100. Further, the controller 143 is a processor configured to calculate an index based on the pulse wave propagation phenomenon from the acquired pulse wave. The controller 143 consists of a processor such as a CPU (Central Processing Unit) configured to execute a program that specifies control procedures and a program that calculates indices based on pulse wave propagation phenomena, and such program is stored in a storage medium such as a storage 145. In addition, the controller 143 estimates the state of the examinee regarding glucose metabolism, lipid metabolism, and the like based on the calculated index. The controller 143 notifies the notifier 147 of the data.

The power supply 144 comprises, for example, a lithium ion battery and a control circuit for charging and discharging the lithium ion battery, and supplies electric power to the entire electronic device 100.

The storage 145 stores programs and data. The storage 145 may include any non-transitory storage medium such as a semiconductor storage medium and a magnetic storage medium. The storage 145 may include a plurality types of storage medium. The storage 145 may include a combination of a portable storage medium such as a memory card, an optical disk, or a magneto-optical disk, and a reading device for the storage medium. The storage 145 may include a storage device used as a temporary storage area such as a RAM (Random Access Memory). The storage 145 stores various information and/or programs for operating the electronic device 100, and also functions as a work memory. The storage 145 may store, for example, the measurement results of the pulse waves acquired by the sensor 130.

The communicator 146 transmits and receives various data by performing wired communication or wireless communication with an external device. The communicator 146, for example, communicates with an external device that stores the biological information of the examinee so as to manage his or her health status, and transmits measurement results of the pulse wave measured by the electronic device 100 and/or his or her health status estimated by the electronic device 100 to the external device.

The notifier 147 notifies information by sound, vibration, images, or the like. The notifier 147 may comprise a speaker, an oscillator, and display devices such as a liquid crystal display (LCD: liquid crystal display), an organic EL display (OELD: Organic Electro-Luminescence Display), an inorganic EL display (IELD: inorganic Electro-Luminescence Display), or the like. In the present embodiment, the notifier 147 notifies, for example, the state of glucose metabolism or lipid metabolism of the examinee.

Figure 7:
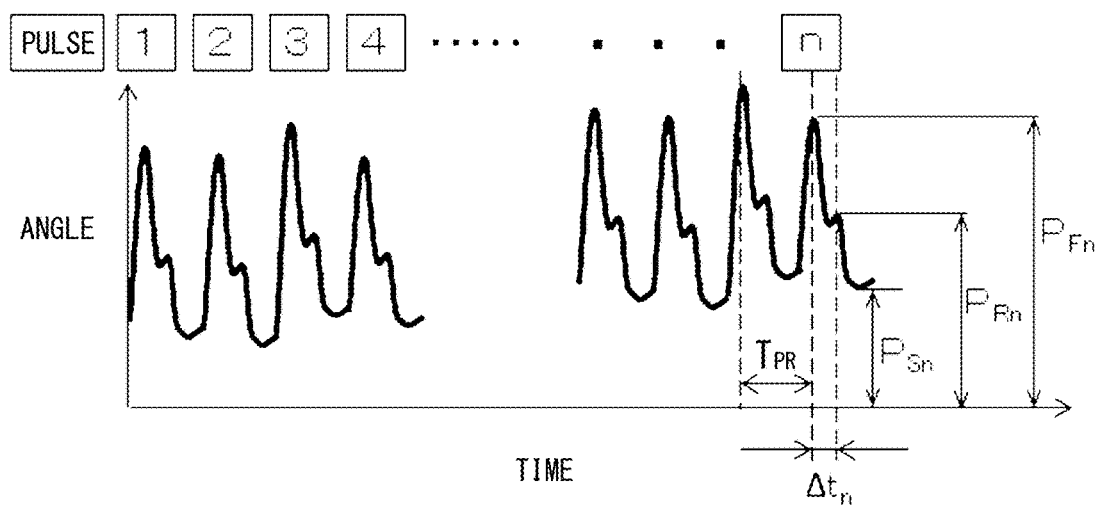
FIG. 7 is a diagram showing an example of a pulse wave acquired by the sensor.

FIG. 7 is a diagram showing an example of a pulse wave acquired on the wrist using the electronic device 100. FIG. 7 shows a case where the angular velocity sensor 131 is used as a pulsation detecting means. FIG. 7 shows the time integration of the angular velocity acquired by the angular velocity sensor 131, where the horizontal axis represents time and the vertical axis represents angle. Because the acquired pulse wave may contain noise caused by, for example, the body movement of the examinee, correction by a filter to remove the DC (Direct Current) component may be performed and only the pulsation component may be extracted.

A method of calculating a pulse wave-based index from the acquired pulse wave will be described with reference to FIG. 7. Pulse wave propagation is a phenomenon in which the pulsation of blood extruded from the heart travels through the walls of arteries and/or blood. The pulsation caused by the blood extruded from the heart reaches the periphery of the limbs as forward waves, and some of it is reflected at the branch part of the blood vessel, the change part of the blood vessel diameter and the like, and returns as the reflected waves. A pulse wavebased indices are, for example, the pulse wave velocity PWV (Pulse Wave Velocity) of the forward wave, the magnitude $P_R$ of the reflected wave of the pulse wave, the time difference $\Delta t$ between the forward wave and the reflected wave of the pulse wave, the AI (Augmentation Index) represented by the ratio of the magnitudes of the forward wave and the reflected wave of the pulse wave or the like.

The pulse wave shown in FIG. 7 shows n times of pulses of the user, where n is an integer greater than or equal to one. The pulse wave is a synthetic wave consisting of the superposition of the forward wave generated by the ejection of blood from the heart, and the reflected wave generated from the branch part of the blood vessel and/or the change part of the blood vessel diameter. In FIG. 7, the magnitude of the pulse wave peak due to the forward wave for each pulse is indicated by $P_{Fn}$, the magnitude of the pulse wave peak due to the reflected wave for each pulse by $P_{Rn}$, and the minimum pulse wave value for each pulse by Psa. In addition, in FIG. 7, the interval between pulse peaks is indicated by $T_{PR}$.

A pulse wavebased index is a quantification of the information acquired from the pulse wave. For example, PWV, which is one of the indices based on the pulse wave, is calculated based on the propagation time difference of the pulse wave measured at two test parts such as the upper arm and the ankle, and the distance between the two points. Specifically, the PWV is acquired by synchronizing the pulse waves (for example, the upper arm and the ankle) at two points of the artery, and dividing the difference in distance between the two points (L) by the time difference between the pulse waves at the two points (PTT). For example, the magnitude of the reflected wave, $P_R$, which is one of the pulse wavebased indices, may be acquired by calculating $P_{Rn}$, that is the magnitude of the peak of the pulse wave due to the reflected wave, or by calculating $P_{Rave}$, that is an average of n times of pulse waves. For example, the time difference $\Delta t$ between the forward wave and the reflected wave of the pulse wave, that is one of the pulse wavebased indices, may be calculated as the time difference $\Delta t_n$ in a predetermined pulse, or as the $\Delta t_{ave}$ by averaging the time differences of n times of pulse waves. For example, AI, that is one of the pulse wavebased indices, is obtained by dividing the magnitude of the reflected wave by the magnitude of the forward wave, and is represented by $AI_n=(P_{Rn}-P_{Sn})/(P_{Fn}-P_{Sn})$. $AI_n$ is the AI for each pulse. AI may be used as a pulse wavebased index, for example, by measuring pulse waves for several seconds and calculating the average value $AI_{ave}$ of $AI_n$ (n=1 to n integers) for each pulse.

Because the pulse wave velocity PWV, the magnitude $P_R$ of the reflected wave, the time difference $\Delta t$ between the forward wave and the reflected wave, and the AI change depending on the hardness of the blood vessel wall, they can be used to estimate the state of arteriosclerosis. For example, if the blood vessel wall is hard, the pulse wave velocity PWV increases. For example, if the blood vessel wall is hard, the magnitude $P_R$ of the reflected wave becomes large. For example, if the blood vessel wall is hard, the time difference $\Delta t$ between the forward wave and the reflected wave becomes small. For example, if the blood vessel wall is hard, the AI becomes large. Further, the electronic device 100 can estimate the state of arteriosclerosis and the fluidity (viscosity) of blood by using these pulse wavebased indices. In particular, the electronic device 100 can estimate changes in blood fluidity from changes in pulse wavebased indices acquired at the same test part of the same examinee and over a period of time (for example, within a few days) when the state of arteriosclerosis is almost unchanged Here, the fluidity of blood indicates the ease of blood flow. For example, when the fluidity of blood is low, the pulse wave velocity PWV becomes small. For example, when the fluidity of blood is low, the magnitude $P_R$ of the reflected wave becomes small. For example, when the blood fluidity is low, the time difference $\Delta t$ between the forward wave and the reflected wave becomes large. For example, if blood fluidity is low, AI becomes low.

In this embodiment, as an example of pulse wavebased indices, examples are shown in which the electronic device 100 calculates the pulse wave velocity PWV, the magnitude $P_R$ of the reflected wave, the time difference $\Delta t$ between the forward wave and the reflected wave, and AI. However, the pulse wave based indices are not limited to these. For example, the electronic device 100 may use the posterior systolic blood pressure as a pulse wave-based index.

Figure 8:
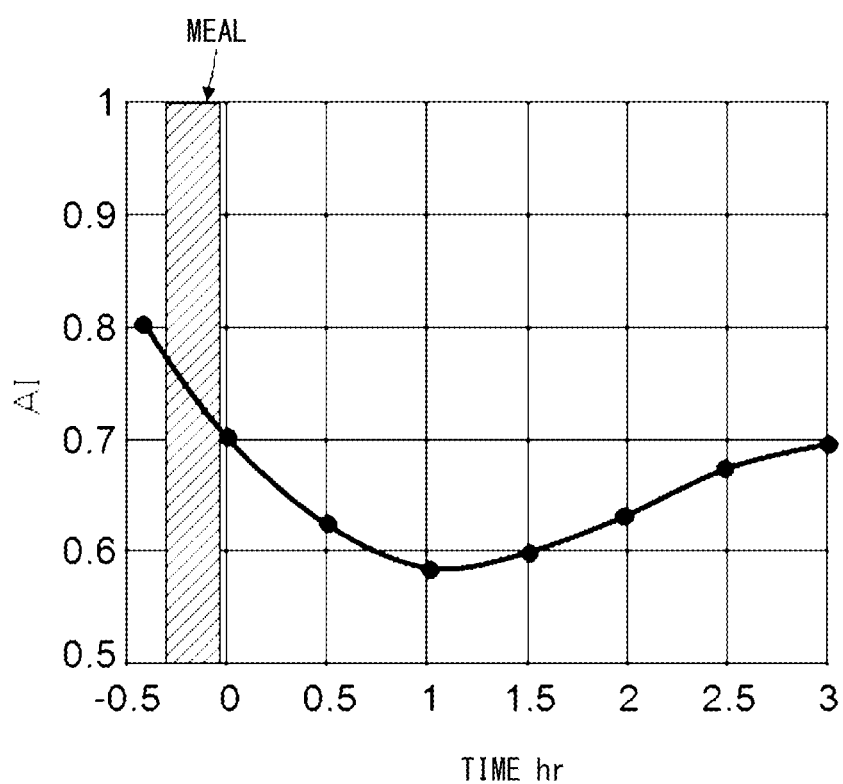
FIG. 8 is a diagram showing the time variation of the calculated AI.

FIG. 8 is a diagram showing the calculated time variation of AI. In this embodiment, the pulse wave was acquired for about 5 seconds using an electronic device 100 equipped with an angular velocity sensor 131. The controller 143 calculated the AI for each pulse from the acquired pulse wave, and further calculated the average value $AI_{ave}$ of these. In the present embodiment, the electronic device 100 acquired pulse waves at a plurality of timings before and after a meal, and calculated an average value of AI (hereinafter referred to as AI) as an example of acquired pulse wave-based indices. The horizontal axis of FIG. 8 shows the passage of time with the first measurement time after a meal as 0. The vertical axis of FIG. 8 shows the AI calculated from the pulse wave acquired at that time. The pulse wave was obtained on the radial artery in the state when the examinee was at rest.

The electronic device 100 acquired pulse waves before meals, immediately after meals, and every 30 minutes after meals, and calculated a plurality of AIs based on the respective pulse waves. The AI calculated from the pulse waves acquired before meals was about 0.8. Compared to before the meal, the AI became smaller immediately after the meal, and the AI reached its smallest extreme value about 1 hour after the meal. AI gradually increased until the measurement was completed 3 hours after the meal.

The electronic device 100 can estimate the change in blood fluidity from the calculated change in AI. For example, when red blood cells, white blood cells, and platelets in blood are solidified into dumplings or the greater the adhesive strength, the less fluid the blood becomes. For example, the smaller the water content of the plasma in the blood, the less fluid the blood becomes. These changes in blood fluidity vary depending on, for example, the glycolipid status described below and/or the health condition of the examinee such as heat stroke, dehydration, and hypothermia. Before the health condition of the examinee becomes serious, the examinee can know the change in the fluidity of his/her blood by using the electronic device 100 according to the present embodiment. From the change in AI before and after meals shown in FIG. 8, it can be estimated that the blood fluidity became low after the meal, the blood fluidity became the lowest about 1 hour after the meal, and then the blood fluidity gradually increased. The electronic device 100 may notify the state of the low blood fluidity by describing as "muddy" and the state of the high blood fluidity as "smooth". For example, the electronic device 100 may determine "muddy" or "smooth" based on the average value of AI at the actual age of the examinee. The electronic device 100 may determine that the state of the blood fluidity is "smooth" if the calculated AI is larger than the average value, and "muddy" if the calculated AI is smaller than the average value. The electronic device 100 may, for example, determine "muddy" and "smooth" based on the AI before the meal. The electronic device 100 may estimate the degree of "muddy" by comparing the AI after a meal with the AI before a meal. The electronic device 100 can use an AI before a meal, that is, an AI on an empty stomach as an index of the blood vessel age (Blood vessel stiffness) of the examinee, for example. If, for example, the electronic device 100 calculates the amount of change in the calculated AI based on the AI before the meal of the examinee, that is, AI on an empty stomach, the electronic device 100 can estimate the change in blood fluidity more accurately because it can reduce the estimation error due to the examinees vascular age (blood vessel stiffness).

Figure 9:
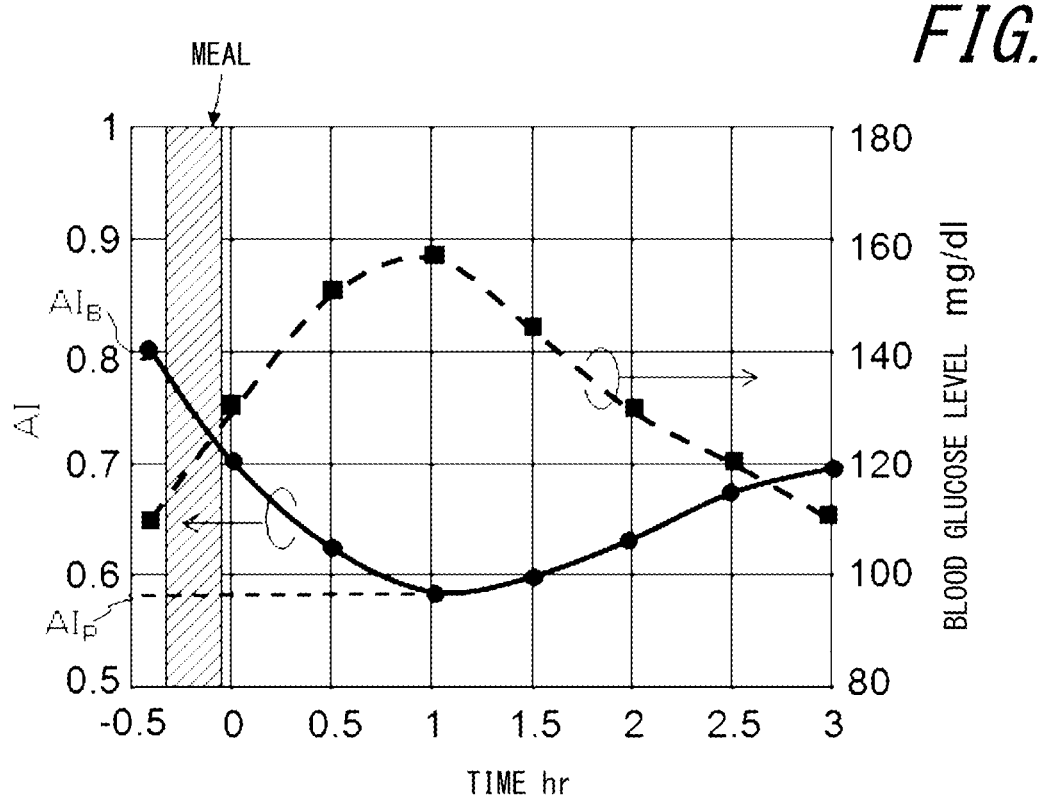
FIG. 9 is a diagram showing measurement results of the calculated AI and blood glucose level.

FIG. 9 is a diagram showing the measurement results of the calculated AI and blood glucose level. The method of acquiring the pulse wave and the method of calculating the AI are the same as those in the embodiment shown in FIG. 8. The right vertical axis of FIG. 9 shows the blood glucose level in blood, and the left vertical axis shows the calculated AI. The solid line in FIG. 9 shows the AI calculated from the acquired pulse wave, and the dotted line shows the measured blood glucose level. The blood glucose level was measured immediately after the pulse wave had been acquired. The blood glucose level was measured using a blood glucose meter "medisafe fit" manufactured by Terumo corporation. The blood glucose level immediately after a meal is increased by about 20 mg/dl as compared with the blood glucose level before a meal. About 1 hour after a meal, the blood glucose level reached the maximum extreme value. After that, the blood glucose level gradually decreased until the measurement was completed, and became almost the same as the blood glucose level before the meal, about 3 hours after the meal.

As shown in FIG. 9, the blood glucose level before and after a meal has a negative correlation with the AI calculated from the pulse wave. After a meal, the blood glucose level increases and insulin is secreted. Blood flow increases due to the vasodilatory effect of insulin secretion and the increase in osmotic pressure caused by elevated blood glucose levels. As a result of these factors, blood vessels dilate. AI decreases due to dilation of blood vessels. In addition, when the blood glucose level becomes high, the sugar in the blood may cause red blood cells and platelets to clump together in a dumpling shape or the adhesive strength increases, and as a result, the fluidity of blood may decrease. When blood fluidity decreases, the pulse wave velocity PWV may decrease. As the pulse wave velocity PWV decreases, the time difference $\Delta t$ between the forward wave and the reflected wave may increase. When the time difference $\Delta t$ between the forward wave and the reflected wave becomes large, the magnitude $P_R$ of the reflected wave may become smaller than the magnitude $P_F$ of the forward wave. When the magnitude $P_R$ of the reflected wave becomes smaller than the magnitude $P_F$ of the forward wave, the AI may become smaller. Because the AI within a few hours after a meal (3 hours in the present embodiment) correlates with the blood glucose level, the fluctuation of the blood glucose level of the examinee can be estimated from the fluctuation of the AI. Further, if the blood glucose level of the examinee is measured in advance and the correlation with the AI is acquired, the electronic device 100 can estimate the blood glucose level of the examinee from the calculated AI.

Based on the time of occurrence of $AI_P$, which is the minimum extreme value of AI detected first after a meal, the electronic device 100 can estimate the state of glucose metabolism of the examinee. The electronic device 100 estimates, for example, a blood glucose level as a state of glucose metabolism. As an estimation example of the state of glucose metabolism, for example, when the minimum extreme value $AI_P$ of AI detected first after a meal is detected after a predetermined time or more (for example, about 1.5 hours or more after a meal), the electronic device 100 can estimate that the examinee has an abnormal glucose metabolism (diabetic patient).

Based on the difference between $AI_B$, which is AI before meals, and $AI_P$, which is the minimum extreme value of AI detected first after meals ($AI_B$–$AI_P$), the electronic device 100 estimates the state of glucose metabolism of the examinee. As an estimation example of the state of glucose metabolism, for example, when ($AI_B$–$AI_P$) is a predetermined value or more (for example, 0.5 or more), the examinee can be estimated to have abnormal glucose metabolism (patient with postprandial hyperglycemia).

Figure 10:
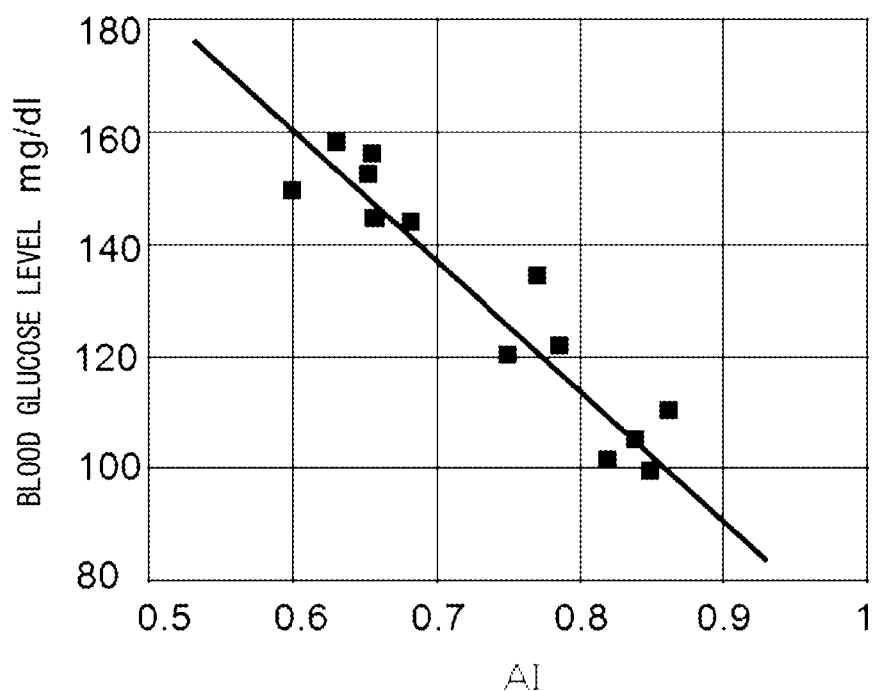
FIG. 10 is a diagram showing the relationship between the calculated AI and the blood glucose level.

FIG. 10 shows the relationship between the calculated AI and the blood glucose level. The calculated AI and blood glucose levels are those obtained within one hour after a meal, when blood glucose levels fluctuate significantly. The data in FIG. 10 includes data after several different meals for the same examinee. As shown in FIG. 10, the calculated AI and the blood glucose level showed a negative correlation. The correlation coefficient between the calculated AI and the blood glucose level was 0.9 or higher, indicating a very high correlation. For example, if the correlation between the calculated AI and the blood glucose level as shown in FIG. 10 is obtained for each examinee in advance, the electronic device 100 can also estimate the blood glucose level of the examinee from the calculated AI.

Figure 11:
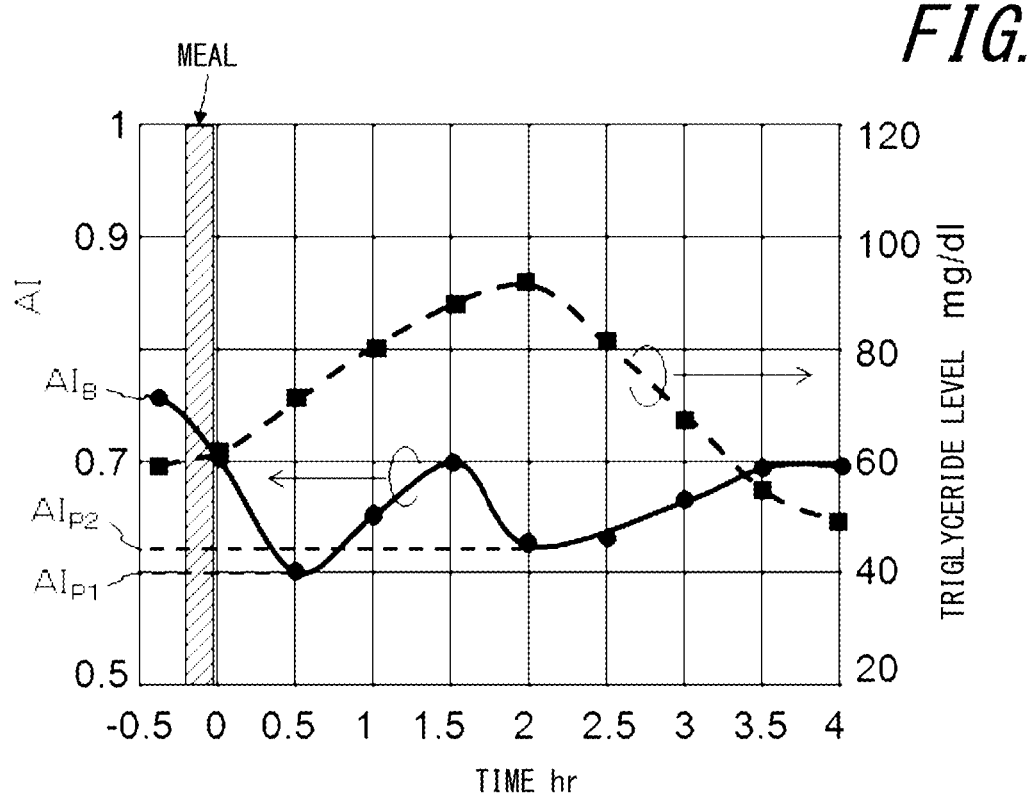
FIG. 11 is a diagram showing the measurement results of the calculated AI and triglyceride level.

FIG. 11 is a diagram showing the measurement results of the calculated AI and triglyceride level. The method of acquiring the pulse wave and the method of calculating the AI are the same as those in the embodiment shown in FIG. 8. The right vertical axis of FIG. 11 shows the triglyceride level in blood, and the left vertical axis shows AI. The solid line in FIG. 11 shows the AI calculated from the acquired pulse wave, and the dotted line shows the measured triglyceride level. The triglyceride level was measured immediately after the pulse wave had been acquired. The triglyceride level was measured using a lipid measuring device "Pocket Lipid" manufactured by Techno Medica. The maximum extreme value of triglyceride level after meal is increased by about 30 mg/dl as compared with the triglyceride level before meal. Approximately 2 hours after a meal, triglyceride reached its maximum extreme value. After that, the triglyceride level gradually decreased until the measurement was completed, and became almost the same as the triglyceride level before the meal about 3.5 hours after the meal.

In contrast, for the calculated minimum extreme value of AI, the first minimum extreme value $AI_{P1}$ was detected about 30 minutes after the meal, and the second minimum extreme $AI_{P2}$ was detected about 2 hours after the meal. It can be estimated that the first minimum extreme value $AI_{P1}$ detected about 30 minutes after a meal is due to the influence of the blood glucose level after a meal described above. The second minimum extreme value, $AI_{P2}$, detected about 2 hours after the meal, is almost identical in its occurrence time to the maximum extreme value of triglycerides detected about 2 hours after the meal. From this, it can be estimated that the second minimum extreme value $AI_{P2}$ detected after a predetermined time from the meal is due to the influence of triglyceride. It was found that the triglyceride level before and after a meal has a negative correlation with the AI calculated from the pulse wave, as in the blood glucose level. In particular, $AI_{P2}$, which is the minimum extreme value of AI, detected after a predetermined time from a meal (after about 1.5 hours in the embodiment), is correlated with the triglyceride value. Therefore, the fluctuation of the triglyceride value of the examinee can be estimated based on the fluctuation of AI. Further, if the triglyceride level of the examinee is measured in advance and the correlation with the AI is obtained, the electronic device 100 can estimate the triglyceride level of the examinee from the calculated AI.

Based on the time of occurrence of the second minimum extreme value $AI_{P2}$ detected after a predetermined time after a meal, the electronic device 100 can estimate the state of lipid metabolism of the examinee. The electronic device 100 estimates, for example, a lipid value as a state of lipid metabolism. As an estimation example of the state of lipid metabolism, for example, when the second minimum extreme value $AI_{P2}$ is detected after a predetermined time or more (for example, 4 hours or more) from a meal, electronic device 100 can estimate that the examinee has abnormal lipid metabolism (hyperlipidemia patient).

Based on the difference ($AI_B$–$AI_{P2}$) between $AI_B$, which is AI before a meal, and $AI_{P2}$, which is the second minimum extreme value detected after a predetermined time from a meal, the electronic device 100 can estimate the state of lipid metabolism of the examinee. As an estimation example of dyslipidemia, for example, when $(AI_B-AI_{P2})$ is 0.5 or more, the electronic device 100 can estimate that the examinee has dyslipidemia (patient with postprandial hyperlipidemia).

Further, from the measurement results shown in FIGS. 9 to 11, the electronic device 100 according to the present embodiment can estimate the state of glucose metabolism of an examinee based on the first minimum extreme value $AI_{P1}$ detected earliest after a meal and its occurrence time. Further, the electronic device 100 according to the present embodiment can estimate the state of lipid metabolism of the examinee based on the second minimum extreme value $AI_{P2}$ detected after a predetermined time after the first minimum extreme value $AI_{P1}$ and its occurrence time.

In the embodiment, the case of triglyceride has been described as an estimation example of lipid metabolism, but the estimation of lipid metabolism is not limited to triglyceride. The lipid value estimated by the electronic device 100 includes, for example, total cholesterol, good (HDL: High Density Lipoprotein) cholesterol, bad (LDL: Low Density Lipoprotein) cholesterol, and the like. These lipid levels also show the same tendency as in the case of triglycerides described above.

Figure 12:
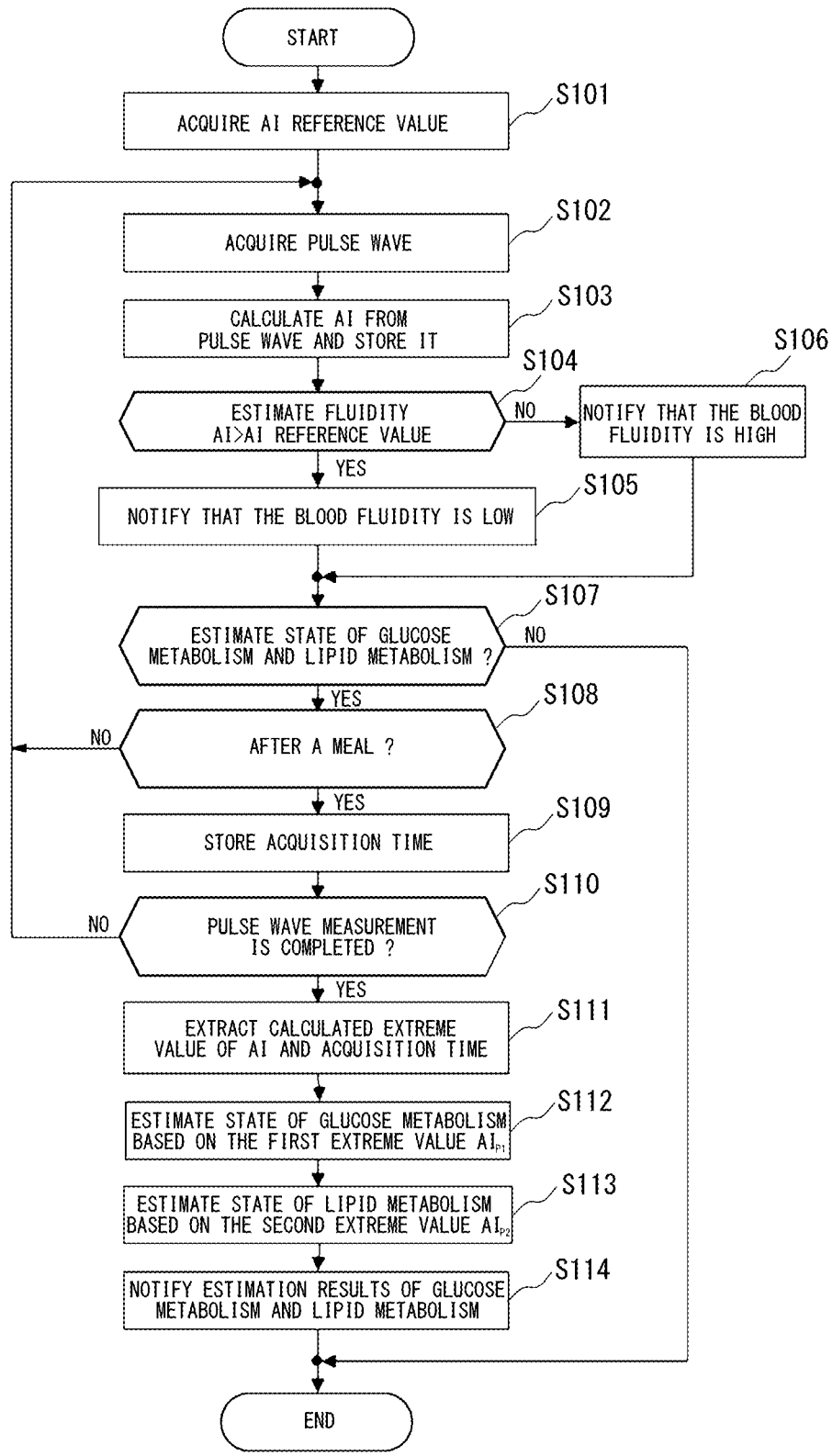
FIG. 12 is a flowchart showing a procedure for estimating blood fluidity and the state of glucose and lipid metabolism.

FIG. 12 is a flow chart showing a procedure for estimating the fluidity of blood and the states of glucose metabolism and lipid metabolism based on AI. With reference to FIG. 12, the flow of estimating the fluidity of blood and the states of glucose metabolism and lipid metabolism by the electronic device 100 according to the embodiment will be described.

As shown in FIG. 12, the electronic device 100 acquires the AI reference value of the examinee as an initial setting (step S101). As the AI reference value, the average AI estimated from the age of the examinee may be used, or the AI on an empty stomach of the examinee obtained in advance may be used. Further, the electronic device 100 may use the AI determined to be before meals in steps S102 to S108 as the AI reference value, or the AI calculated immediately before the pulse wave measurement as the AI reference value. In this case, the electronic device 100 executes step S101 after steps S102 to S108.

Subsequently, the electronic device 100 acquires the pulse wave (step S102). For example, the electronic device 100 determines whether a predetermined amplitude or more is obtained for the pulse wave acquired in a predetermined measurement time (for example, 5 seconds). When a predetermined amplitude or more is obtained for the acquired pulse wave, the process proceeds to step S103. If no more than the predetermined amplitude is obtained, step S102 is repeated (these steps are not shown). In step S102, for example, when the electronic device 100 detects a pulse wave having a predetermined amplitude or more, the electronic device 100 automatically acquires the pulse wave.

The electronic device 100 calculates AI as a pulse wave-based index from the pulse wave acquired in step S102 and stores it in the storage 145 (step S103). The electronic device 100 may calculate an average value $AI_{ave}$ from $AI_n$ (an integer of n=1 to n) for each predetermined pulse rate (for example, three beats) and use this as AI. Alternatively, the electronic device 100 may calculate the AI at a specific pulse.

The AI may be calculated by making correction based on, for example, the pulse rate $P_R$, the pulse pressure $(P_F-P_S)$, the body temperature, the temperature of the detected part, and the like. It is known that pulse and AI, and pulse pressure and AI have a negative correlation, and temperature and AI have a positive correlation. When making the correction, for example, in step S103, the electronic device 100 calculates the pulse and the pulse pressure in addition to the AI. For example, the electronic device 100 may be equipped with a temperature sensor on the sensor 130 and acquire the temperature of the detected part when acquiring the pulse wave in step S102. AI is corrected by substituting the acquired pulse rate, pulse pressure, temperature, and the like, into a pre-created correction formula.

Subsequently, the electronic device 100 compares the AI reference value acquired in step S101 with the AI calculated in step S103 to estimate the blood fluidity of the examinee (step S104). When the calculated AI is larger than the AI reference value (in case of YES), the blood fluidity is estimated to be high, and the electronic device 100 notifies, for example, that the blood fluidity is high (step S105). When the calculated AI is not larger than the AI reference value (in case of NO), it is estimated that the blood fluidity is low, and the electronic device 100 notifies, for example, that the blood fluidity is low (step S1.06).

Subsequently, the electronic device 100 confirms with the examinee whether to estimate the state of glucose metabolism and lipid metabolism (step S107). If glucose metabolism and lipid metabolism are not estimated in step S107 (in case of NO), the electronic device 100 ends the process. When estimating glucose metabolism and lipid metabolism in step S107 (in case of YES), the electronic device 100 confirms whether the calculated AI was acquired before or after a meal (step S108). If it is not after meal (before meal) (in case of NO), the process returns to step S102 and the next pulse wave is acquired. If it is after a meal (in case of YES), the electronic device 100 stores the acquisition time of the pulse wave corresponding to the calculated AI (step S109). Subsequently, when acquiring a pulse wave (NO in step S110), the process returns to step 1022 and the next pulse wave is acquired. When the pulse wave measurement is completed (YES in step S110), the process proceeds to step S111 and beyond, and the electronic device 100 estimates the states of glucose metabolism and lipid metabolism of the examinee.

Subsequently, the electronic device 100 extracts the minimum extreme value and its time from the plurality of AIs calculated in step S044 (step S111). For example, when the AI as shown by the solid line in FIG. 11 is calculated, the electronic device 100 extracts the first minimum extreme value $AI_{P1}$ about 30 minutes after a meal and the second minimum extreme value $AI_{P2}$ about 2 hours after a meal.

Subsequently, the electronic device 100 estimates the state of glucose metabolism of the examinee from the first minimum extreme value $AI_{P1}$ and its time (step S112). Further, the electronic device 100 estimates the state of lipid metabolism of the examinee from the second minimum extreme value $AI_{P2}$ and its time (step S113). An example of estimating the state of glucose metabolism and lipid metabolism of the examinee is omitted because it is the same as in FIG. 11 described above.

Subsequently, the electronic device 100 notifies the estimation results of steps S112 and S113 (step S114), and ends the process shown in FIG. 12. The notifier 147 notifies, for example, "glucose metabolism is normal", "glucose metabolism abnormality is suspected", "lipid metabolism is normal", "lipid metabolism abnormality is suspected", and the like. Further, the notifier 147 may also notify an advice such as "see a doctor at a hospital" or "review your diet". Then, the electronic device 100 ends the process shown in FIG. 12.

In the present embodiment, the electronic device 100 can estimate the blood fluidity, the state of glucose metabolism and the state of lipid metabolism of the examinee from the indices based on the pulse wave. Therefore, the electronic device 100 can estimate the blood fluidity of the examinee and the state of glucose metabolism and lipid metabolism in a non-invasive manner in a short time.

In the present embodiment, the electronic device 100 can estimate the state of glucose metabolism and the state of lipid metabolism from the extreme value of the index based on the pulse wave and its time. Therefore, the electronic device 100 can estimate the state of glucose metabolism and lipid metabolism of the examinee in a non-invasive manner and in a short time.

In the present embodiment, the electronic device 100 can estimate the state of glucose metabolism and lipid metabolism of the examinee based on, for example, an index based on the pulse wave before meals (on an empty stomach). Therefore, the blood fluidity, glucose metabolism, and lipid metabolism of the examinee can be accurately estimated without considering the blood vessel diameter and/or the blood vessel stiffness which does not change in a short period of time.

In the present embodiment, the electronic device 100 can estimate the blood glucose value and lipid values of the examinee in non-invasive manner and in a short time if the pulse wavebased indices are calibrated with the blood glucose and lipid values.

Figure 13:
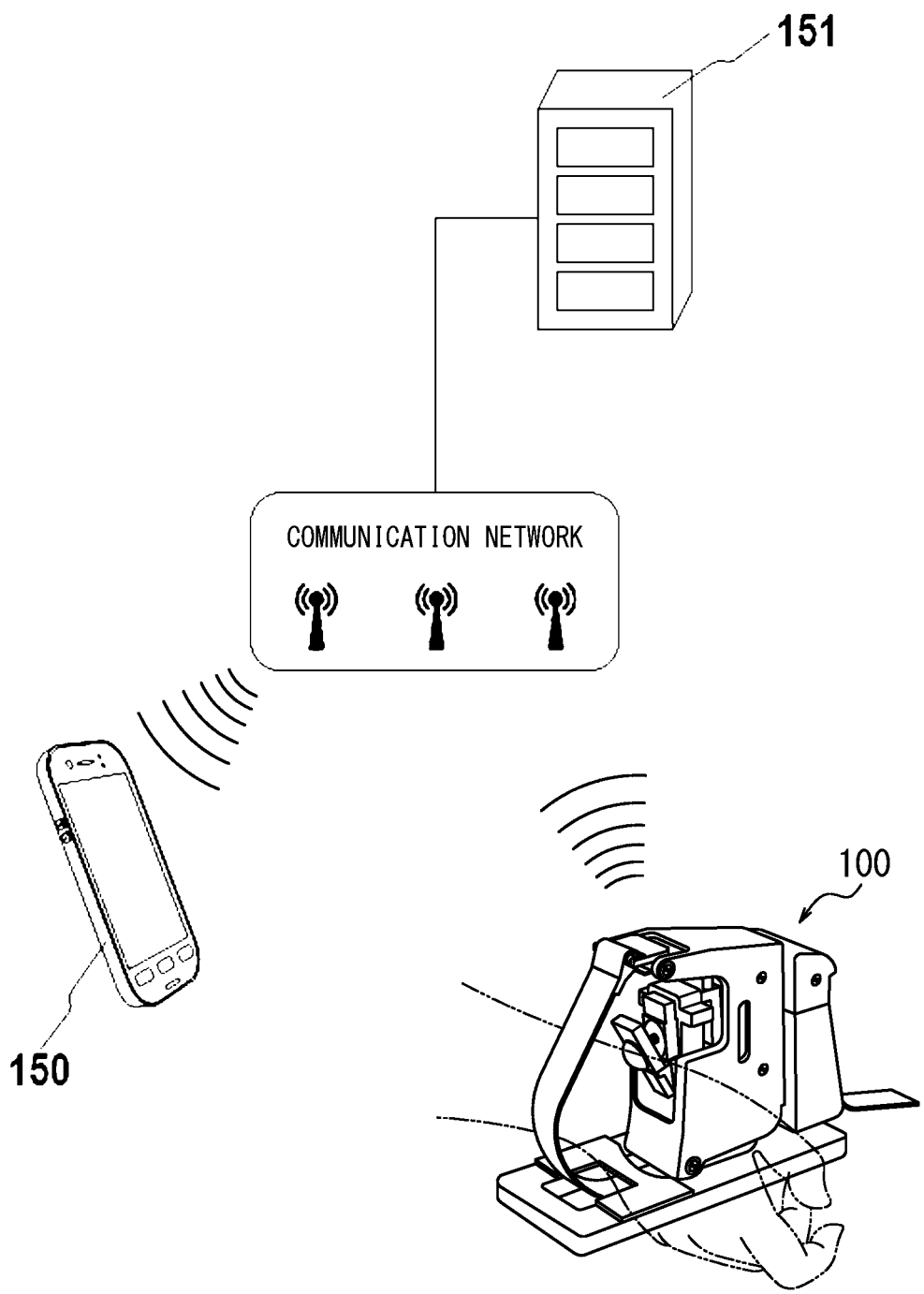
FIG. 13 is a schematic diagram showing a schematic configuration of the system according to the first embodiment.

FIG. 13 is a schematic diagram showing a schematic configuration of the system according to the first embodiment. The system shown in FIG. 13 consists of an electronic device 100, a server 151, a mobile terminal 150, and a communication network. As shown in FIG. 13, the index based on the pulse wave calculated by the electronic device 100 is transmitted to the server 151 through the communication network and stored in the server 151 as the personal information of the examinee. The server 151 estimates the blood fluidity and the state of glucose metabolism and lipid metabolism of the examinee by comparing with the past acquired information of the examinee and or various databases. The server 151 also creates optimal advice for the examinee. The server 151 returns the estimation results and the advice to the mobile terminal 150 owned by the examinee. The mobile terminal 150 can construct a system in which the received estimation results and advice are notified from the display of the mobile terminal 150. By using the communication function of the electronic device 100, the server 151 can collect information from a plurality of users, which further increases the accuracy of the estimation. Further, because the mobile terminal 150 is used as the notification means, the electronic device 100 does not require the notifier 147 and is further miniaturized. Further, because the server 151 estimates the blood fluidity and the states of glucose metabolism and lipid metabolism of the examinee, the computation load of the controller 143 of the electronic device 100 can be reduced. Further, because the past acquired information of the examinee can be stored in the server 151, the load on the storage 145 of the electronic device 100 can be reduced. Therefore, the electronic device 100 can be further miniaturized and simplified. In addition, the processing speed of computation is also improved.

The system according to the present embodiment shows a configuration in which the electronic device 100 and the mobile terminal 150 are connected by a communication network via the server 151, but the system according to the present invention is not limited to this. The electronic device 100 and the mobile terminal 150 may be directly connected to each other via a communication network without using the server 151.

So as to disclose the present disclosure completely and clearly, characteristic examples have been described. However, the accompanying claims are not limited to the foregoing embodiments, and should be configured to embody all variants and substitutable configurations that can be created by those skilled in the art within the scope of the basic matters set forth herein.

For example, in the foregoing embodiment, the case where the sensor 130 is provided with the angular velocity sensor 131 has been described, but the form of the electronic device 100 is not limited to this. The sensor 130 may comprise an optical pulse wave sensor including a light emitting part and a light receiving part, or may comprise a pressure sensor. The wearing part of the electronic device 100 is not limited to the wrist. The sensor 130 may be worn on an artery in the neck, ankle, thigh, and ear.

For example, in the foregoing embodiment, the state of glucose metabolism and lipid metabolism of the examinee was estimated based on the first extreme value and the second extreme value of the pulse wave based index and its time. However, the process executed by the electronic device 100 is not limited to this. In some cases, only one extreme value is expressed, and in other cases, no extreme value is expressed. The electronic device 100 may estimate the state of glucose and lipid metabolism of the examinee based on the overall trend (for example, integral value, Fourier transform, and the like) of the time variation of the calculated pulse wavebased index. Further, the electronic device 100 does not extract the extreme value of the index based on the pulse wave, but the state of glucose metabolism and lipid metabolism of the examinee may be estimated based on the time range when the index based on the pulse wave becomes equal to or less than a predetermined value.

For example, in the foregoing embodiment, the case of estimating the blood fluidity before and after a meal has been described, but the processing executed by the electronic device 100 is not limited to this. The electronic device 100 may estimate the fluidity of blood before and after exercise and during exercise, or may estimate the fluidity of blood before and after bathing and during bathing.

In the foregoing embodiment, the natural frequency of the first arm 134 may be close to the frequency of the acquired pulse wave. For example, when the frequency of the acquired pulse wave is 0.5 to 2 Hz (pulse 30 to 120), the first arm 134 may have a natural frequency in the range of 0.5 to 2 Hz. The natural frequency of the first arm 134 can be optimized by changing the length, weight of the first arm 134, the elastic modulus of the elastic body 140, the spring constant, or the like. By optimizing the natural frequency of the first arm 134, the electronic device 100 will be able to make more accurate measurements.

In the foregoing embodiment, it has been described that the electronic device 100 measures the pulse wave, but the pulse wave does not necessarily have to be measured by the electronic device 100. For example, the electronic device 100 may be connected to an information processing device such as a computer or a mobile phone by a wire or wirelessly, and may transmit the angular velocity information acquired by the angular velocity sensor 131 to the information processing device. In this case, the information processing device may measure the pulse wave based on the information of the angular velocity. The information processing device may execute estimation processing of glucose metabolism and lipid metabolism. When an information processing device connected to the electronic device 100 executes various types of information processing, the electronic device 100 does not have to comprise a controller 143, a storage 145, a notifier 147, and the like. When the electronic device 100 is connected to an information processing device by a wire, the electronic device 100 may not have a power supply 144 and may be powered by the information processing device.

The electronic device 100 does not have to comprise all the movable parts described in the foregoing embodiment. The electronic device 100 may comprise only a part of the movable parts described in the foregoing embodiment. For example, the measuring part 120 does not have to be configured to be rotatably with respect to the base 111. For example, the main body 121 may not be configured to be displaceable in the vertical direction with respect to the exterior 122. For example, the main body 121 does not have to be configured to be rotatably with respect to the exterior 122.

In the foregoing embodiment, it has been described that the upper end side of the exterior 122 is displaced in the y-axis negative direction by the examinee pulling the other end 110b of the wearing part 110. However, the exterior 122 may be configured so that the upper end side is displaced by another mechanism. For example, a mechanism capable of pressing in the y-axis negative direction is attached to the upper end side of the fixing part 112, and the mechanism may be configured to push the upper end side of the exterior 122 in the y-axis negative direction. As such a mechanism, for example, a ball screw can be used.

Figure 14:
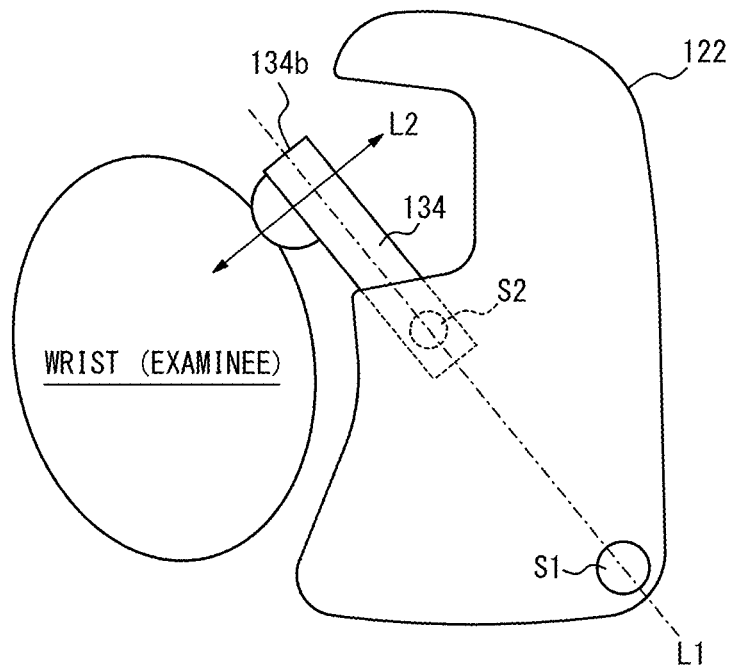
FIG. 14 is a schematic diagram schematically showing a modified example of the positional relationship between the examinee's wrist, the first arm of the sensor, and the exterior of the measuring part, in the front view.

In the example shown in FIG. 1, the axis S1 which is the rotation axis of the exterior 122 is arranged on the y-axis negative direction side of the exterior 122 in the front view, but the arrangement of the axis S1 is not limited to this. The shaft S1 may be arranged, for example, in the vicinity of the straight line L1 connecting the other end 134b, that is an outer end of rotational displacement in the first arm 134, to the shaft S2. For example, as shown in FIG. 14, the shaft S1 may be arranged on a straight line L1 connecting the other end 134b to the shaft S2. In the example shown in FIG. 14, because the first arm 134 extends from the other end 134b to the shaft S2, the shaft S1 is arranged on the straight line L1 in which the first arm 134 extends. When the axis S1 is arranged on the straight line L1, the displacement direction L2 of the pulse contact pad 132 with the axis S2 as the rotation axis coincides with the displacement direction of the pulse contact pad 132 with the axis S1 as the rotation axis. Therefore, when the exterior 122 is rotated with the shaft S1 as the rotation axis, the position on the wrist where the pulse contact pad 132 comes into contact is less likely to change. The closer the axis S1 is to the straight line L1 on which the first arm 134 extends, the less likely the position on the wrist where the pulse contact pad 132 comes into contact will change due to the rotation of the exterior 122. Therefore, the closer the axis S1 is to the straight line L1, the smaller the change in the contact state of the pulse contact pad 132 with the wrist when the examinee rotates the exterior 122 to fix the electronic device 100 on the wrist. Therefore, the closer the axis S1 is to the straight line L1, the easier the electronic device 100 is worn to the wrist in a state where the pulse contact pad 132 is in contact with the desired position.

Figure 15:
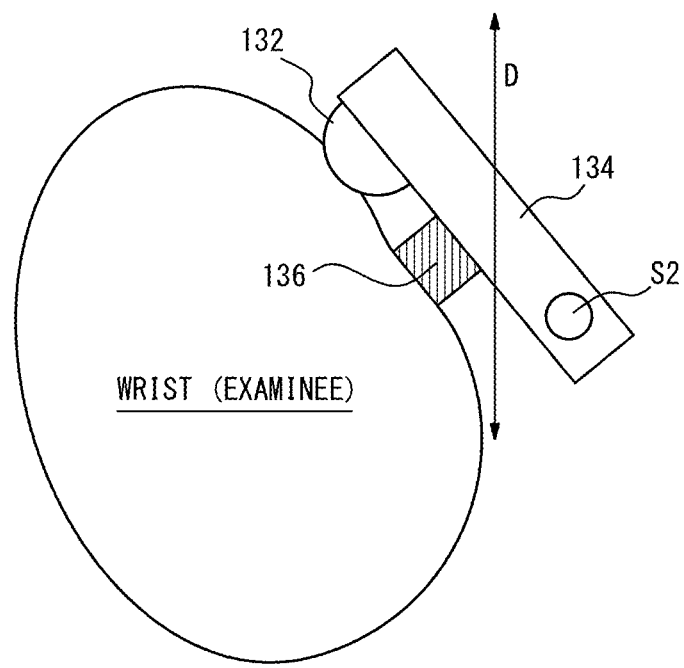
FIG. 15 is a schematic diagram schematically showing the positional relationship between the examinee's wrist and the first arm of the sensor in the front view.

Further, in the foregoing embodiment, it has been described that the end 122d functions as a stopper. However, in the present disclosure, the part that functions as a stopper is not limited to the end 122d. For example, as shown in FIG. 15, a stopper 136 may be provided on the main body 121. The stopper 136 may be located below the pulse contact pad 132 of the first arm 134. In this case, because the stopper 136 moves in conjunction with the vertical movement of the main body 121, it can function as a stopper even for a person with a thin wrist.

Second Embodiment

Next, the second embodiment will be described with reference to the drawings.

The electronic device according to the second embodiment is the electronic device 100 according to the first embodiment described above, in which the structure of the sensor 130 is modified. Hereinafter, the electronic device according to the second embodiment will be described, but the description that is the same as or similar to the electronic device 100 according to the first embodiment described above will be simplified or omitted as appropriate.

Figure 16:
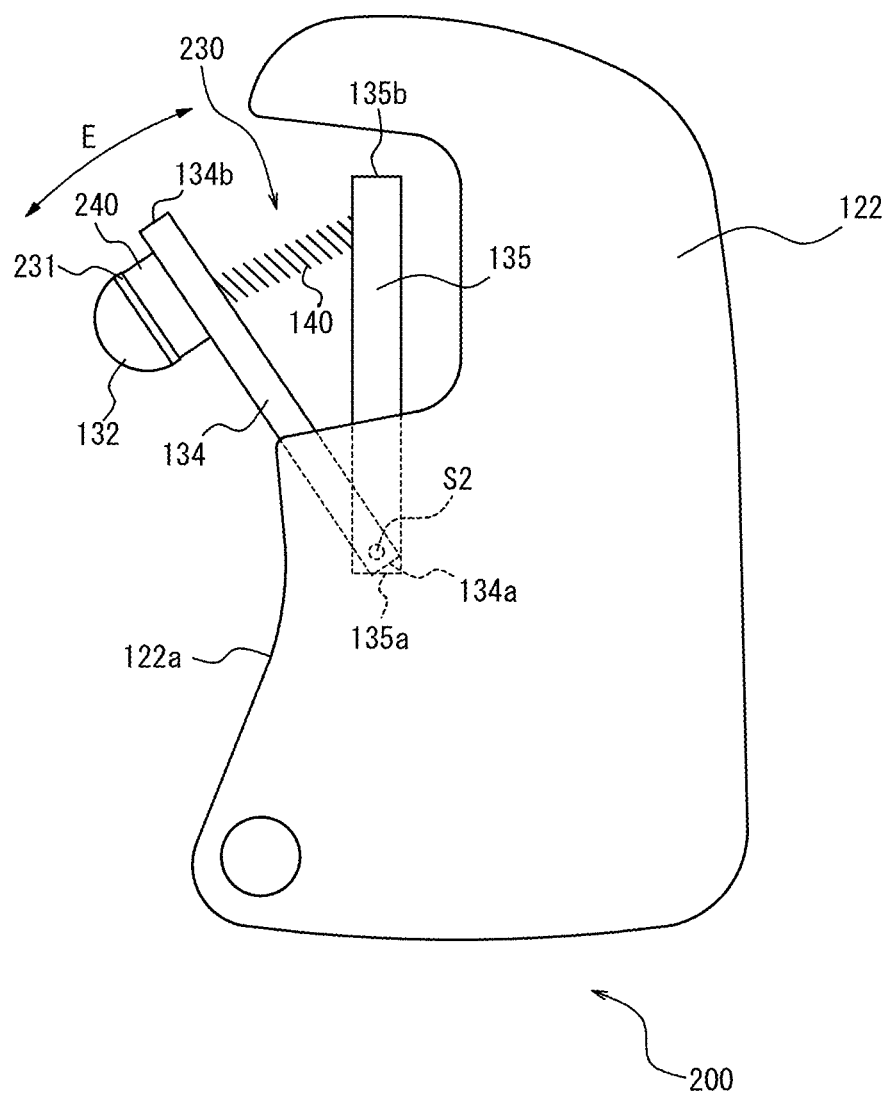
FIG. 16 is a schematic diagram showing an exterior and a sensor in a front view of the electronic device according to the second embodiment.

FIG. 16 is a schematic diagram showing an exterior and a sensor in a front view of the electronic device according to the second embodiment. As shown in FIG. 16, the electronic device 200 according to the second embodiment is an electronic device 100 (see FIG. 3) according to the first embodiment described above, in which the sensor 130 is changed to a sensor 230. In the electronic device 200 according to the second embodiment, the configuration other than the sensor 230 may be the same as the electronic device 100 according to the first embodiment described above.

As shown in FIG. 16, in the sensor 230 of the electronic device 200 according to the second embodiment, the first arm 134 is connected to the second arm 135. More specifically, one end 134a of the first arm 134 is connected to the lower end 135a of the second arm 135. As indicated by the arrow E in FIG. 16, the first arm 134 is connected to the second arm 135 in such a manner that one end 134a is an axis (rotation axis S2) and the other end 134b side is rotatable.

Further, the other end 134b side of the first arm 134 is connected to the other end 135b side on the upper side of the second arm 135 via an elastic body 140. The elastic body 140 may be any elastic body such as a spring, a resin, a sponge, or the like In the sensor 130, the first arm 134 is urged to the test part side of the examinee by the elasticity of the elastic body 140.

As shown in FIG. 16, in the sensor 230 of the electronic device 200 according to the second embodiment, the first arm 134 comprises an elastic member 240 and a sensor 231. Further, as shown in FIG. 16, the first arm 134 may comprise a pulse contact pad 132.

As shown in FIG. 16, the elastic member 240 is arranged on the first arm 134 on the surface opposite to the surface on which the elastic body 140 is installed. That is, the elastic member 240 and the elastic body 140 may be arranged on the surfaces opposite to each other in the first arm 134.

The elastic member 240 may be configured to include any elastic body having appropriate elasticity, such as a spring, a resin, a sponge, or the like. The elastic member 240 may, for example, be made of a silicone sheet of a predetermined thickness having a predetermined elasticity. The elastic member 240 will be further described below. The elastic member 240 and the first arm 134 may be adhered with an adhesive, double-sided tape, or the like. Here, the adhesion between the elastic member 240 and the first arm 134 may reduce the influence on the deformation of the elastic member 240. That is, even if the elastic member 240 and the first arm 134 are adhered to each other, the elastic member 240 may be configured to be appropriately deformable.

As shown in FIG. 16, in the elastic member 240, the sensor 231 is arranged on a surface opposite to the adhesive surface between the elastic member 240 and the first arm 134. The sensor 130 of the electronic device 200 according to the second embodiment comprises an elastic member 240 between the sensor 231 and the first arm 134. That is, the elastic member 240 is interposed between the sensor 231 and the first arm 134. In the second embodiment, the sensor 231 can directly or indirectly detect the pulsation at the test part of the examinee. The sensor 231 and the elastic member 240 may be adhered with an adhesive, double-sided tape, or the like. Here, the adhesion between the sensor 231 and the elastic member 240 may be made in such a manner that the adhesion less influences on the deformation of the elastic member 240. That is, even if the sensor 231 and the elastic member 240 are adhered to each other, the elastic member 240 may be configured to be appropriately deformable.

The sensor 231 may be, for example, an acceleration sensor or a sensor such as a gyro sensor. The sensor 231 will be further described below. Further, the sensor 231 may be the angular velocity sensor 131 in the sensor 130 according to the first embodiment. The sensor 231 may detect the displacement of the pulse contact pad 132 based on the pulse wave of the examinee.

As shown in FIG. 16, in the sensor 231, the pulse contact pad 132 is arranged on the surface opposite to the adhesive surface between the sensor 231 and the elastic member 240. The sensor 231 may be bonded to the pulse contact pad 132 with an adhesive, double-sided tape, or the like. The pulse contact pad 132 is a part that comes into contact with the test part where the pulse wave of the blood of the examinee is to be measured during measurement by the electronic device 200. Also in the present embodiment, the pulse contact pad 132 contacts the position where, for example, the ulnar artery or the radial artery locates. The pulse contact pad 132 may be configured in the same manner as the pulse contact pad 132 in the electronic device 100 according to the first embodiment.

As described above, the sensor 230 according to the second embodiment comprises an arm 134, a sensor 231 and an elastic member 240. The arm 134 is urged to the test part side of the examinee. The sensor 231 detects the pulsation at the test part of the examinee. The elastic member 240 is interposed between the sensor 231 and the arm 134. The configuration of the sensor 230 shown in FIG. 16 is an example and may be modified or changed as appropriate. For example, at least a part of the sensor 231 may be configured to be embedded in at least one of the elastic member 240 and the pulse contact pad 132. Further, in the simplified configuration, the pulse contact pad 132 may be omitted.

Figure 17:
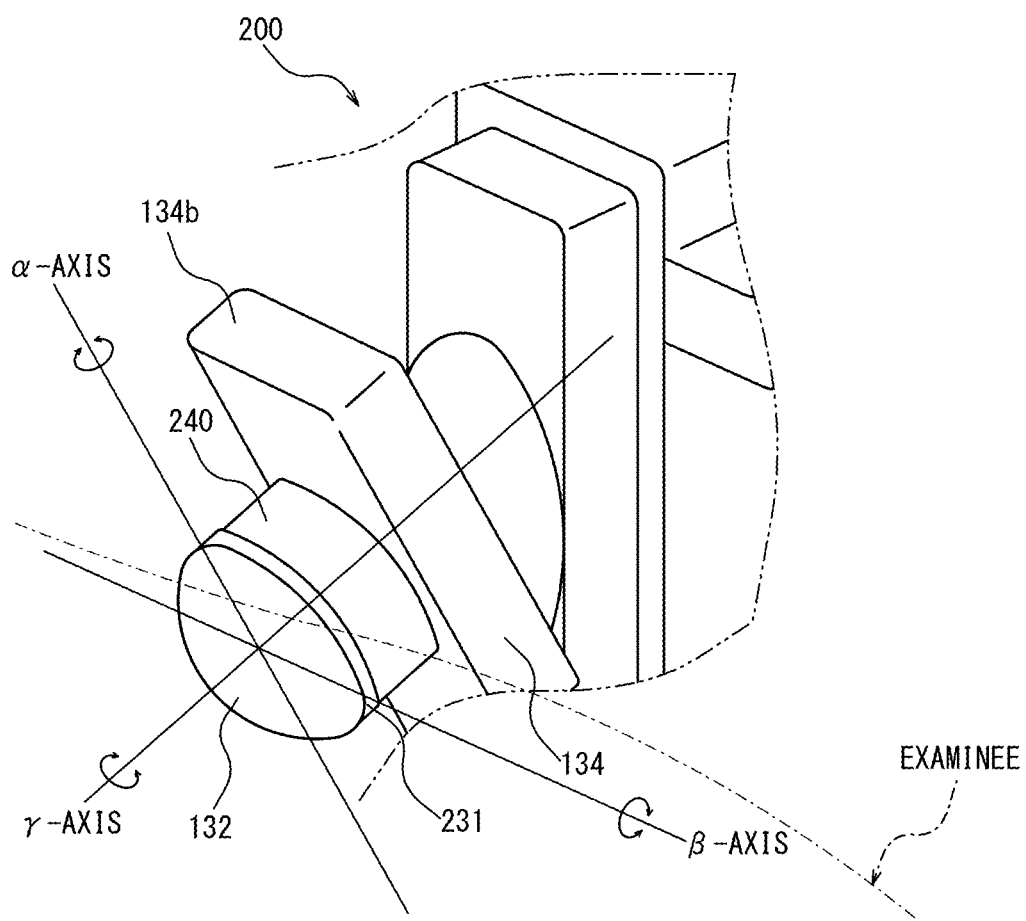
FIG. 17 is a schematic diagram partially showing a state in which the electronic device of FIG. 16 is worn.

FIG. 17 is a schematic diagram partially showing a state in which the examinee wears the electronic device 200 shown in FIG. 16. FIG. 17 mainly shows only a part of the sensor 230 in the electronic device 200 according to the second embodiment.

As shown in FIG. 17, in this embodiment, in the wearing state of the electronic device 200, the pulse contact pad 132 is in contact with the test part of the examinee, that is, the skin on the radial artery, the artery on the thumb side of the examinee's right hand. Due to the elastic force of the elastic body 140 arranged between the second arm 135 and the first arm 134, the first arm 134 (the other end 134b side) is urged to the test part side of the examinee. Further, the pulse contact pad 132 arranged on the first arm 134 via the elastic member 240 (and the sensor 231) is in contact with the skin on the radial artery of the examinee. The pulse contact pad 132 is displaced according to the movement of the radial artery of the examinee, that is, the pulsation. Therefore, the sensor 231 coupled to the pulse contact pad 132 also displaces according to the movement of the radial artery of the examinee, that is, the pulsation.

In the present embodiment, the sensor 231 coupled to the pulse contact pad 132 is coupled to the first arm 134 via the elastic member 240. Therefore, the sensor 231 is given a range of motion that is free to some extent due to the flexibility of the elastic member 240. In addition, due to the flexibility of the elastic member 240, the movement of the sensor 231 is less obstructed. Further, because the elastic member 240 has an appropriate elasticity, the elastic member 240 deforms following the pulsation at the test part of the examinee. Therefore, in the electronic device 200 according to the present embodiment, the sensor 231 can sensitively detect the pulsation at the test part of the examinee. As described above, in the present embodiment, the elastic member 240 may be deformable according to the pulsation at the test part of the examinee. Further, the elastic member 240 may be elastically deformed to such an extent that the sensor 231 can detect the pulsation at the test part of the examinee.

In the present embodiment, the sensor 231 may be a sensor such as a gyro sensor (gyroscope) configured to detect at least one of an angle (tilt), an angular velocity, and an angular acceleration of an object for a plurality of axes. In this case, the sensor 231 can detect a complex movement based on the pulsation at the test part of the examinee as a parameter for each of the plurality of axes. Further, the sensor 231 may be a 6-axis sensor in which a 3-axis gyro sensor and a 3-axis acceleration sensor are combined.

For example, as shown in FIG. 17, the sensor 231 may detect rotational motion centering on each of the three axes of the α-axis, the β-axis, and the γ-axis. The α-axis may be, for example, an axis along a direction substantially orthogonal to the radial artery of the examinee. Further, the β-axis may be, for example, an axis along a direction substantially parallel to the radial artery of the examinee. Further, the γ-axis may be, for example, an axis along a direction substantially orthogonal to both the α-axis and the β-axis.

As described above, in the present embodiment, the sensor 231 may detect the pulsation at the test part of the examinee as a part of the rotational motion centering on a predetermined axis. The sensor 231 may detect the pulsation at the test part of the examinee as rotational motion in at least two axes, or rotational motion in three axes. In the present disclosure, the "rotational motion" does not necessarily have to be a motion that displaces one or more rounds on the orbit of a circle. For example, in the present disclosure, the rotational motion may be, for example, a partial displacement (for example, a displacement along an arc) of less than one round on the orbit of a circle.

FIG. 18 is a graph showing an example of the results obtained by the sensor 231 detecting rotational motion, centering on each of the three axes, α-axis, β-axis, and γ-axis, as shown in FIG. 17. FIG. 18 shows the time variation of the signal intensity based on the results obtained by the sensor 231 detecting rotational motion, centering on each of the three axes, as shown in FIG. 17. In FIG. 18, the horizontal axis represents the elapsed time, and the vertical axis represents the signal intensity detected by the sensor 231.

The time variation of the signal intensity based on the rotational motion of the sensor 231 centering on the α-axis shown in FIG. 17 is indicated by the thick solid line in FIG. 18. Further, the time variation of the signal intensity based on the rotational motion of the sensor 231 centering on the β-axis shown in FIG. 17 is indicated by the alternate long and short dash line in FIG. 18. Further, the time variation of the signal intensity based on the rotational motion of the sensor 231 centering on the γ-axis shown in FIG. 17 is indicated by the dashed line in FIG. 18. In the example shown in FIG. 18, the time variation of the signal intensity based on the rotational motion of the sensor 231 centering on the α-axis and the β-axis has a remarkable peak based on the pulse wave of the examinee, respectively.

As shown in FIG. 18, the electronic device 200 according to the present embodiment can detect, for example, a rotational motion centering on each of the three axes by the sensor 231. Therefore, the electronic device 200 of this embodiment can increase the detection sensitivity of the pulse wave of the examinee by synthesizing the plurality of results detected by the sensor 231, such as by adding them up. Calculations such as addition may be performed by, for example, the controller 143. In this case, the controller 143 may calculate an index of the pulse wave based on the pulsation detected by the sensor 231.

For example, in the example shown in FIG. 18, the time variation of the signal intensity based on the rotational motion of the sensor 231 centering on the α-axis and the β-axis has a remarkable peak based on the pulse wave of the examinee, respectively. Therefore, the controller 143 can improve the detection accuracy of the pulse wave of the examinee by, for example, adding up the detection results for the α-axis, the β-axis, and the γ-axis. Therefore, according to the electronic device 200 of the present embodiment, it is possible to improve the usefulness for the examinee to measure the pulse wave.

As described above, the electronic device 200 according to the present embodiment may further comprise a controller 143 configured to calculate an index of a pulse wave based on the pulsation detected by the sensor 231. In this case, the controller 143 may synthesize (for example, add up) the results detected by the sensor 231 as at least two axes of rotational motion (for example, three axes of rotational motion). According to the electronic device 200 of the present embodiment, pulse wave signals in a plurality of directions can be detected. Therefore, according to the electronic device 200 of the present embodiment, by synthesizing the detection results for a plurality of axes, the signal intensity is increased as compared with the detection results for one axis. Therefore, according to the electronic device 200 of the present embodiment, signals having a good. SN ratio can be detected, detection sensitivity can be increased, and stable measurement becomes possible.

Further, in the detection results for the γ-axis shown in FIG. 18, the peak based on the pulse wave of the examinee does not appear remarkably as compared with the detection results for the other α-axis or β-axis. When the detection result with a low signal level such as the detection result for the γ-axis is added to the detection result for the other axes, the SN ratio may decrease. In addition, detection results with low signal levels can be regarded as mostly noise components. In such cases, detection results with low signal levels may not contain good pulse wave components. Therefore, in the embodiment, if there is an axis whose detection result is less than a predetermined threshold value among the detection results for a plurality of axes, the controller 143 does not have to add up the detection results for that axis.

Figure 19A:
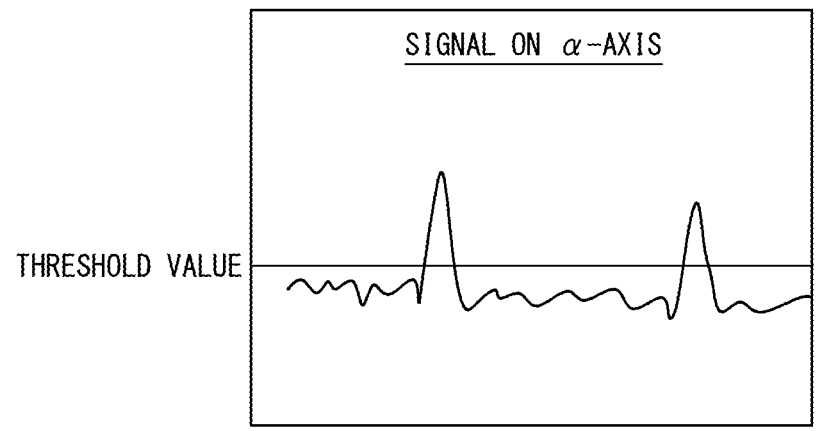
FIG. 19A is a diagram showing an example of a pulse wave acquired by the sensor.
Figure 19B:
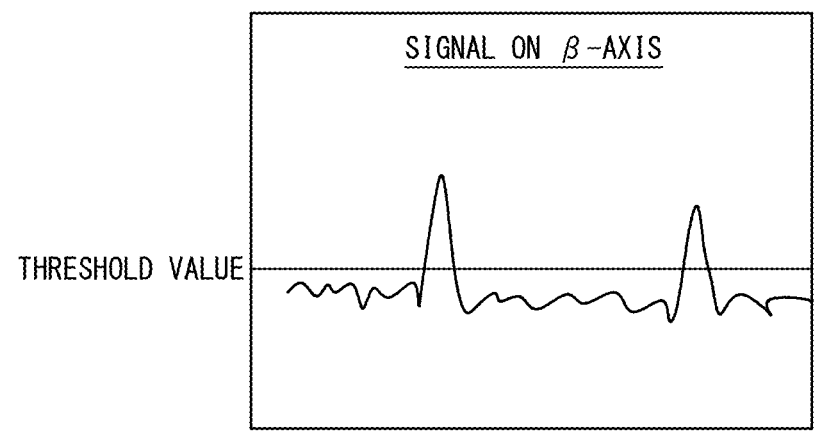
FIG. 19B is a diagram showing an example of a pulse wave acquired by the sensor.
Figure 19C:
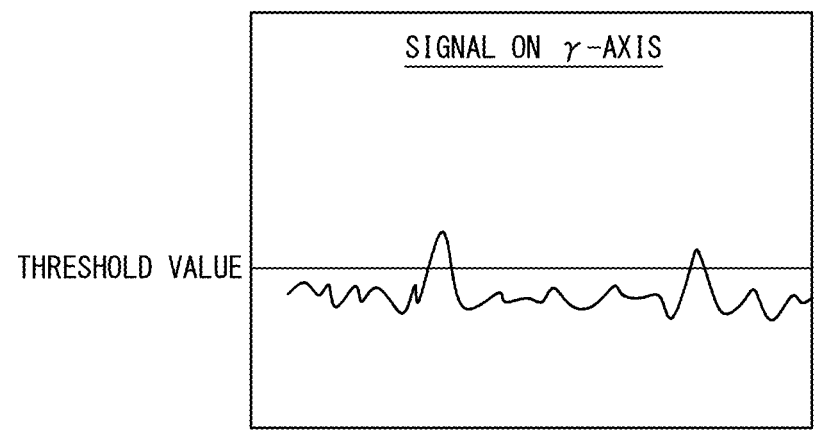
FIG. 19C is a diagram showing an example of a pulse wave acquired by the sensor.

For example, as in the case of the example shown in FIG. 18, it is assumed that the pulsation of an examinee is detected by the sensor 231 as a rotational motion centering on each of the α-axis, β-axis, and γ-axis. As a result, as shown in FIG. 19A, it is assumed that the peak value in the detection result for the α-axis exceeds a predetermined threshold value. Further, as shown in FIG. 19B, it is assumed that the peak value in the detection result for the β-axis also exceeds a predetermined threshold value. Further, as shown in FIG. 19C, it is assumed that the peak value in the detection result for the γ-axis also exceeds a predetermined threshold value. In such a case, the controller 143 may calculate an addition of all the detection results for the α-axis, the β-axis, and the γ-axis as an index of the pulse wave based on the pulsation detected by the sensor 231.

Figure 20A:
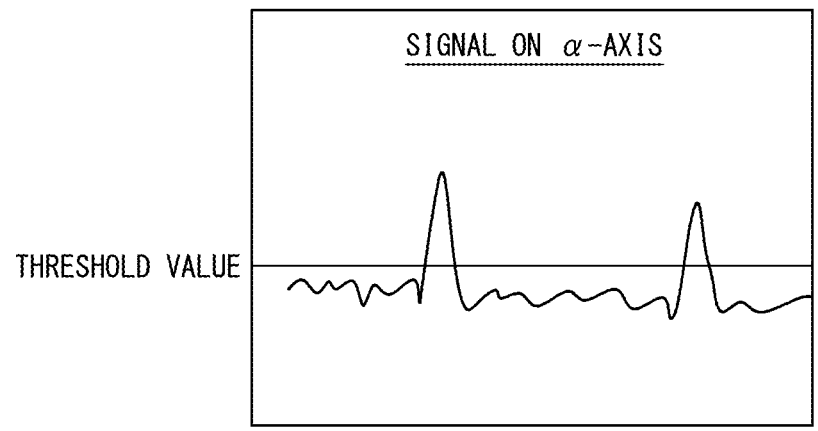
FIG. 20A is a diagram showing an example of a pulse wave acquired by the sensor.
Figure 20B:
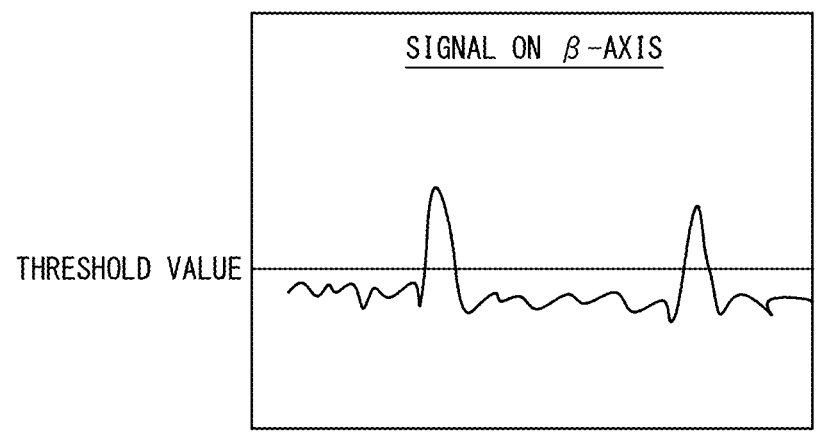
FIG. 20B is a diagram showing an example of a pulse wave acquired by the sensor.
Figure 20C:
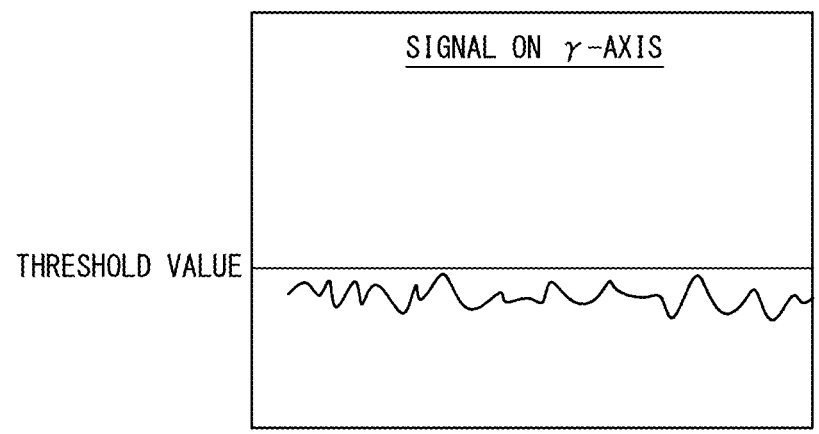
FIG. 20C is a diagram showing an example of a pulse wave acquired by the sensor.

On the other hand, for example, as a result of detecting the pulsation of an examinee, as shown in FIG. 20A, it is assumed that the peak value in the detection result for the α-axis exceeds a predetermined threshold value. Further, as shown in FIG. 20B, it is assumed that the peak value in the detection result for the β-axis also exceeds a predetermined threshold value. However, as shown in FIG. 20C, it is assumed that the peak value in the detection result for the γ-axis does not exceed a predetermined threshold value. In such a case, the controller 143 may calculate an addition of only the detection results for the α-axis and the β-axis as an index of the pulse wave based on the pulsation detected by the sensor 231.

When performing such processing, the controller 143 may set the threshold value, that is a reference for whether the detection result for each axis is included in the total, separately for each axis, or may determine the same threshold value for each axis. In either case, a threshold value may be appropriately set so that the pulsation of the examinee is appropriately detected in the detection result for each axis.

Thus, in the electronic device 200 according to the present embodiment, the controller 143 may synthesize only the result of the sensor 231 detecting as the rotational motion of at least two axes having a component of a predetermined threshold value or more. Therefore, according to the electronic device 200 of the present embodiment, a decrease in the SN ratio of the detection result can be suppressed. Therefore, according to the electronic device 200 of the present embodiment, the usefulness for the examinee to measure the pulse wave can be improved.

Further, as described above, when adding up the detection results for a plurality of axes, it is assumed that inconvenience will occur if the detection results for each axis are simply added up as they are. It is assumed that this is because the polarity of the result detected by the sensor 231 does not match due to the positional relationship between the pulsation direction of the examinee and the sensor 231. For example, it is assumed that the polarity of the detection result for a certain axis may be reversed when the sensor 231 is used to detect the pulsation of the examinee's right hand and when the sensor 231 is used to detect the pulsation of the left hand.

Figure 21A:
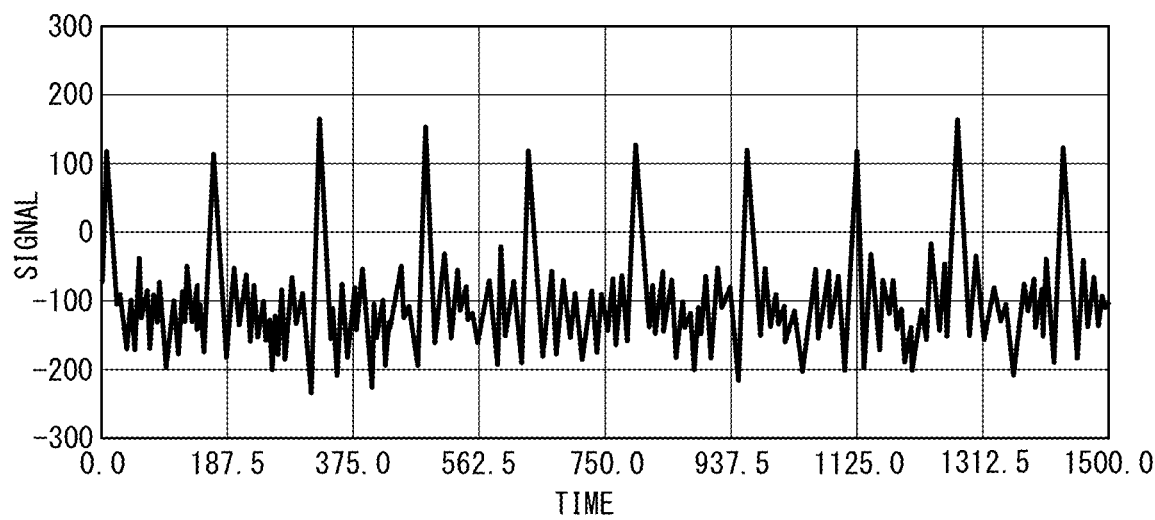
FIG. 21A is a diagram showing an example of a pulse wave acquired by the sensor.
Figure 21B:
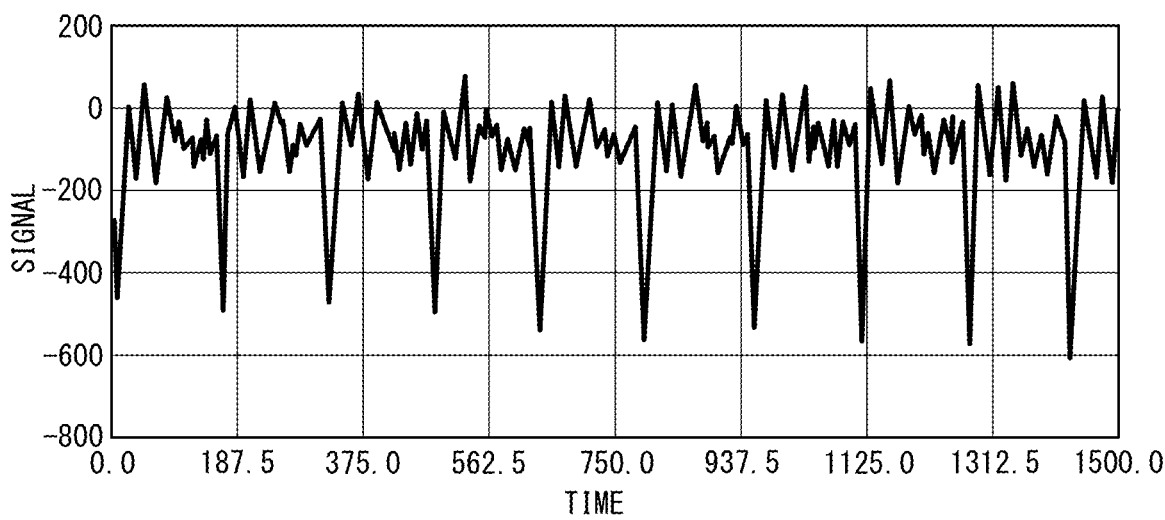
FIG. 21B is a diagram showing an example of a pulse wave acquired by the sensor.

For example, when the pulsation of the examinee is detected, it is assumed that an upward peak is detected almost periodically in the detection result for a certain axis, as shown in FIG. 21A. However, at the same time, as shown in FIG. 21B, it is also assumed that on the contrary, downward peaks are detected almost periodically in the detection results for the other axes. In this way, when the polarities are reversed in the detection results for a plurality of axes, it is assumed that the peaks cancel each other out and a good result cannot be obtained if the polarities are simply added up as they are.

Therefore, in the present embodiment, when the polarities are reversed in the detection results for a plurality of axes, the controller 143 may invert the polarity of the detection result for at least one axis and then add it to the detection results for the other axes.

For example, when the polarities are reversed in the detection results for the two axes as shown in FIGS. 21A and 21B, the controller 143 may invert the polarity of the detection result for one axis according to the other axis. In this case, the controller 143 may, for example, invert the polarity of the detection result shown in FIG. 21B according to the polarity of the detection result shown in FIG. 21A.

Figure 22A:
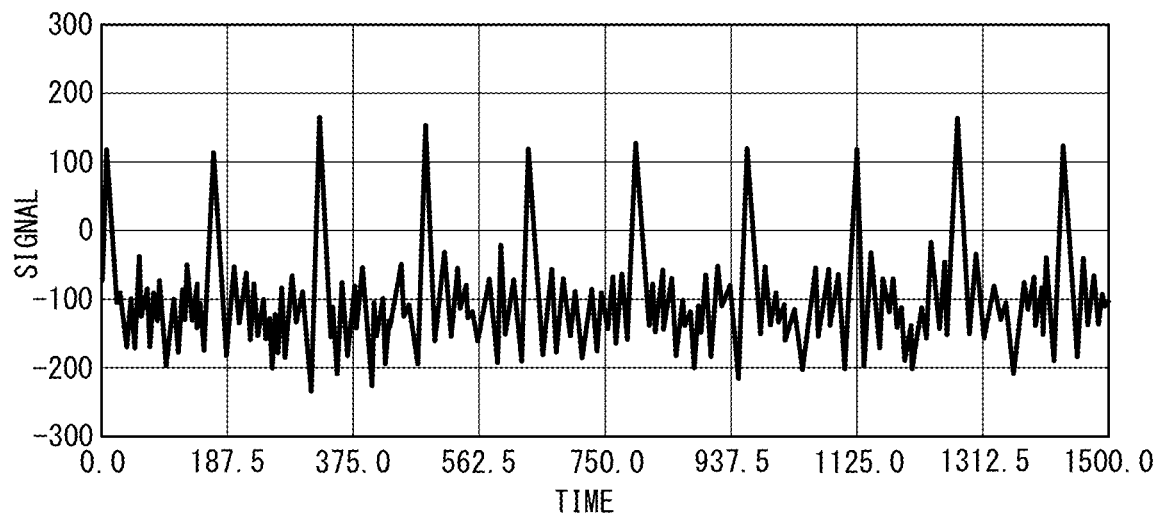
FIG. 22A is a diagram showing an example of a pulse wave acquired by the sensor.
Figure 22B:
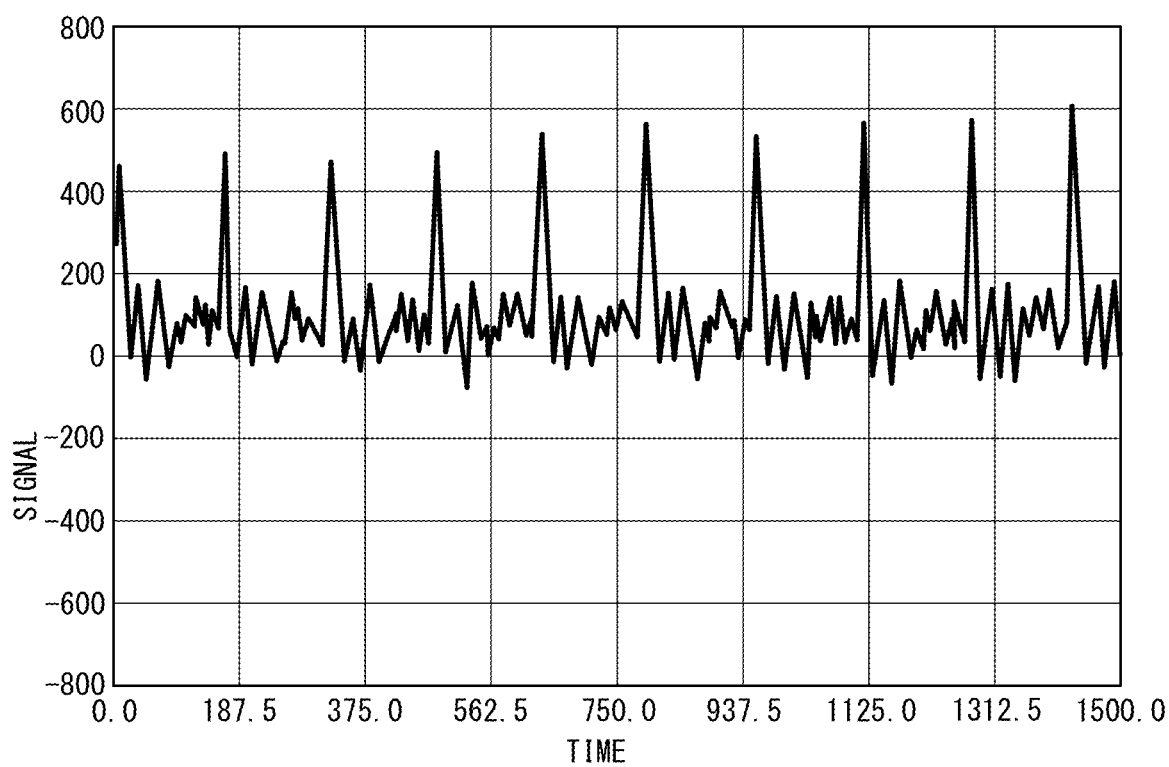
FIG. 22B is a diagram showing an example of a pulse wave acquired by the sensor.

FIG. 22A, as in the detection result shown in FIG. 21A, shows the state in which an almost periodic upward peak is detected in the detection result for a certain axis when the pulsation of the examinee is detected. On the other hand, FIG. 22B shows a state in which the polarity of the detection result shown in FIG. 21B is reversed. The detection results shown in FIGS. 22A and 22B are respectively aligned in polarity, and in both cases, the upward peaks are detected at the same timing almost periodically. The controller 143 can improve the detection accuracy of the pulse wave of the examinee by performing such a process and then adding up the detection results for the plurality of axes.

As described above, in the electronic device 200 according to the present embodiment, the controller 143 may synthesize the result, detected by the sensor 231 as the rotational motion of at least two axes, after the respective polarities are aligned. According to the electronic device 200 of the present embodiment, the accuracy of detecting the examinee's pulse wave can be improved. Therefore, according to the electronic device 200 of the present embodiment, the usefulness for the examinee to measure the pulse wave can be improved.

As described above, when performing the process of aligning the polarities of the detection results for a plurality of axes by inverting the polarities of the detection results for at least one axis, the direction of polarity in each detection result needs to be determined. Such determination of the direction of polarity can be performed by various methods. For example, the controller 143 may determine whether the peak in the detection result for each axis is oriented in the positive direction side or the negative direction side of the signal intensity. Further, for example, the controller 143 may determine whether the peak in the detection result for each axis is larger or smaller than the average value of the signals. Further, when inverting the polarity of the detection result for at least one axis, the controller 143 may multiply the detection result for inverting the polarity by −1.

Furthermore, after appropriately inverting the polarity of the detection results as described above, the controller 143 may add or subtract a predetermined value to the entire detection results and then add them to the detection results for the other axes. Here, adding or subtracting a predetermined value to the entire detection results corresponds to, for example, moving the entire graph shown in FIG. 22B in the vertical direction (positive or negative direction of the signal). Further, the controller 143 may appropriately weight the detection results for each axis or correct the detection results for each axis before adding the detection results for the plurality of axes.

Modified Example of the Second Embodiment

Next, a modified example of the second embodiment will be described.

Figure 23:
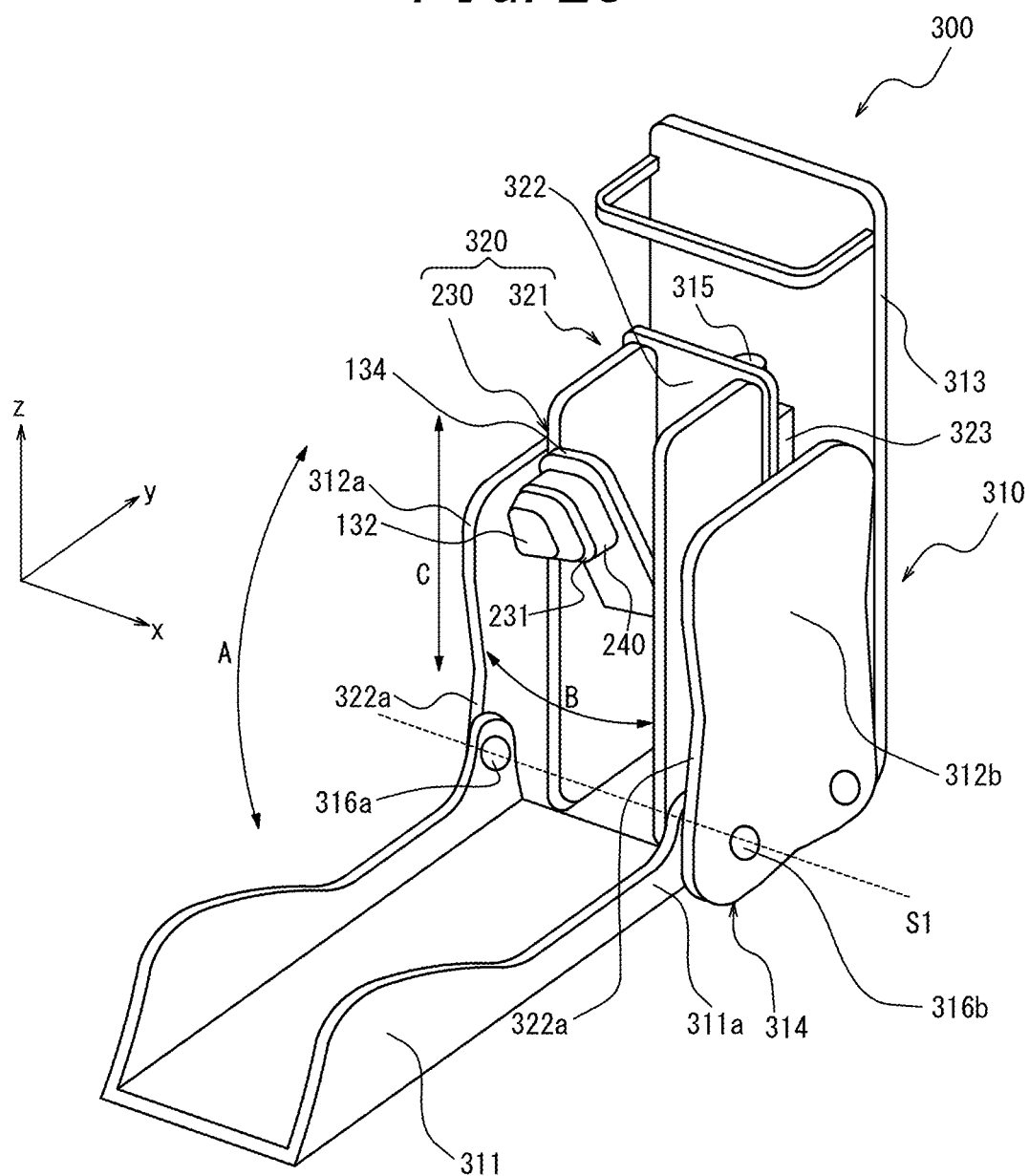
FIG. 23 is a schematic external perspective diagram of the electronic device according to the modified example of the second embodiment.
Figure 24:
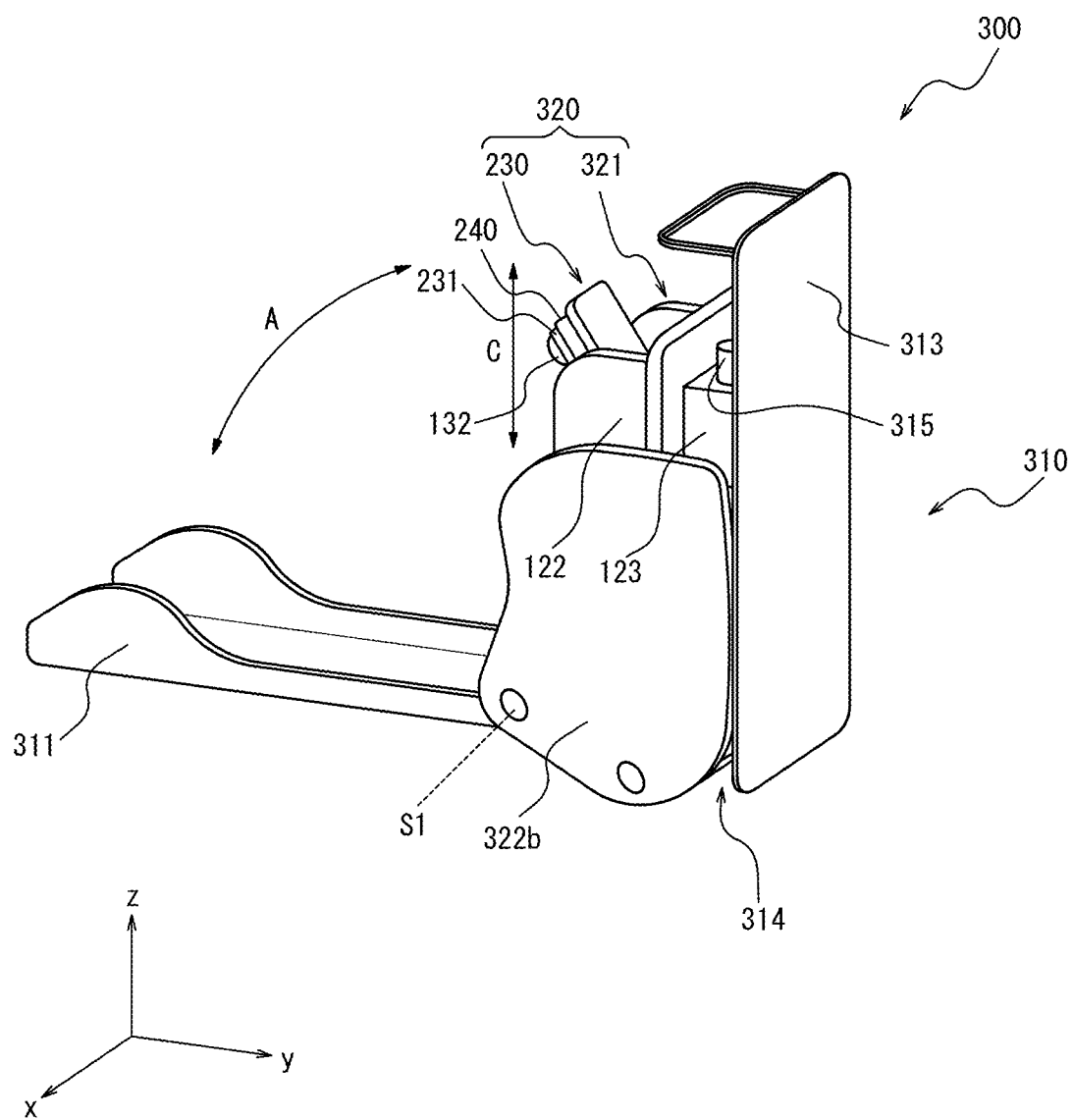
FIG. 24 is a schematic external perspective diagram of the electronic device according to a modified example of the second embodiment.

As described above, the electronic device 200 according to the second embodiment is the electronic device 100 according to the first embodiment, in which the sensor 130 is changed to the sensor 230. In the electronic device 200 according to the second embodiment, as long as the configuration of the sensor 230 is maintained, the other functional parts and/or members may have any configuration as appropriate. Hereinafter, some such examples will be described FIGS. 23 and 24 are schematic external perspective diagrams of the electronic device according to a modified example of the second embodiment. As shown in FIGS. 23 and 24, in the electronic device 300 according to the modified example of the second embodiment, the sensor 230 may be configured in the same manner as the electronic device 200 according to the second embodiment described above.

FIGS. 23 and 24 show the schematic appearance of the electronic device 300 when viewed from different perspectives. The electronic device 300 comprises an exterior 310 and a measuring part 320.

The electronic device 300 measures the biological information of the examinee in a state where the test part of the examinee is in contact with the measuring part 320. The biological information measured by the electronic device 300 is the pulse wave of the examinee that can be measured by the measuring part 320. In the modified example, as an example, the electronic device 300 will be described below assuming that the wrist of the examinee is in contact with the measuring part 320 to acquire a pulse wave.

The measuring part 320 is used for measuring biological information. The exterior 310 covers at least a part of the measuring part 320 from the outside world. The exterior 310 can protect a part covered by the measuring part 320. When measuring biological information using the electronic device 300, the examinee supports the electronic device 300 by holding the exterior 310 with one hand.

The exterior 310 comprises a cover 311, two side surfaces 312a and 312b, a back surface 313, and a bottom surface 314. In the exterior 310, the two side surfaces 312a and 312b and the back surface 313 form a holding surface held by the examinee to measure biological information.

Figure 25:
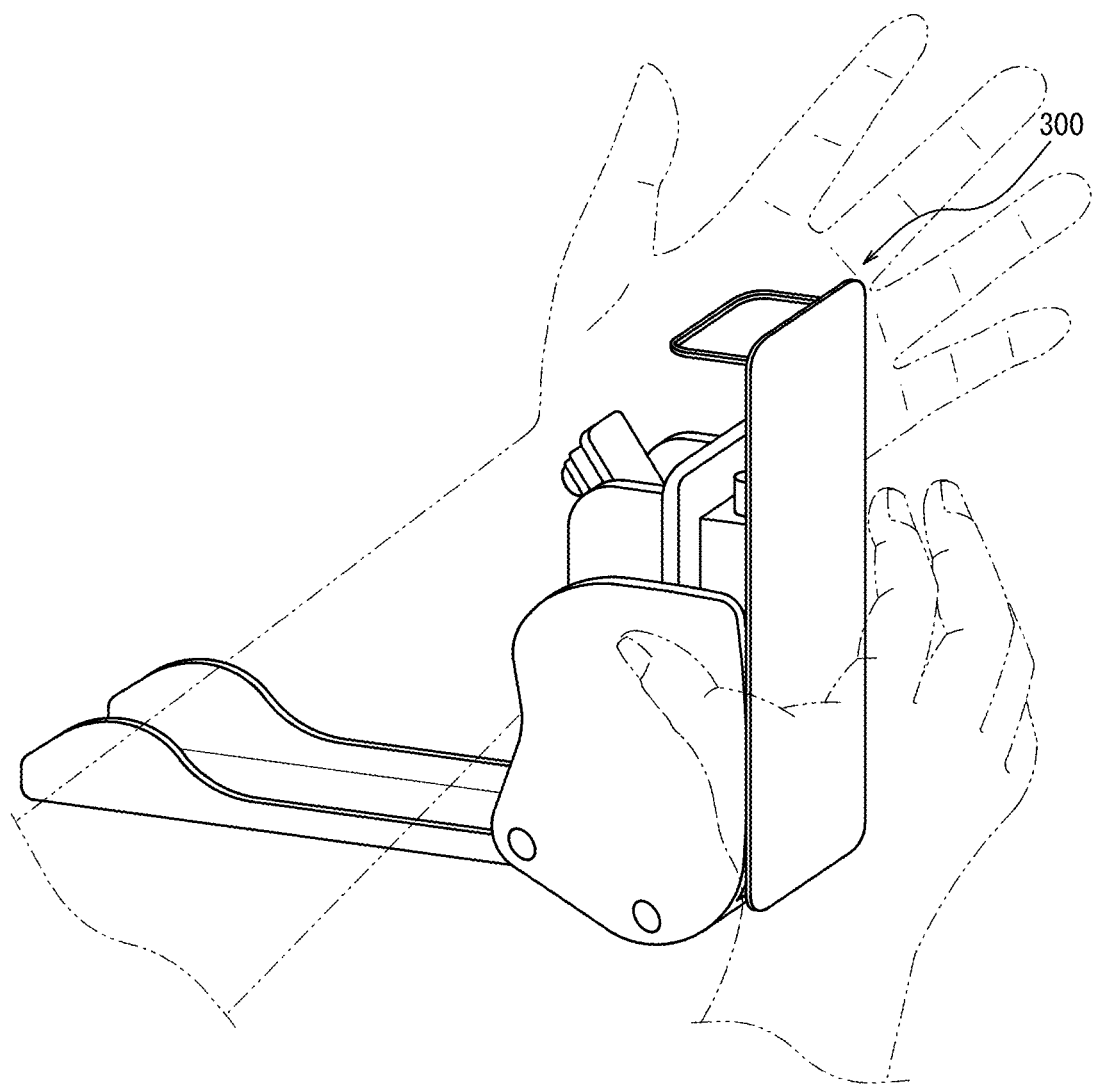
FIG. 25 is a schematic diagram showing a state in which an examinee measures biological information using an electronic device according to a modified example of the second embodiment.

FIG. 25 is a schematic diagram showing how an examinee measures biological information using the electronic device 300. When measuring biological information, the examinee places the electronic device 300 on the table so that the cover 311 and the bottom surface 314 are in contact with a table such as a desk. At least a part of the position where the cover 311 and/or the bottom surface 314 come into contact with the table may be provided with a non-slip material such as rubber. Provision of the non-slip material makes it easier to place the electronic device 300 stably on the table.

With the electronic device 300 placed on the table, the examinee places his or her wrist on the cover 311 and presses the wrist against the measuring part 320. The examinee, for example, presses his or her wrist against the measuring part 320 so that the pulse contact pad 132 of the measuring part 320, described below, comes into contact with the position where the ulnar or radial artery is located. At this time, the examinee can maintain contact state between the pulse contact pad 332 and his or her wrist by supporting the holding surface with a hand on the side of not pressing the wrist, and pressing the pulse contact pad against the side of the wrist. The electronic device 300 measures the pulse wave of blood flowing through the ulnar artery or the radial artery on the examinee's wrist.

With reference to FIGS. 23 and 24, in the present modified example, the back surface 313 is formed in a substantially rectangular flat plate shape. The present specification, as shown in FIGS. 23 and 24, will be described with the short side direction of the substantially rectangular flat plate shaped back 313 as the x-axis direction, the long side direction of the substantially rectangular flat plate shaped back 313 as the z-axis direction, and the orthogonal direction of the flat plate shaped back 313 (That is, the orthogonal direction of the xz surface) as the y-axis direction. Further, some parts of the electronic device 300 are configured to be movable, but when describing directions related to the electronic device 300 herein, the x-axis, y-axis, and z-axis directions in the state shown in FIGS. 23 and 24 will be indicated unless otherwise mentioned. Further, the y-axis negative direction is referred to as the front side of the electronic device 300, and the y-axis positive direction is referred to as the back side of the electronic device 300. Further, the x-axis positive direction is the left side of the electronic device 300, and the x-axis negative direction is the right side of the electronic device 300.

The bottom surface 314 is formed in a flat plate shape, for example. In the electronic device 300, the bottom surface 314 is arranged to be orthogonal to the back surface 313 on the short side below the substantially rectangular back surface 313. The back surface 313 and the bottom surface 314 may be fixed to each other. A shaft 315 extending in the direction along the holding surface, that is, in the z-axis direction is fixed to the bottom surface 314.

The two side surface 312a and 312b are formed in a flat plate shape. In the electronic device 300, the two side surfaces 312a and 312b are arranged to be orthogonal to the back surface 313 on each of the two long sides of the substantially rectangular back surface 313. The back surface 313 and the two side surface 312a and 312b may be fixed to each other.

In the modified example, the side surfaces 312a and 312b, constituting the holding surface of the exterior 310, and the back surface 313 are formed in a U-shape in the top view. The holding surface extends along the z-axis direction.

In the electronic device 300, the back surface 313 protects the back surface side of the measuring part 320. Further, the bottom surface 314 protects the bottom surface side of the measuring part 320. Further, the left and right side surface sides of the measuring part 320 are protected by the two side surfaces 312a and 312b.

The cover 311 is configured to include a substantially rectangular flat plate shaped member and a member provided so as to be orthogonal from the long side of the flat plate shaped member to the flat plate shaped member. As shown in FIG. 25, as an example, the examinee puts his or her wrist on a member provided so as to be orthogonal to the flat plate shaped member in the cover 311 and causes the electronic device 300 to measure the biological information. By placing the wrist on the cover 311 during measuring the biological information, the examinee can stabilize the position of the wrist. As a result, the examinee can make the measuring part 320 stably contact the wrist, and the accuracy of biological information measurement can easily be improved.

The cover 311 is connected to the side surfaces 312a and 312b at one end in the 311a side. One end 311a refers to the back side end in the state shown in FIG. 23. The cover 311 is connected to the side surfaces 312a and 312b, in such a manner that it can be rotated on the yz surface, with the straight line (axis) S1 connecting the connection 316a between the cover 311 and the side surface 312a and the connection 316b between the cover 311 and the side surface 312b as the axis, as indicated by the arrow A in FIG. 23. That is, the cover 311 can displace the two states: a state in which the flat plate -shaped member is along the xy surface as shown in FIG. 23; and a state in which the flat plate-shaped member is along the xz surface by rotating the cover 311 on the yz surface with the axis S1 as an axis. The state in which the flat-shaped member of the cover 311 is along the xy surface as shown in FIG. 23 is also described below as the state in which the electronic device 100 is open. The state in which the flat-shaped member of the cover 311 is along the xz surface is also described below as the state in which the electronic device 300 is closed.

Figure 26:
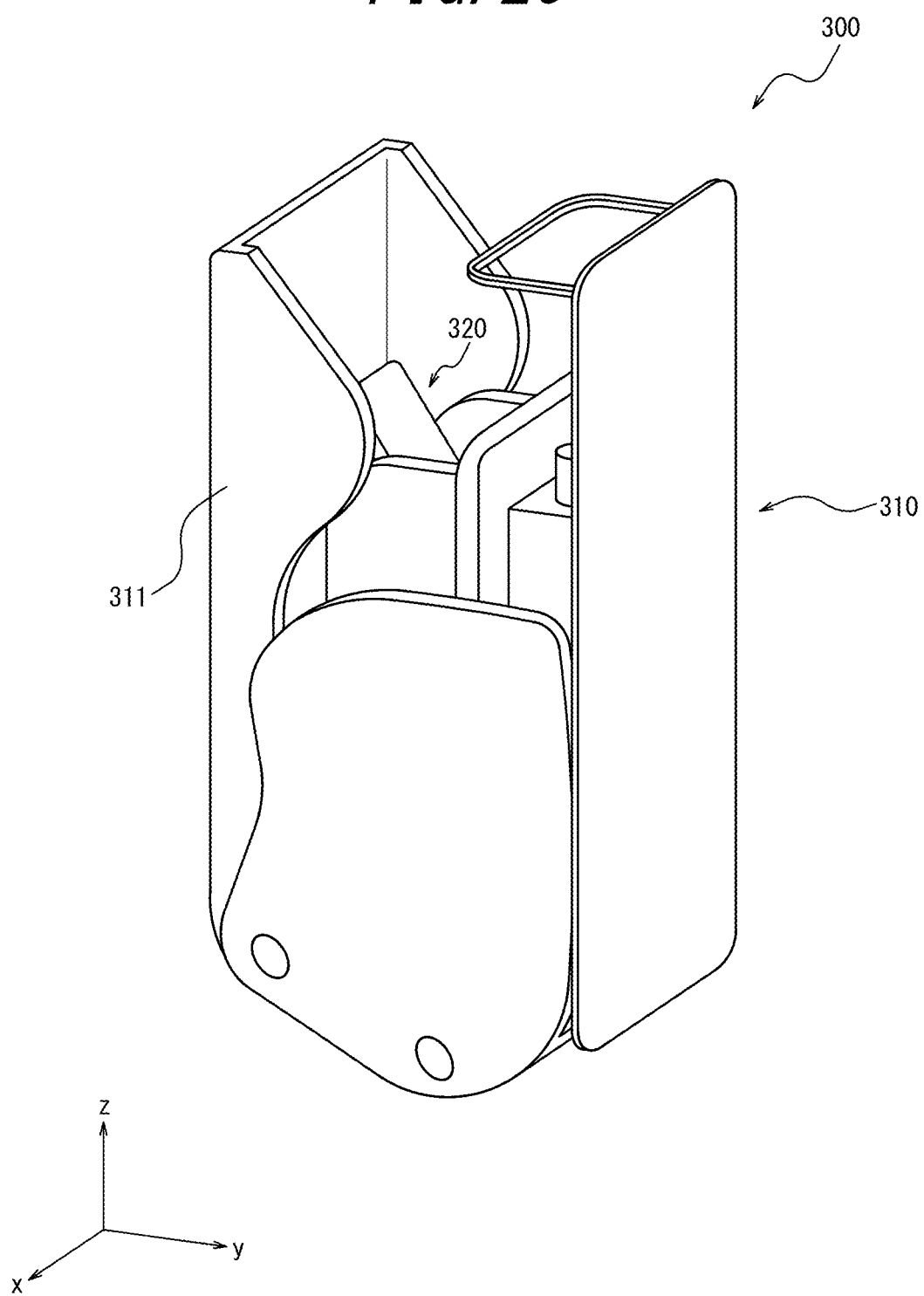
FIG. 26 is a schematic external perspective diagram showing a state when the electronic device according to a modified example of the second embodiment is not in use.

FIG. 26 is a schematic external perspective diagram showing a state when the electronic device 300 is not in use, that is, a state in which biological information is not measured using the electronic device 300. When the electronic device 300 is not in use, the examinee can keep the cover 311 of the electronic device 300 closed as shown in FIG. 26. By keeping the cover 311 closed, the front side of the measuring part 320 is protected. Further, by keeping the cover 311 closed, the electronic device 300 is in a state of being folded smaller than in the open state. Therefore, the examinee can easily carry the electronic device 300 in, for example, a case or a bag.

Referring to FIGS. 23 and 24, the measuring part 320 comprises a main body 321 and the sensor 230.

The main body 321 comprises a wall 322 with walls in three directions: the left side; right side; and the back side. That is, the wall surface 322 is formed in a U-shape when the electronic device 300 is viewed from above.

The main body 321 comprises a connecting part 323 on the back surface side of the wall surface 322. The connecting part 323 comprises a shaft bearing for passing the shaft 315, and the measuring part 320 is attached to the exterior 310 via the shaft 315 by passing the shaft 315 through the shaft bearing. Therefore, the measuring part 320 is attached to the exterior 310 in such a manner that it can be rotated centering on the axis 315 on the xy-surface intersecting the holding surfaces: the side surfaces 312a and 312b; and the back surface 313, as indicated by the arrow B in FIG. 23. That is, the measuring part 320 is attached to the exterior 310 in such a manner that it can rotate along the xy surface with respect to the exterior 310.

The measuring part 320 is attached to the exterior 310 in such a manner that it can be displaced vertically with respect to the exterior 310 along the axis 315, that is, along the z-axis direction, as indicated by the arrows C in FIGS. 23 and 24. In the present modified example, because the shaft 315 is configured along the holding surface, the measuring part 320 can be displaced along the holding surface.

Figure 27:
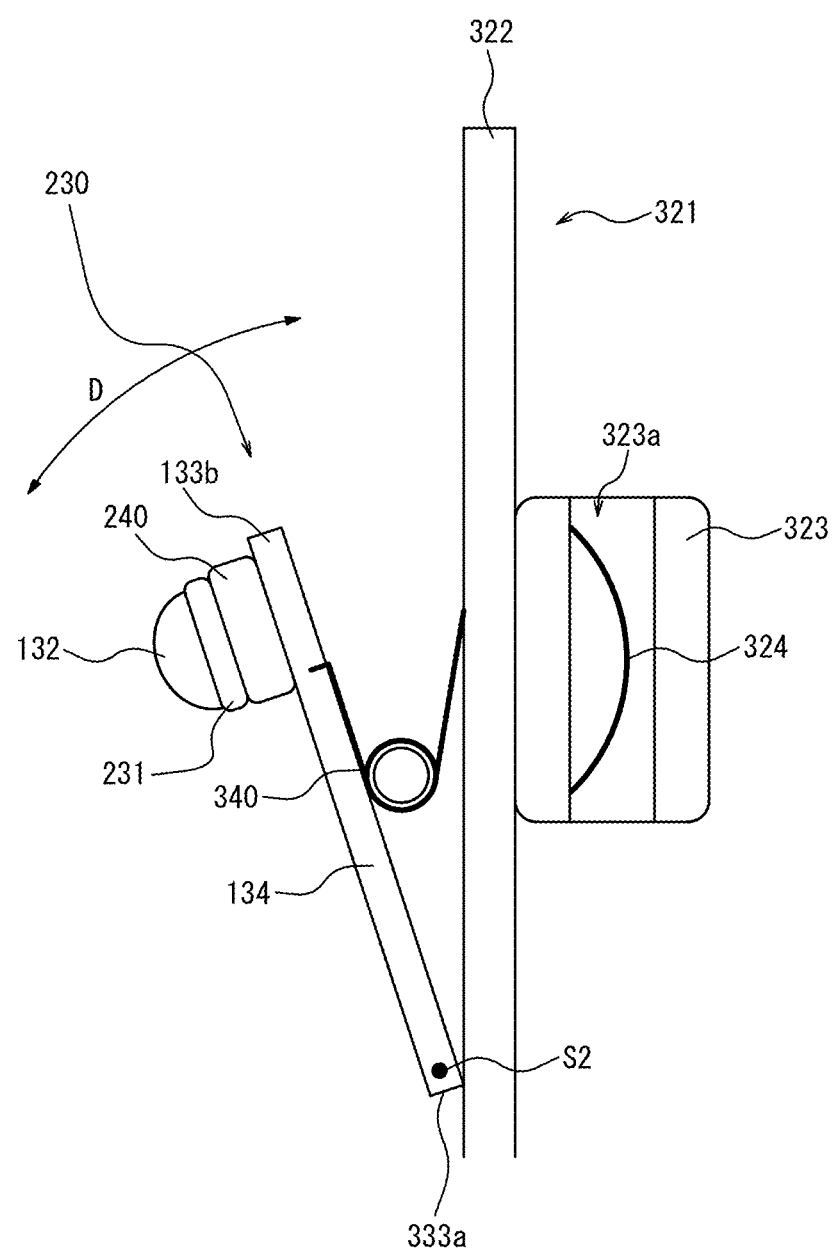
FIG. 27 is a schematic diagram showing a sensor and a main body of the electronic device according to a modified example of the second embodiment.

The sensor 230 is arranged in a space surrounded by the wall surface formed by the wall surface 322 of the main body 321. Here, the details of the measuring part 320 will be described with reference to FIG. 27. FIG. 27 is a schematic diagram showing the sensor 230 and the main body 321. FIG. 27 is a cross-sectional diagram of the center of the electronic device 300 in the front view along the yz surface, and is a diagram showing a state viewed from the left side of the electronic device 300. However, in FIG. 27, only the back surface side of the wall surface 322 is illustrated.

As shown in FIG. 27, the main body 321 comprises a connecting part 323 on the back surface side of the wall surface 322. The connecting part 323 comprise a shaft bearing 323a for passing the shaft 315. A plate spring 324 is provided inside the shaft bearing 323a. The elastic force of the plate spring 324 fixes the vertical position of the measuring part 320 with respect to the shaft 315 to a predetermined position.

The sensor 230 comprises the arm 134. The arm 134 is connected to the wall surface 322 at one end 333a side. The arm 134 comprises, for example, a shaft bearing at one end 333a side, and is connected to the wall surface 322 by passing shafts S2, that is connected to both left and right side surfaces of the wall surface 322, through the shaft bearing. By connecting the sensor 230 to the wall surface 322 of the main body 321 in this way, as indicated by the arrow D in FIG. 27, the other end 333b side of the arm 134 can rotate, with axis S2 as the axis, on the yz surface. The arm 134 should be configured to be displaceable along a surface intersecting the surface in which the measuring part 320 is rotatably displaced.

The arm 134 is connected to the wall surface on the back surface side of the wall surface 322 via the elastic body 340. The arm 134 is connected to the wall surface 322 so that the other end 333b protrudes to the front side than the front end 322a of the wall section 322 in a state where the elastic body 340 is not pressed. That is, when the measuring part 320 is viewed from the left side of the electronic device 300, in a state where the elastic body 340 is not pressed, the other end 333b protrudes to the front side than the wall section 322.

The elastic body 340 may be, for example, a spring. However, the elastic body 340 is not limited to the spring, and may be any other elastic body such as resin, sponge or the like. In the example shown in FIG. 27, the elastic body 340 is a torsion coil spring, and the part near the center between one end 333a and the other end 333b is connected to the wall surface portion 322 by the torsion coil spring.

In this deformability, the arm 134 may be configured in the same manner as the first arm 134 of the electronic device 200 according to the second embodiment described above.

The electronic device 300 may comprise various functional parts, used for the electronic device 300 to measure the pulse wave at appropriate positions on the exterior 310 or the measuring part 320. For example, the electronic device 300 may comprise the foregoing controller, the power supply, the storage, the communicator, the notifier, a circuit for operating these, a cable for connecting them, and the like.

Another Modified Example of the Second Embodiment

Figure 28:
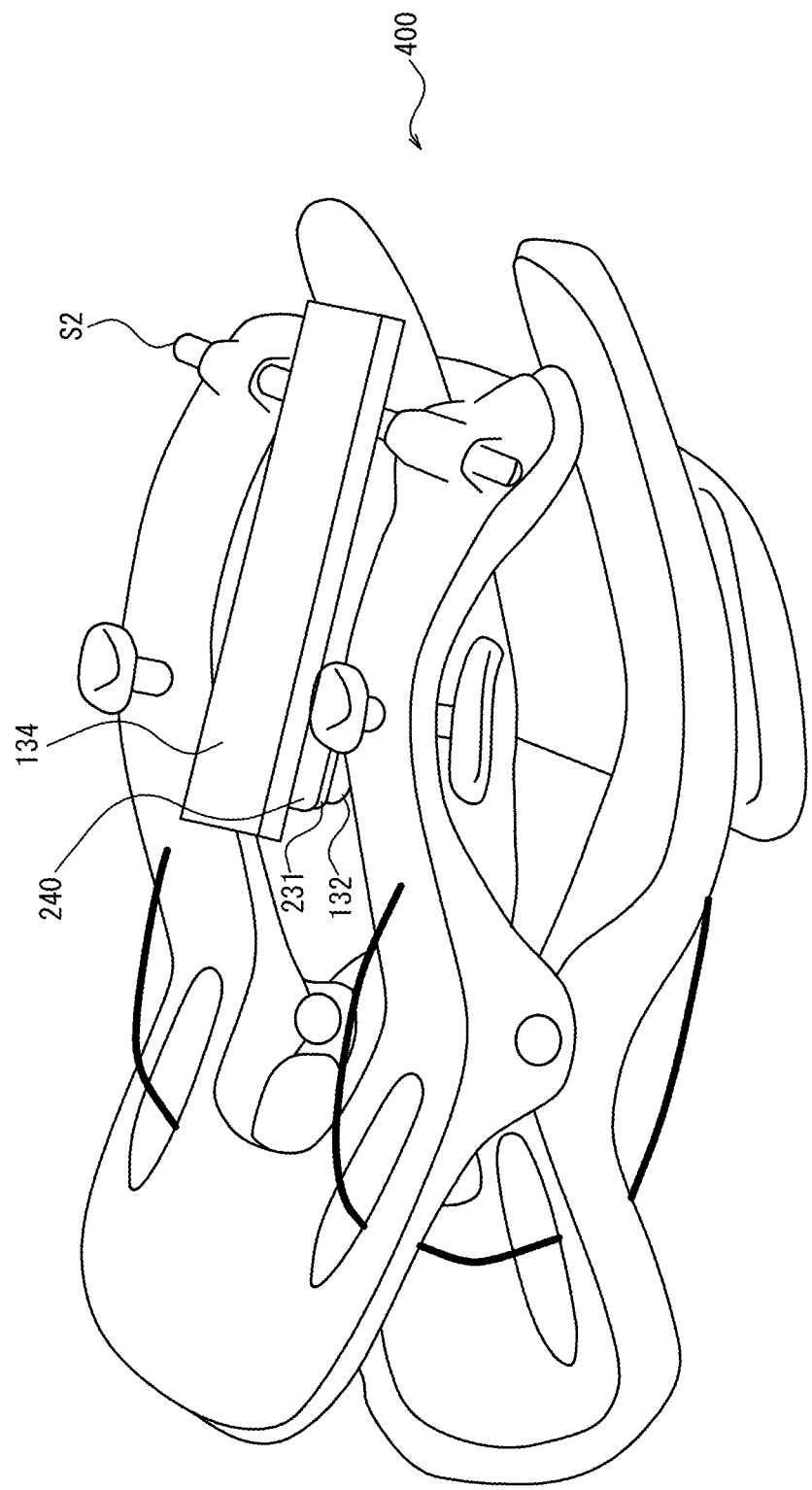
FIG. 28 is a schematic external perspective diagram of the electronic device according to another modified example of the second embodiment.

FIG. 28 is a schematic external perspective diagram of the electronic device according to another modified example of the second embodiment.

As shown in FIG. 28, the electronic device 400 according to another modified example of the second embodiment is a clip type electronic device configured to simplify the configuration of the foregoing electronic device 300 and be further worn to the examinee's wrist. The examinee or the examiner can keep the clip portion of the electronic device 400 open, and then keep the clip portion of the electronic device 400 closed at an appropriate position after positioning the device so that the area around the examinee's wrist is sandwiched by the electronic device 400. In the state in which the clip portion of the electronic device 400 is closed, the pulse contact pad 132 provided on the arm 134 is made to come into contact with the test part of the examinee. Here, the arm 134 is configured to be urged to the test part side of the examinee. Specifically, the arm 134 may be configured to be urged to the test part side of the examinee, centering on the shaft S2, by a plate spring, for example. Thus, the electronic device 400 can also improve the usefulness for the examinee to measure the pulse wave.

Still Another Modified Example of the Second Embodiment

Figure 29:
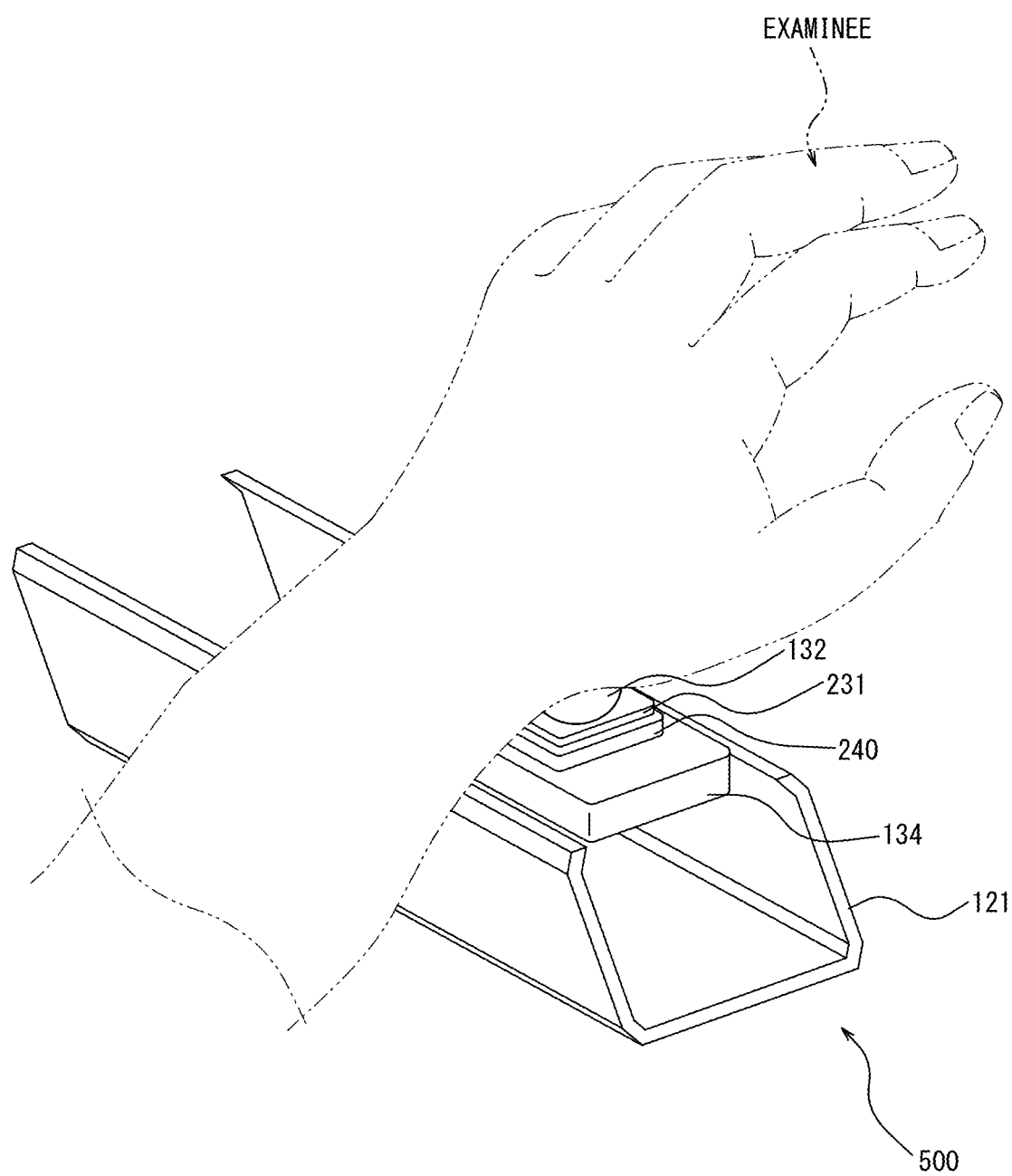
FIG. 29 is a schematic diagram showing how an examinee measures biological information using an electronic device according to yet another modified example of the second embodiment.

FIG. 29 is a schematic external perspective diagram of the electronic device according to another modified example of the second embodiment.

As shown in FIG. 29, an electronic device 500 according to another modified example of the second embodiment simplifies the configuration of the foregoing electronic device 300 so as to perform pulse wave detection by putting the examinee's wrist on the device. The arm 134 is displaceably attached to the main body 121 of the electronic device 500. Here, the arm 134 is configured to be urged to the test part side of the examinee. The examinee can perform the measurement by pressing his or her wrist against the appropriate position of the electronics device 500 under the appropriate pressure. When the examinee puts his or her wrist on the electronic device 500, the test part of the examinee is made to come into contact with the pulse contact pad 132 provided on the arm 134. Thus, the electronic device 500 can also improve the usefulness for the examinee to measure the pulse wave.

Still Another Modified Example of the Second Embodiment

Figure 30:
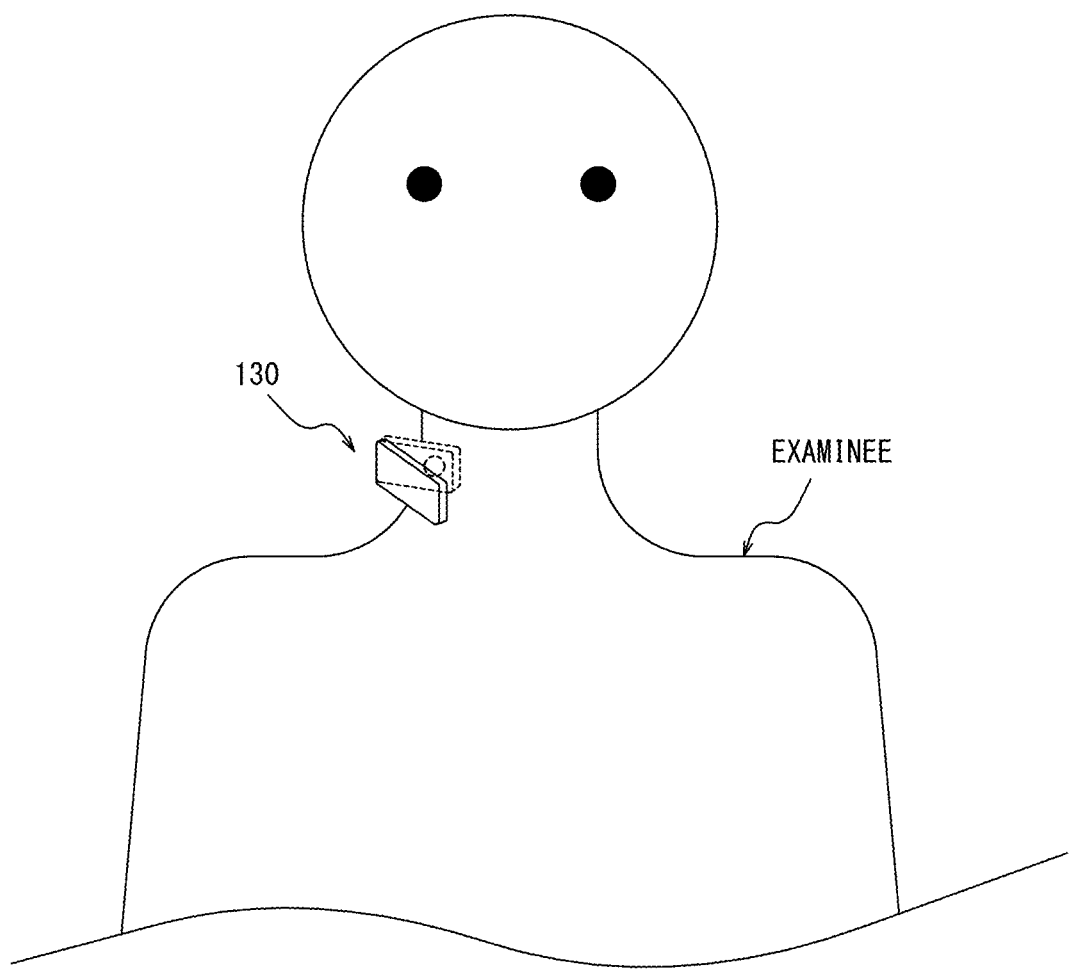
FIG. 30 is a schematic diagram showing how an examinee measures biological information using an electronic device according to yet another modified example of the second embodiment.

FIG. 30 is a schematic diagram of the electronic device according to another modified example of the second embodiment.

As shown in FIG. 30, an electronic device according to another modified example of the second embodiment simplifies the configuration of the foregoing electronic device 200 or electronic device 300 for only the sensor 130 to be made independent. FIG. 30 shows an example in which the sensor 130 detects the pulse wave on the carotid artery of the examinee. When the examinee detects the pulse wave on the test part by the sensor 130, the pulse contact pad 132 provided on the arm 134 is made to come into contact with the test part of the examinee. In this case, the examinee may hold the second arm 135 of the sensor 130 by his or her own hand or the like. By the examinee pressing the second arm 135 against the test part side, the arm 134 is urged to the test part side of the examinee. The examinee or the examiner can perform the measurement by pressing the sensor 130 against the appropriate position of the examinee under the appropriate pressure. Thus, the sensor 130 can also improve the usefulness for the examinee to measure the pulse wave.

Third Embodiment

Next, the third embodiment will be described. The electronic device according to the third embodiment performs an operation for realizing better measurement in the electronic device according to the foregoing second embodiment (including each modified example). The electronic device according to the third embodiment assists the positioning of the sensor at the test part of the examinee so as to satisfactorily measure the biological information of the examinee. Therefore, the examiner or the examinee can easily position the sensor at the test part of the examinee. Not only does the pulsation of the examinee vary greatly from person to person, but also the measurement result may differ considerably depending on which part of the examinee is used as the part to be tested. Therefore, if the positioning of the sensor is appropriately assisted at the test part of the examinee so that the biological information of the examinee can be measured satisfactorily, the usefulness of the electronic device can be greatly improved. Hereinafter, such an electronic device will be described.

The electronic device according to the third embodiment may have the same or similar configuration as any one of the electronic devices (or sensors) shown in FIGS. 16 and 17, and FIGS. 23 to 30. That is, in the electronic device according to the third embodiment, the sensor 231 may be configured to be urged to the test part of the examinee, as in the electronic device according to the second embodiment shown in FIG. 17, for example. Further, as shown in FIG. 17, for example, the sensor 231 may be urged to the test part of the examinee by the elasticity of the elastic member 240. In the third embodiment, the sensor 231 can detect the pulsation in the test part of the examinee as in the second embodiment.

Further, the electronic device according to the third embodiment may comprise, for example, a sensor 130 (sensor 231), a controller 143, and a notifier 147 among the functional parts shown in the block diagram of FIG. 6. In the third embodiment, the notifier 147 notifies the positional information of the sensor 231 at the test part. Information on the position of the sensor 231 at the test part will be further described below. Further, the electronic device according to the third embodiment may appropriately comprise other functional parts shown in the block diagram of FIG. 6. In other respects, the electronic device according to the third embodiment can be arbitrarily configured. Hereinafter, the description similar to that of the first embodiment or the second embodiment will be simplified or omitted as appropriate.

Figure 31:
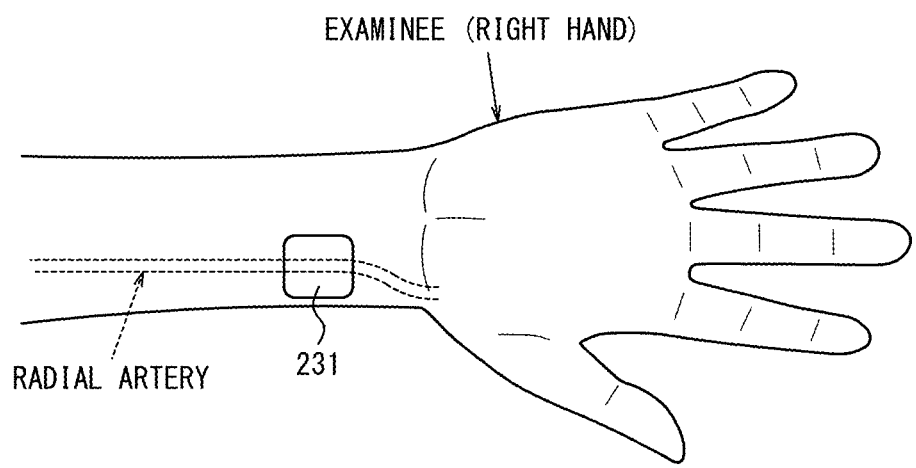
FIG. 31 is a diagram showing a usage of the electronic device according to the third embodiment.

FIG. 31 is a diagram showing a state in which the sensor 231 of the electronic device according to the third embodiment is urged to the right hand of the examinee. In the electronic device according to the third embodiment, the measurement is performed in a state where the sensor 231 is urged to the test part side of the examinee. In the electronic device according to the third embodiment, the functional parts other than the sensor 231 may be appropriately configured. Therefore, FIG. 31 shows only the sensor 231 among the functional parts constituting the electronic device according to the third embodiment, and the illustration of the other functional parts is omitted. Further, in the electronic device according to the third embodiment, the controller 143 and the notifier 147 described above may be built in the electronic device according to the third embodiment, or may be installed outside the electronic device according to the third embodiment. When the controller 143 and the notifier 147 are installed outside the electronic device according to the third embodiment, the sensor 231 and the controller 143 may be configured to be connected by a wire or wirelessly.

FIG. 31 shows an example of the radial artery in the examinee's right hand, indicated by the dashed line. As shown in FIG. 31, the sensor 231 of the electronic device according to the third embodiment can detect the pulsation on the radial artery of the examinee, for example, using the part corresponding to the position of the radial artery of the examinee as the test part. In the electronic device according to the third embodiment, as in the second embodiment, the sensor 231 may be urged to the test part by the elasticity of the elastic member 240.

Figure 32:
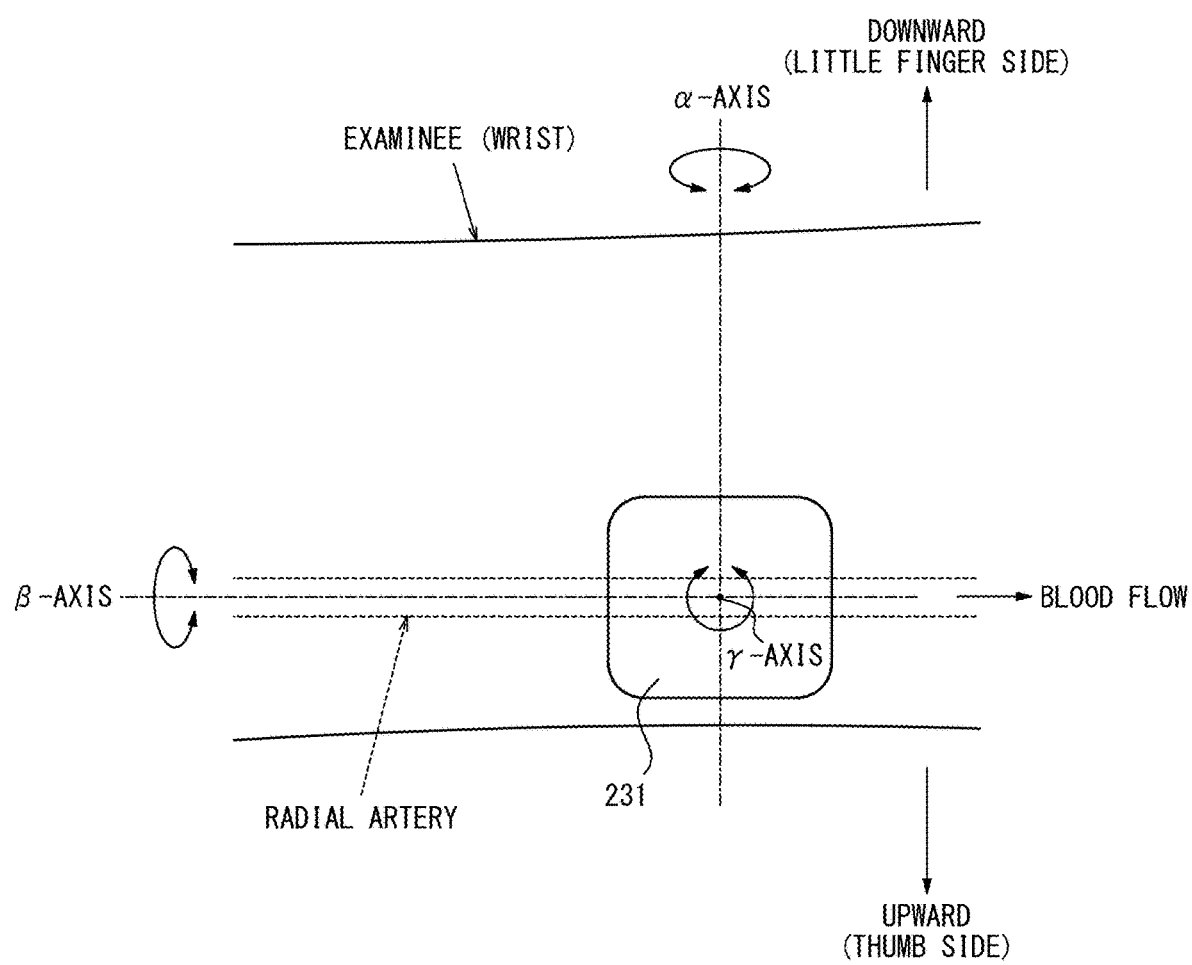
FIG. 32 is an enlarged diagram of the sensor shown in FIG. 31.

FIG. 32 is an enlarged view of the sensor 231 and the examinee's wrist in FIG. 31. FIG. 32 is a diagram showing a state in which the sensor 231 of the electronic device according to the third embodiment is urged to the right wrist of the examinee, as in FIG. 31. FIG. 32 schematically shows the radial artery of the examinee's right hand. In FIG. 32, the little finger side of the examinee is shown as "downward" and the thumb side of the examinee is shown as "upward". This is because, as can be seen in FIGS. 31 and 32, when the examinee turns the palm (and sensor 231) of the right hand toward himself or herself and points the elbow in the horizontal direction, the little finger side of the examinee faces "downward" and the thumb side of the examinee faces "upward". As shown in FIG. 32, in the radial artery of the examinee, the arterial flow (blood flow) is assumed to flow from the left direction to the right direction.

Figure 33:
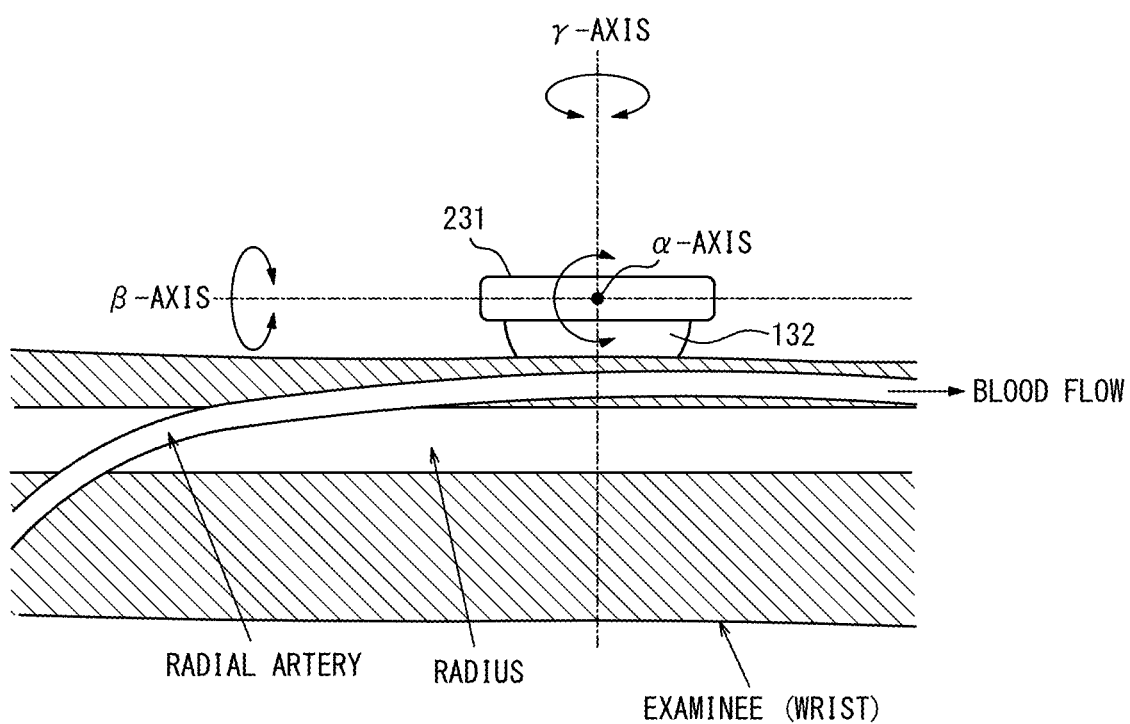
FIG. 33 is a cross-sectional diagram of FIG. 32 viewed from different directions.

FIG. 33 is a cross-sectional diagram in which the sensor 231 and the examinee's wrist shown in FIG. 32 are viewed from a direction different from that in FIG. 32. FIG. 33 is a cross-sectional diagram in which the sensor 231 and the examinee's wrist as shown in FIG. 32, are viewed from top (thumb side) to bottom (little finger side). FIG. 33 schematically shows an example of radius and radial artery of an examinee in a cross section of the examinee's wrist. As shown in FIG. 33, in the sensor 231 according to the third embodiment, as in the second embodiment, a pulse contact pad 132 may be provided at a portion that comes into contact with the test part of the examinee. Further, in the electronic device according to the third embodiment, as in the second embodiment, the sensor 231 may be urged to the test part by the elasticity of the elastic member 240. In FIGS. 32 and 33, the illustration of the elastic member 240 is omitted.

In the electronic device according to the third embodiment, the elastic member 240 may be configured to include any elastic body having appropriate elasticity, such as a spring, a resin, or a sponge, as in the second embodiment. The elastic member 240 may be formed of, for example, a silicone sheet having a predetermined elasticity and a predetermined thickness. In the electronic device according to the third embodiment, the sensor 231 is given some free range of motion due to the flexibility of the elastic member 240. In addition, the flexibility of the elastic member 240 makes the motion of the sensor 231 less hindered. Further, because the elastic member 240 has an appropriate elasticity, the elastic member 240 deforms following the pulsation at the test part of the examinee. Therefore, in the electronic device according to the third embodiment, the sensor 231 can sensitively detect the pulsation in the test part of the examinee. As described above, in the electronic device according to the third embodiment, the elastic member 240 may be deformable according to the pulsation at the test part of the examinee. Further, the elastic member 240 may be elastically deformed to such an extent that the sensor 231 can detect the pulsation at the test part of the examinee.

The sensor 231 of the electronic device according to the third embodiment may be, for example, an acceleration sensor or a sensor such as a gyro sensor, as in the second embodiment. Hereinafter, a case in which the sensor 231 of the electronic device according to the third embodiment is a gyro sensor will be described. As described above, the sensor 231 of the electronic device according to the third embodiment may detect the pulsation of the examinee at the test part as a part of the rotational motion centering on a predetermined axis. More specifically, the sensor 231 may detect the pulsation at the test part of the examinee as at least biaxial rotational motion, or may detect it as, for example, triaxial rotational motion. For example, as shown in FIGS. 32 and 33, the sensor 231 may detect the pulsation at the test part of the examinee as the rotational motion of the three axes of the α-axis, the β-axis, and the γ-axis.

When the radial artery of the examinee pulsates due to blood flow, a part of the radial artery slightly distends due to the pulsation and becomes thicker than the other part. In addition, the distended portion moves with the blood flow along the radial artery. For example, in the radial artery shown in FIG. 33, a portion slightly distended due to pulsation moves in the direction of blood flow shown in FIG. 33. When the part of the radial artery shown in FIG. 33 that is slightly distended due to pulsation arrives at the position of the sensor 231 (test part), the sensor 231 detects a slight rotational motion in a clockwise direction centering on the α-axis shown in FIG. 33. After that, when the portion of the radial artery slightly distended due to pulsation passes through the position of the sensor 231 (test part), the sensor 231 detects a slight rotational motion in the counterclockwise direction centering on the α-axis by the elasticity of the elastic member 240. In this way, the electronic device according to the third embodiment can detect the pulsation at the test part of the examinee as (a part of) the rotational motion centering on the α-axis.

As shown in FIGS. 32 and 33, the β-axis on which the sensor 231 detects the rotational motion may be an axis substantially parallel to the direction of blood flow in the radial artery of the examinee. Further, as shown in FIG. 32, the γ-axis on which the sensor 231 detects the rotational motion may be an axis in the direction perpendicular to the surface of the test part of the examinee. As shown in FIGS. 32 and 33, the three axes of the α-axis, the β-axis, and the γ-axis in which the sensor 231 detects the rotational motion may be oriented orthogonal to each other. The sensor 231 shown in FIGS. 32 and 33 is almost square in shape when viewed from the γ-axis direction. However, in the third embodiment, the shape of the sensor 231 as viewed from the γ-axis direction may be various shapes such as a circle, an ellipse, a rectangle, a rhombus, or a parallelogram.

Next, the positional relationship between the sensor 231 in the third embodiment and the artery will be described.

Figure 34A:
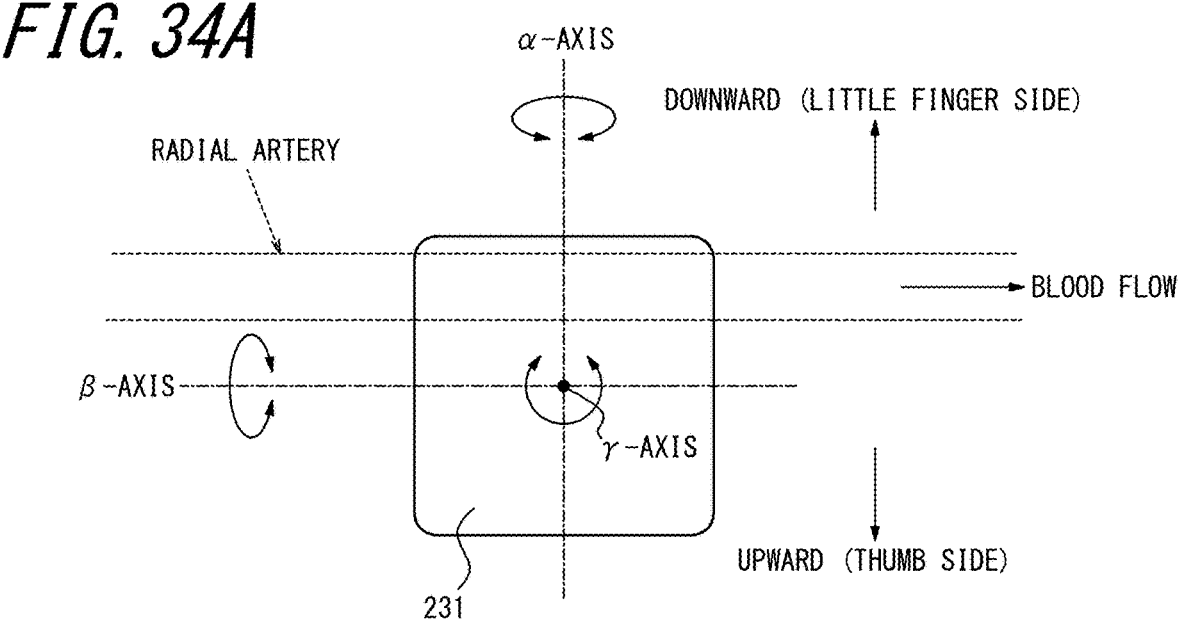
FIG. 34A is a diagram illustrating a measurement principle of the electronic device according to the third embodiment.
Figure 34B:
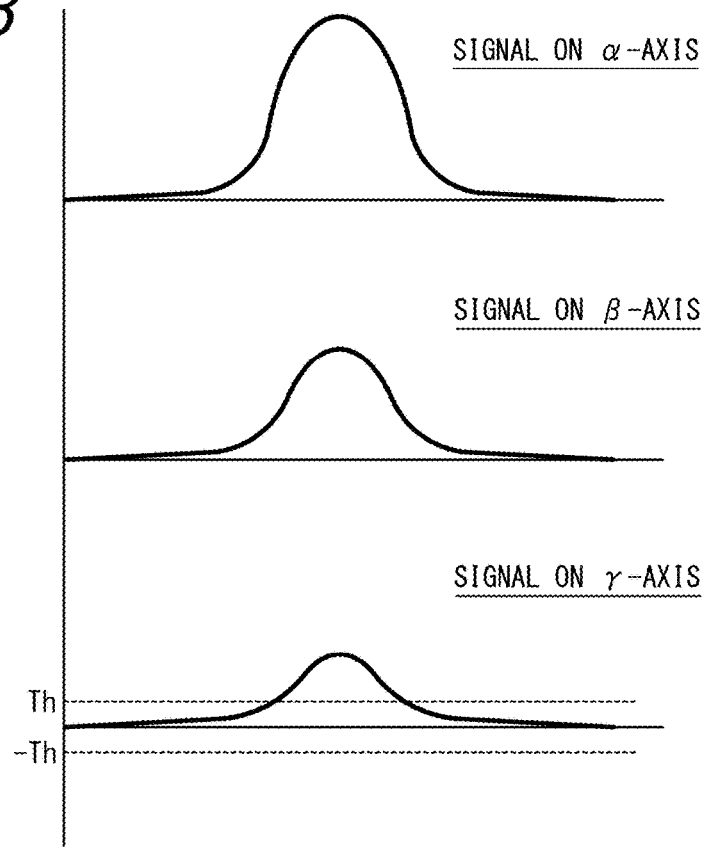
FIG. 34B is a diagram illustrating a measurement principle of the electronic device according to the third embodiment.

FIG. 34A is a diagram illustrating the positional relationship between the sensor 231 in the third embodiment and the radial artery of the examinee. In the example shown in FIG. 34A, the central part of the sensor 231 (the point where the γ-axis penetrates the sensor 231) is located above the radial artery of the examinee (thumb side). In such a case, when the portion of the radial artery slightly distended by pulsation reaches the position of the sensor 231 (test part) and passes therethrough, a detection signal as shown in FIG. 34B is obtained. FIG. 34B is a graph showing the time variation of the signal intensity, in which the sensor 231 detected the pulsation at the test part of the examinee as the rotational motion of 3 axes of the α-axis, β-axis, and γ-axis, for each axis.

In the arrangement shown in FIG. 34A, it is assumed that a portion of the radial artery slightly distended due to pulsation reaches and passes through the test part. In this case, as described above, the sensor 231 detects a slight rotational motion in the clockwise direction centering on the α-axis shown in FIG. 33 and then detects a slight rotational motion in the counterclockwise direction. Therefore, a peak, as shown in the upper part of FIG. 34B, is detected in the signal of rotational motion centering on the α-axis of the sensor 231.

Further, in this case, the sensor 231 detects a rotational motion in which the portion of the sensor 231 overlapping the radial artery is slightly lifted centering on the β-axis shown in FIG. 34A. Then, the sensor 231 detects a rotational motion that returns to its original state due to the elasticity of the elastic member 240 centering on the β-axis shown in FIG. 34A. Therefore, a peak, as shown in the middle part of FIG. 34B, is detected in the signal of the rotational motion centering on the β-axis of the sensor 231.

Further, in this case, when the portion of the radial artery slightly distended due to pulsation reaches the test part, the end of the sensor 231 is slightly pushed in the direction of blood flow. Therefore, the sensor 231 detects a slight rotational motion in the clockwise direction centering on the γ-axis shown in FIG. 34A. After that, when the portion of the radial artery slightly distended due to pulsation passes through the test part, the sensor 231 detects a slight rotational motion in the counterclockwise direction centering on the γ-axis that returns to its original state due to the elasticity of the elastic member 240. Therefore, a peak, as shown in the lower part of FIG. 34B, is detected in the signal of the rotational motion of the sensor 231 centering on the γ-axis. In this way, if the central part of the sensor 231 (the point where the γ-axis penetrates the sensor 231) deviates from the position of the radial artery, a peak; for example, as shown in the lower part of FIG. 34B, is detected in the signal of rotational motion centering on the γ-axis.

Figure 35A:
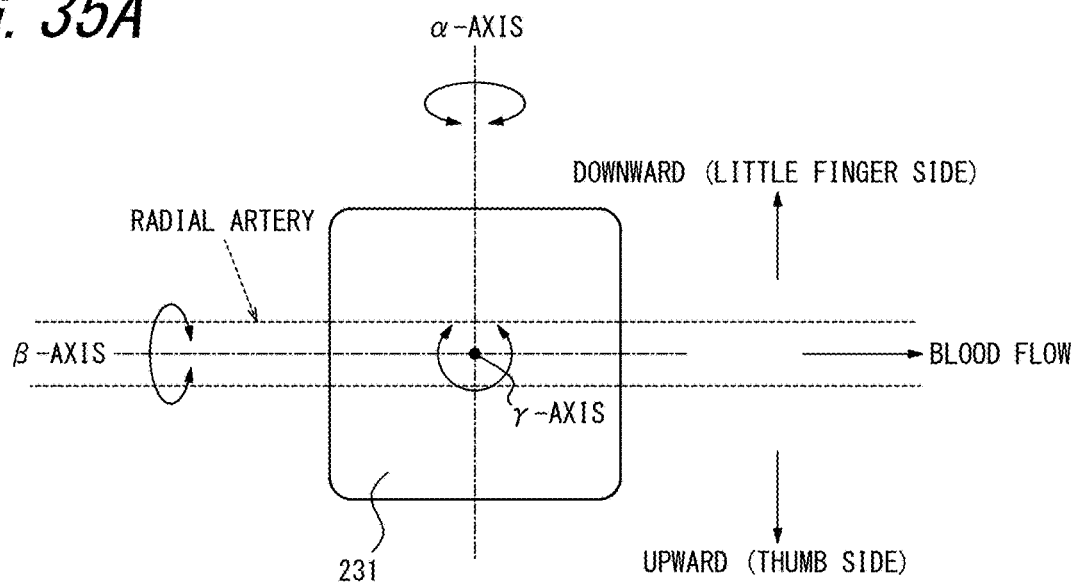
FIG. 35A is a diagram illustrating a measurement principle of the electronic device according to the third embodiment.
Figure 35B:
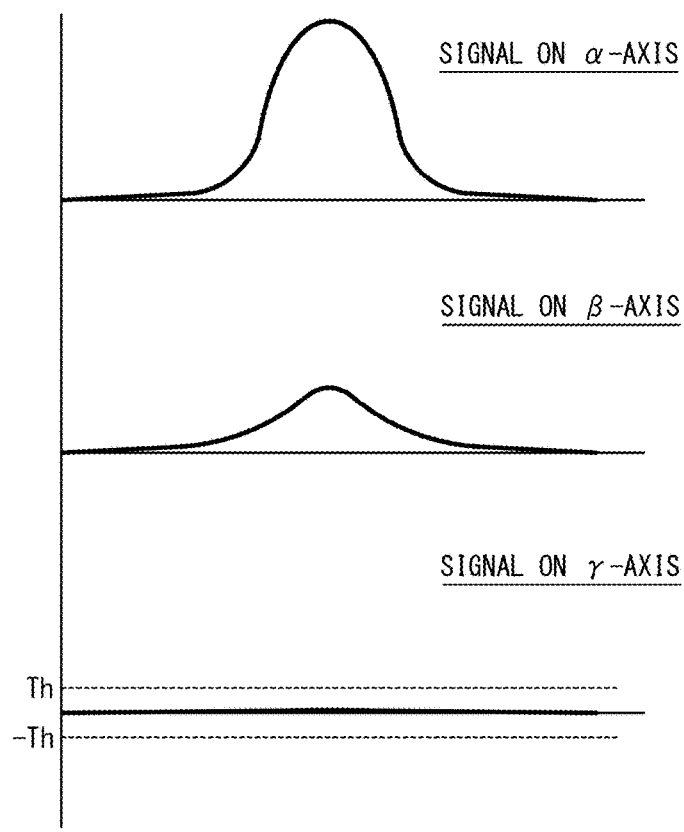
FIG. 35B is a diagram illustrating a measurement principle of the electronic device according to the third embodiment.

Next, in the example shown in FIG. 35A, the central part of the sensor 231 (the point where the γ-axis penetrates the sensor 231) is located on the radial artery of the examinee. That is, in the example shown in FIG. 35A, the position of the central part of the sensor 231 (the point where the γ-axis penetrates the sensor 231) is not deviated neither above (thumb side) nor below (little finger side) the radial artery of the examinee. In such a case, when the portion of the radial artery slightly distended due to pulsation reaches the position of the sensor 231 (test part) and passes therethrough, a detection signal as shown in FIG. 35B is obtained. As FIG. 34B, FIG. 35B is also a graph showing the time variation of the intensity of the signal, in which the sensor 231 detected the pulsation at the test part of the examinee as the rotational motion of 3 axes of the α-axis, β-axis, and γ-axis, for each axis.

In the arrangement shown in FIG. 35A, it is assumed that a portion of the radial artery slightly distended due to pulsation reaches and passes through the test part. In this case, as described above, the sensor 231 detects a slight rotational motion in the clockwise direction centering on the α-axis shown in FIG. 33 and then detects a slight rotational motion in the counterclockwise direction. Therefore, a peak, as shown in the upper part of FIG. 35B, is detected in the signal of the rotational motion of the sensor 231 centering on the α-axis.

Further, in this case, the sensor 231 detects a rotational motion in which the portion of the sensor 231 overlapping the radial artery is slightly lifted centering on the β-axis shown in FIG. 35A. Then, the sensor 231 detects a rotational motion that returns to its original state due to the elasticity of the elastic member 240 centering on the β-axis shown in FIG. 35A. Therefore, a peak, as shown in the middle part of FIG. 35B, is detected in the signal of the rotational motion centering on the β-axis of the sensor 231.

On the other hand, in this case, as shown in FIG. 35a, the central part of the sensor 231 (the point where the γ-axis penetrates the sensor 231) is located on the line indicating the direction of pulsation (blood flow) in the radial artery. In this case, even if the portion of the radial artery that is slightly distended due to pulsation reaches the test part, the sensor 231 does not detect a slight rotational motion in the clockwise direction centering on the γ-axis, nor a slight rotational motion in the counterclockwise direction centering on the γ-axis. Therefore, as shown in the lower part of FIG. 35B, no conspicuous peak is detected in the signal of the rotational motion of the sensor 231 centering on the γ-axis. In this way, when the central part of the sensor 231 (the point where the γ-axis penetrates the sensor 231) does not deviate from the position of the radial artery, no peak, for example, as shown in the lower part of FIG. 35B, is detected in the signal of the rotational motion centering on the γ-axis.

Figure 36A:
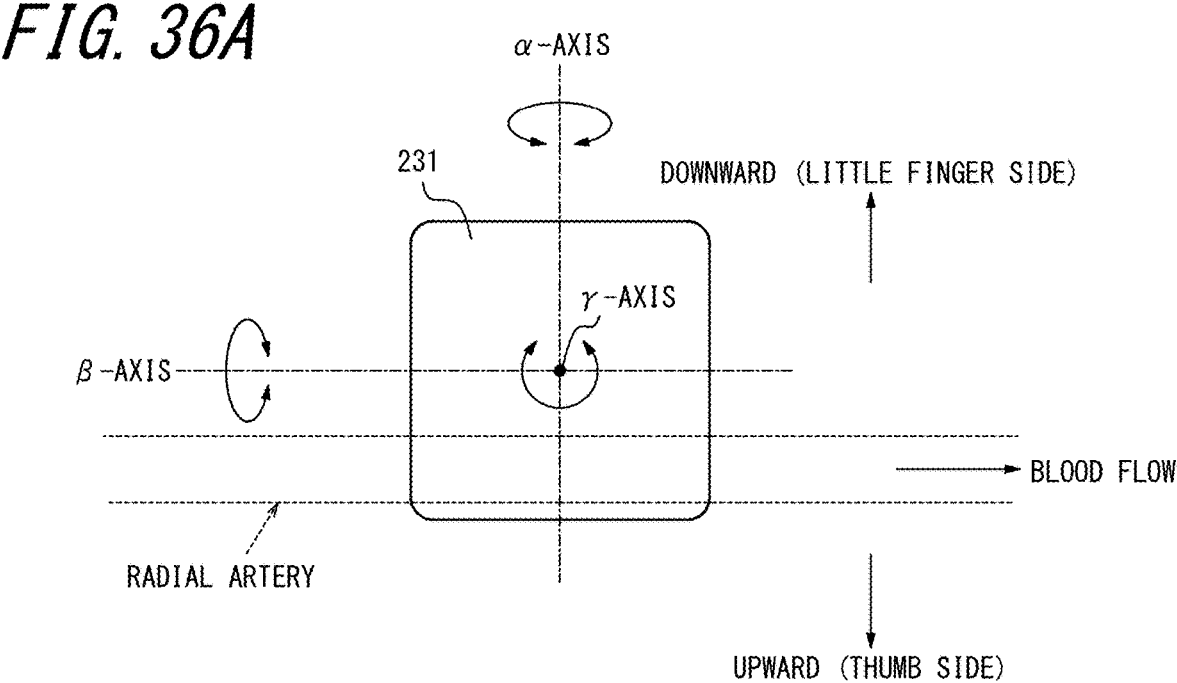
FIG. 36A is a diagram illustrating a measurement principle of the electronic device according to the third embodiment.
Figure 36B:
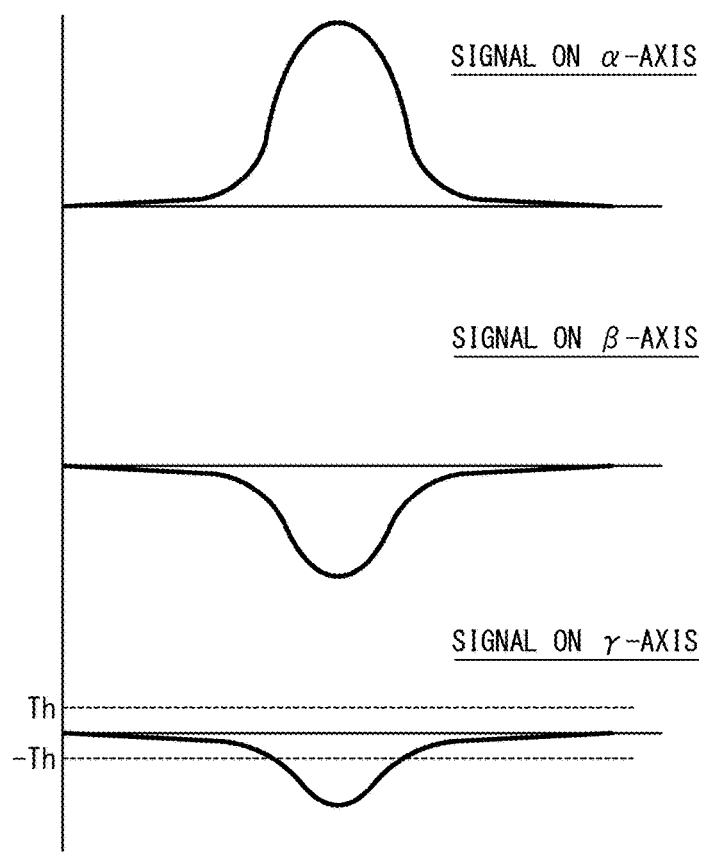
FIG. 36B is a diagram illustrating a measurement principle of the electronic device according to the third embodiment.

Next, in the example shown in FIG. 36A, the central part of the sensor 231 (the point at which the γ-axis penetrates the sensor 231) is located off to the bottom (little finger side) of the radial artery of the examinee. In such a case, when the portion of the radial artery slightly distended due to pulsation reaches the position of the sensor 231 (test part) and passes therethrough, a detection signal as shown in FIG. 36B is obtained. As FIG. 34B, FIG. 36B is also a graph showing the time variation of the intensity of the signal, in which the sensor 231 detected the pulsation at the test part of the examinee as the rotational motion of 3 axes of the α-axis, β-axis, and γ-axis, for each axis.

In the arrangement shown in FIG. 36A, it is assumed that a portion of the radial artery slightly distended due to pulsation reaches and passes through the test site. In this case, as described above, the sensor 231 detects a slight rotational motion in the clockwise direction centering on the α-axis shown in FIG. 33 and then detects a slight rotational motion in the counterclockwise direction. Therefore, a peak, as shown in the upper part of FIG. 36B, is detected in the signal of the rotational motion centering on the α-axis of the sensor 231.

Further, in this case, the sensor 231 detects a rotational motion in which the portion of the sensor 231 overlapping the radial artery is slightly lifted, centering on the β-axis shown in FIG. 36A. Then, the sensor 231 detects a rotational motion that returns to its original state due to the elasticity of the elastic member 240 centering on the β-axis shown in FIG. 36A. Therefore, a peak, as shown in the middle part of FIG. 36B, is detected in the signal of the rotational motion centering on the β-axis of the sensor 231. The rotational motion centering on the β-axis shown in FIG. 36A is in the opposite rotation direction to the rotational motion centering on the β-axis shown in FIG. 34A. Therefore, the positive/negative of the peak shown in the middle part of FIG. 36B is opposite to the positive/negative of the peak shown in the middle part of FIG. 34B.

Further, in this case, when the portion of the radial artery slightly distended due to pulsation reaches the test part, the end of the sensor 231 is slightly pushed in the direction of blood flow. Therefore, the sensor 231 detects a slight rotational motion in counterclockwise direction centering on the γ-axis shown in FIG. 36A. After that, when the portion of the radial artery slightly distended due to pulsation passes through the test part, the sensor 231 detects a slight rotational motion in the clockwise direction centering on the γ-axis that returns to its original state due to the elasticity of the elastic member 240. Therefore, a peak, as shown in the lower part of FIG. 36B, is detected in the signal of the rotational motion of the sensor 231 centering on the γ-axis. In this way, if the central part of the sensor 231 (the point where the γ-axis penetrates the sensor 231) deviates from the position of the radial artery, for example, a peak, as shown in the lower part of FIG. 36B, is detected in the signal of the rotational motion centering on the γ-axis. The rotational motion centering on the γ-axis shown in FIG. 36A is in the opposite rotation direction to the rotational motion centering on the γ-axis shown in FIG. 34A. Therefore, the positive/negative of the peak shown in the lower part of FIG. 36B is opposite to the positive/negative of the peak shown in the lower part of FIG. 34B.

As described above, when the central part of the sensor 231 (the point where the γ-axis penetrates the sensor 231) does not deviate from the position of the radial artery, that is, when the sensor 231 is in an appropriate position at the test part, no peak is detected in the signal of rotational motion centering on the γ-axis. On the other hand, when the central part of the sensor 231 (the point where the γ-axis penetrates the sensor 231) deviates from the position of the radial artery, that is, when the sensor 231 is not in an appropriate position at the test part, a peak is detected in the signal of rotational motion centering on the γ-axis. Therefore, in the electronic device according to the third embodiment, the controller 143 can determine whether the sensor 231 is in an appropriate position at the test part based on whether a predetermined peak is detected in the signal of rotational motion centering on the γ-axis.

For example, as shown in FIG. 34B, when the signal on the γ-axis has a peak exceeding a predetermined threshold value Th in the positive direction, the controller 143 can determine that the sensor 231 is above the radial artery (thumb side). Further, as shown in FIG. 36B, when the signal on the γ-axis has a peak in the negative direction below a predetermined threshold value −Th in the negative direction, the controller 143 can determine that the sensor 231 is below the radial artery (on the little finger side). On the other hand, as shown in FIG. 35B, when the signal on the γ-axis does not have a peak exceeding a predetermined threshold value Th in the positive direction and does not have a peak in the negative direction below a predetermined threshold value −Th in the negative direction, the controller 143 can determine that the sensor 231 is in an appropriate position.

The threshold values Th and −Th shown in FIGS. 34B to 369 may be positive or negative values having the same absolute values, or positive or negative values having different absolute values. Further, as the threshold values Th and −Th, for example, general representative values may be set in advance by experiments or the like according to the gender and/or age of the examinee. Further, the threshold values Th and −Th may be set in consideration of the individual physical characteristics for each examinee, for example. The threshold values Th and −Th may be set as appropriate, based on the positional relationship in which the position of the pulsation and the position of the sensor 231 do not deviate from each other at the test part of the examinee and the pulsation of the examinee is appropriately detected by the sensor 231. In addition, the positive and negative of threshold values Th and −Th may be also appropriately set based on the positive and negative directions of the peak in the γ-axis direction detected when the position of the pulsation deviates from the position of the sensor 231 in the test part of the examinee.

In the electronic device 1 according to the third embodiment, the controller 143 may notify predetermined information from the notifier 147 based on the result obtained by determining the position of the sensor 231 at the test part as described above. For example, the notifier 147 may notify the examinee and/or the examiner whether the position of the pulsation are deviated from the position of the sensor 231, in the test part of the examinee, by voice, display, and/or tactile sense. Further, if the position of the pulsation are deviated from the position of the sensor 231, in the test part of the examinee, the notifier 147 may notify the examinee and/or the examiner of the position where appropriate measurement can be made by voice, display, and/or tactile sense. For example, if the positional relationship shown in FIG. 34A is determined, the notifier 147 may provide notification by voice guidance or display, such as "Please shift the sensor downward (to the little finger side)". When the positional relationship shown in FIG. 36A is determined, the notifier 147 may provide notification by voice guidance or display, such as "Please shift the sensor upward (to the thumb side)". On the other hand, if the positional relationship shown in FIG. 35A is determined, the notifier 147 may provide notification by voice guidance or display, such as "The position of the sensor is appropriate".

Furthermore, for example, if the positional relationship shown in FIG. 34A is determined, the notifier 147 may generate vibrations at any lower (little finger side) locations of the housing of the electronic device, for example, to notify by tactile sense that the sensor should be shifted downward (little finger side). Further, for example, if the positional relationship shown in FIG. 36A is determined, the notifier 147 may generate a vibration at any upper (thumb side) locations of the housing of the electronic device, for example, to notify by tactile sense that the sensor should be shifted upward (thumb side). On the other hand, if the positional relationship shown in FIG. 35A is determined, the notifier 147 may generate vibrations at both the lower (little finger side) and upper (thumb side) locations of the housing of the electronic device, for example, or may not generate vibrations at both the locations.

As described above, in the electronic device according to the third embodiment, the controller 143 controls the notifier 147 so as to notify information for the position of the sensor 231 at the test part based on the pulsation of the examinee at the test part detected by the sensor 231. Here, the controller 143 may determine the position of the sensor 231 at the test part based on the pulsation at the test part detected by the sensor 231. Further, the controller 143 may notify the information for the position of the sensor 231 at the test part by stimulating at least one of the visual sense, the auditory sense, and the tactile sense of the examinee.

Further, in the electronic device according to the third embodiment, the controller 143 may determine the position of the sensor 231 at the test part based on the pulsation at the test part detected as part of the rotational motion centering on a predetermined axis. Here, the predetermined axis may be an axis in a direction perpendicular to the surface of the test part, such as the γ-axis. Further, when the signal based on the pulsation at the test part detected as a part of the rotational motion centering on a predetermined axis is within a predetermined range, the controller 143 may determine that the position of the sensor 231 at the test part is appropriate. In this case, the controller 143 may control the notifier 147 to notify the information that the position of the sensor 231 at the test part is appropriate.

On the other hand, when the signal based on the pulsation at the test part detected as a part of the rotational motion centering on the predetermined axis is out of the predetermined range, the controller 143 may determine that the position of the sensor 231 at the test part is not appropriate. In this case, the controller 143 may control the notifier 147 to notify the information that the position of the sensor 231 at the test part is not appropriate. Further, in this case, the controller 143 may control the notifier 147 to notify the guidance information so that the position of the sensor 231 at the test part becomes appropriate.

Figure 37:
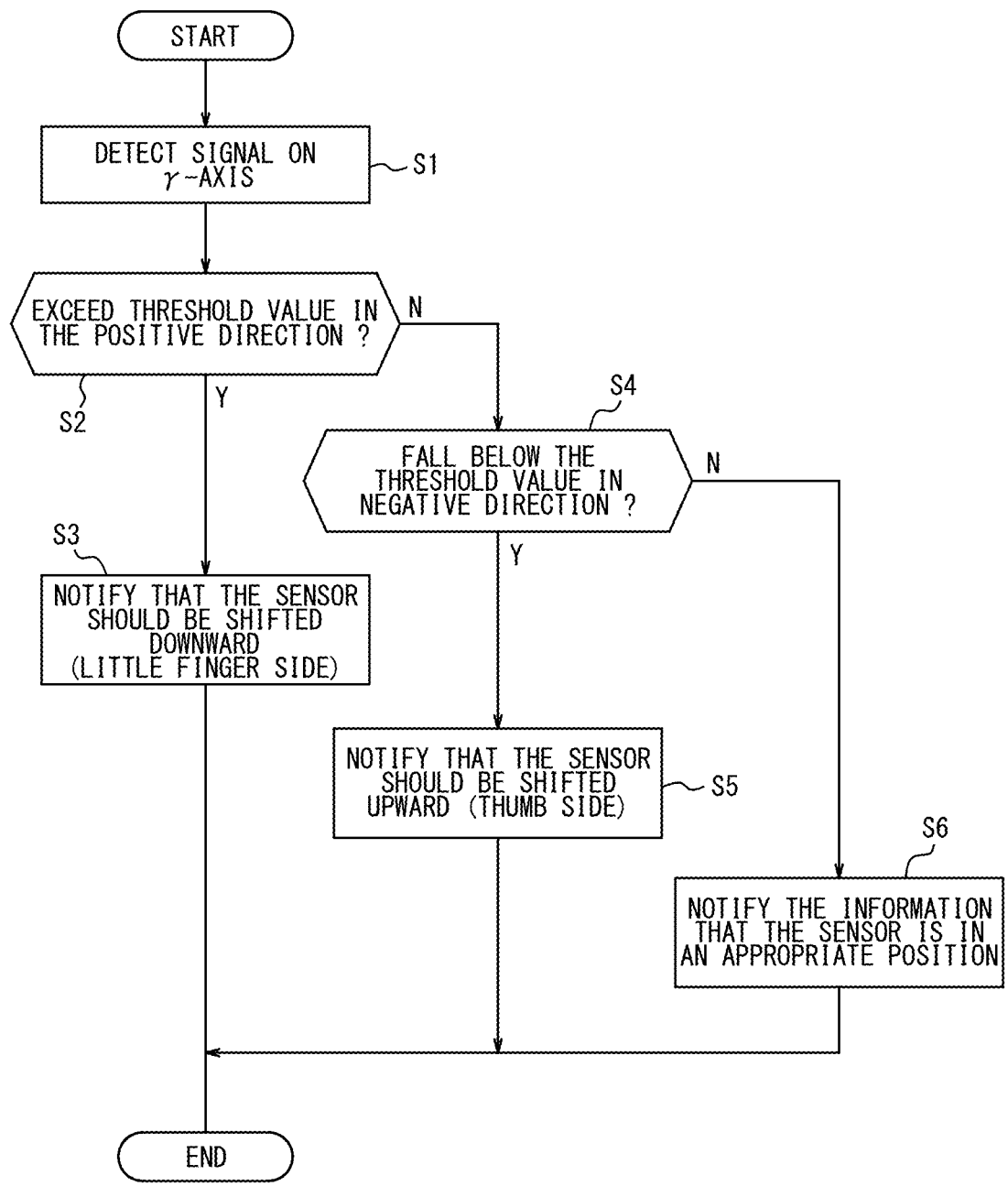
FIG. 37 is a flowchart showing a procedure for operating the electronic device according to the third embodiment.

FIG. 37 is a flowchart showing a procedure for operating the electronic device according to the third embodiment. Hereinafter, the operation of the electronic device according to the third embodiment will be described.

The operation shown in FIG. 37 may be started when the positioning of the sensor 231 is appropriately performed at the test part of the examinee before measuring the biological information of the examinee by the electronic device according to the third embodiment.

When the operation shown in FIG. 37 starts, the sensor 231 detects a signal based on the rotational motion centering on the γ-axis as shown in FIGS. 32 and 33 (step S1).

When the signal on γ-axis is detected in step S1, the controller 143 determines whether the signal exceeds the threshold value Th in the positive direction (step S2). For example, in the example shown in FIG. 34B, the signal on the γ-axis exceeds the threshold value Th in the positive direction. On the other hand, in the examples shown in FIGS. 35B and 36B, the signal on the γ-axis does not exceed the threshold value Th in the positive direction.

When the signal on the γ-axis exceeds the threshold value Th in the positive direction in step S2, the controller 143 controls the notifier 147 to notify the information that the sensor 231 should be shifted downward (little finger side) (step S3).

On the other hand, if the signal on the γ-axis does not exceed the threshold Th in the positive direction in step S2, the controller 143 determines whether the signal on γ-axis falls below the threshold −Th in the negative direction (step S4). For example, in the example shown in FIG. 35B, the signal on the γ-axis does not fall below the threshold value Th in the negative direction. On the other hand, in the example shown in FIG. 36B, the signal on the γ-axis falls below the threshold value −Th in the negative direction.

When the signal on the γ-axis falls below the threshold value −Th in the negative direction in step S4, the controller 143 controls the notifier 147 to notify the information that the sensor 231 should be shifted upward (thumb side) (step S5).

On the other hand, when the signal on the γ-axis does not fall below the threshold value −Th in the negative direction in step S4, the controller 143 controls the notifier 147 to notify the information that the sensor 231 is in an appropriate position (step S6).

According to the electronic device of the third embodiment, the positioning of the sensor at the test part of the examinee can be assisted so as to measure the examinee's biological information well. Therefore, according to the electronic device of the third embodiment, the examiner or the examinee can easily position the sensor at the test part of the examinee. Therefore, according to the electronic device of the third embodiment, not only better measurement can be realized, but also the usefulness of the electronic device can be significantly improved.

REFERENCE SIGNS LIST

100 Electronic device
110 Wearing part
110a, 134a, 135a One end
110b, 134b, 135b The other end
111 Base
112 Fixing part
120 Measuring part
121 Main body
122 Exterior
122a Contact surface
122b Surface
122c Notch
122d End
123 Coupling part
124 Shaft
125 Opening
130 Sensor
131 Angular velocity sensor
132 Pulse contact pad
134 First arm
135 Second arm
136 Stopper
140 Elastic body
143 Controller
144 Power supply 145 Storage
146 Communicator
147 Notifier
150 Mobile terminal
151 Server
230 Sensor
231 Sensor
240 Elastic member

The invention claimed is:

1. An electronic device comprising:
a sensor configured to be urged to a test part side of an examinee and to be able to detect pulsation at the test part,
a notifier configured to notify information for a position of the sensor at the test part, and
a controller configured to control the notifier to notify information for a position of the sensor at the test part based on pulsation at the test part detected by the sensor.

2. The electronic device, according to claim 1,
wherein the controller determines a position of the sensor at the test part based on pulsation at the test part detected by the sensor.

3. The electronic device, according to claim 1,
wherein the notifier notifies information for a position of the sensor at the test part by stimulating at least any one of a visual sense, an auditory sense, and a tactile sense of the examinee.

4. The electronic device, according to claim 1,
wherein the sensor is urged to the test part by elasticity of elastic member, and the elastic member is deformable according to pulsation at the test part.

5. The electronic device, according to claim 4,
wherein the elastic member is elastically deformed to such an extent that the sensor can detect pulsation at the test part.

6. The electronic device, according to claim 1,
wherein the sensor detects pulsation at the test part as a part of a rotational motion centering on a predetermined axis.

7. The electronic device, according to claim 6,
wherein the sensor detects pulsation at the test part as rotational motion in at least two axes.

8. The electronic device, according to claim 7,
wherein the sensor detects pulsation at the test part as rotational motion in three axes.

9. The electronic device, according to claim 6,
wherein the sensor is a gyro sensor.

10. The electronic device, according to claim 6,
wherein the controller determines a position of the sensor at the test part based on pulsation at the test part detected as a part of a rotational motion centering on the predetermined axis.

11. The electronic device, according to claim 10,
wherein the controller determines that a position of the sensor at the test part is appropriate when a signal based on pulsation at the test part detected as a part of a rotational motion centering on the predetermined axis is within a predetermined range.

12. The electronic device, according to claim 10,
wherein the predetermined axis is an axis in a direction perpendicular to a surface of the test part.

* * * * *